United States Patent
Ramasamy et al.

(10) Patent No.: US 6,642,206 B2
(45) Date of Patent: *Nov. 4, 2003

(54) MONOCYCLIC L-NUCLEOSIDES, ANALOGS AND USES THEREOF

(75) Inventors: Kanda Ramasamy, Aliso Viejo, CA (US); Robert Tam, Irvine, CA (US); Devron Averett, Irvine, CA (US)

(73) Assignee: ICN Pharmaceuticals, Inc., Costa Mesa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/120,101

(22) Filed: Apr. 9, 2002

(65) Prior Publication Data

US 2003/0018186 A1 Jan. 23, 2003

Related U.S. Application Data

(62) Division of application No. 09/969,355, filed on Oct. 1, 2001, now Pat. No. 6,573,248, which is a division of application No. 09/633,493, filed on Aug. 7, 2000, now Pat. No. 6,552,183, which is a division of application No. 09/291,903, filed as application No. PCT/US97/18767 on Oct. 15, 1997, now Pat. No. 6,130,326.
(60) Provisional application No. 60/028,585, filed on Oct. 16, 1996.

(51) Int. Cl.[7] .................. C07H 19/056; A61K 31/70
(52) U.S. Cl. .................................... 514/43; 536/28.7
(58) Field of Search .................. 536/28.7; 514/43

(56) References Cited

U.S. PATENT DOCUMENTS

| | | | | | |
|---|---|---|---|---|---|
| 3,948,885 A | * | 4/1976 | Witkowski et al. | ......... | 536/26.9 |
| 4,138,547 A | * | 2/1979 | Christensen et al. | ........ | 536/28.7 |
| 4,992,426 A | * | 2/1991 | Robins et al. | ................. | 514/43 |
| 5,082,829 A | * | 1/1992 | Gruber et al. | ................ | 514/43 |
| 5,248,776 A | * | 9/1993 | Chu et al. | .................... | 544/310 |
| 5,559,101 A | * | 9/1996 | Weis et al. | .................... | 514/45 |
| 5,561,120 A | * | 10/1996 | Lin et al. | ....................... | 514/49 |
| 5,565,438 A | * | 10/1996 | Chu et al. | ..................... | 514/50 |
| 5,567,688 A | * | 10/1996 | Chu et al. | ..................... | 514/46 |
| 5,567,689 A | * | 10/1996 | Sommadossi et al. | ........ | 514/50 |
| 5,587,362 A | * | 12/1996 | Chu et al. | ..................... | 514/46 |
| 5,599,796 A | * | 2/1997 | Schinazi et al. | ............... | 514/44 |
| 5,627,160 A | * | 5/1997 | Lin et al. | ....................... | 514/49 |
| 5,631,239 A | * | 5/1997 | Lin et al. | ....................... | 514/49 |
| 5,672,594 A | * | 9/1997 | Weis et al. | .................... | 514/45 |
| 5,681,947 A | * | 10/1997 | Bergstrom et al. | .......... | 536/28.6 |
| 6,130,326 A | * | 10/2000 | Ramasamy et al. | ......... | 536/28.7 |

OTHER PUBLICATIONS

Van Draanen et al., "Influence of Stereochemistry on Antiviral Activities and Resistance Profiles of Dideoxycytidine Nucleosides," *Antimicrobial Agents and Chemotherapy*, 38(4), 868–871 (Apr. 1994).*

* cited by examiner

Primary Examiner—James O. Wilson
(74) Attorney, Agent, or Firm—Rutan & Tucker, LLP; Robert D. Fish

(57) ABSTRACT

Novel monocyclic L-Nucleoside compounds have the general formula

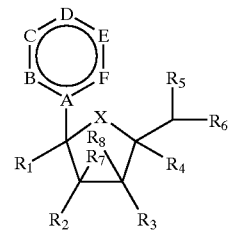

Embodiments of these compounds are contemplated to be useful in treating a wide variety of diseases including infections, infestations, neoplasms, and autoimmune diseases. Viewed in terms of mechanism, embodiments of the novel compounds show immunomodulatory activity, and are expected to be useful in modulating the cytokine pattern, including modulation of Th1 and Th2 response.

5 Claims, 27 Drawing Sheets

Type 1 Cytokines

D-Ribavirin  L-Ribavirin

Type 2 Cytokines

D-Ribavirin      L-Ribavirin

Concentration (μM)

Tam et al: The effect of L-ribavirin on the inflammatory ear response to dinitrofluorobenzene

80  81

82  83

84  85

86

87

88

13

MONOCYCLIC L-NUCLEOSIDES, ANALOGS AND USES THEREOF

This application is a divisional application of co-pending U.S. application Ser. No. 09/969,355, filed Oct. 1, 2001, now U.S. Pat. No. 6,573,248, which is a divisional application of allowed U.S. application Ser. No. 09/633,493, filed Aug. 7, 2000, now U.S. Pat. No. 6,552,183, which is a divisional application of U.S. Pat. No. 6,130,326 filed Apr. 14, 1999, as application Ser. No. 09/291,903, which is a 371, U.S. national phase of PCT/US97/18767 filed on Oct. 15, 1997, which claims the benefit of U.S. provisional application 60/028,585, filed Oct. 16, 1996.

FIELD OF THE INVENTION

The present invention relates to the field of L-nucleosides.

BACKGROUND OF THE INVENTION

The last few decades have seen significant efforts expended in exploring possible uses of D-nucleoside analogs as antiviral agents. Some of this work has borne fruit, and a number of nucleoside analogs are currently being marketed as antiviral drugs, including the HIV reverse transcriptase inhibitors (AZT, ddI, ddC, d4T, and 3TC).

Nucleoside analogs have also been investigated for use as immune system modulators, (Bennet, P. A. et al., *J. Med. Chem.*, 36, 635, 1993), but again with less than completely satisfactory results. For example, guanosine analogs such as 8-bromo-, 8-mercapto-, 7-methyl-8-oxoguanosine (Goodman, M. G. *Immunopharmacology*, 21, 51–68, 1991) and 7-thia-8-oxoguanosine (Nagahara, K. *J. Med. Chem.*, 33, 407–415, 1990; U.S. Pat. No. 5,041,426) have been studied over the years for their ability to activate the immune system. These guanosine derivatives show excellent antiviral and/or antitumor activity in vivo. But, these $C_8$-substituted guanosines were unable to activate T-cells (Sharma, B. S. et al., *Clin. Exp. Metastasis*, 9, 429–439, 1991). The same was found to be true with 6-arylpyrimidinones (Wierenga, W. *Ann. N. Y. Acad. Sci.*, 685, 296–300, 1993). In other research, a series of 3-deazapurine nucleosides were synthesized and evaluated as immuno-modulating agents. U.S. Pat. No. 4,309,419 describes the use of 3-deazaadenosine as being an inhibitor of the immune system. The β-D-nucleoside, β-2'-deoxy-3-deazaguanosine (U.S. Pat. No. 4,950,647) displayed the most potent immunoenhancing potency on activated T-cell response. Antiinflamatory and immunosuppressant activity has also been disclosed for certain 2'-deoxynucleosides (EPO Application 0 038 569). However, these compounds undergo facile in vivo metabolic cleavage of their glycosyl bond, which effectively inactivates their biological potency. Adenosine derivatives disclosed in U.S. Pat. No. 4,148,888 are also catabolized in vivo by deaminase enzymes. In still other research, Levamisole, a thymomimetic immunostimulant (Hadden et al, *Immunol. Today*, 14, 275–280, 1993), appears to act on the T-cell lineage in a manner similar to thymic hormones. Tucaresol (Reitz et al, Nature, 377, 71–75,1995), another T-cell stimulant, is now undergoing clinical trials. More recently, 6-substituted purine linker amino acid (Zacharie et al, J. Med. Che., 40, 2883–2894, 1997) has been described as a promising immunostimulant which may be targeted for those disease states which require an increased CTL or Th1 type response.

One possible target of immunomodulation involves stimulation or suppression of Th1 and Th2 lymphokines. Type I (Th1) cells produce interleukin 2 (IL-2), tumor necrosis factor (TNFα) and interferon gamma (IFN( ) and they are responsible primarily for cell-mediated immunity such as delayed type hypersensitivity and antiviral immunity. Type 2 (Th2) cells produce interleukins, IL4, IL-5, IL-6, IL-9, IL-10 and IL-13 and are primarily involved in assisting humoral immune responses such as those seen in response to allergens, e.g. IgE and IgG4 antibody isotype switching (Mosmann, 1989, *Annu Rev Immunol*, 7:145–173). D-guanosine analogs have been shown to elicit various effects on lymphokines IL-1, IL-6, IFNα and TNFα (indirectly) in vitro (Goodman, 1988, *Int J Immunopharmacol*, 10, 579–88) and in vivo (Smee et al., 1991, *Antiviral Res* 15: 229). However, the ability of the D-guanosine analogs such as 7-thio-8-oxoguanosine to modulate Type I or Type 2 cytokines directly in T cells was ineffective or has not been described.

Significantly, most of the small molecule research has focused on the synthesis and evaluation of D-nucleosides. This includes Ribavirin (Witkowski, J. T. et al., *J. Med. Chem.*, 15, 1150, 1972), AZT (De Clercq, E. *Adv. Drug Res.*, 17, 1, 1988), DDI (Yarchoan, R. et al., *Science* (Washington, D.C.), 245, 412, 1989), DDC (Mitsuya, H. et al., *Proc. Natl. Acad. Sci. U. S. A.*, 83, 1911, 1986), d4T (Mansuri, M. M. et al., *J. Med. Chem.*, 32, 461, 1989) and 3TC (Doong, S. L. et al., *Proc. Natl. Acad. Sci. U.S.A.*, 88, 8495–8599, 1991). In this handful of therapeutic agents, only 3TC which contains an unnatural modified L-ribose moiety, the enantiomer of natural D-ribose.

After the approval of 3TC by the FDA, a number of nucleosides with the unnatural L-configuration were reported as having potent chemotherapeutic agents against immunodeficiency virus (HIV), hepatitis B virus (HBV), and certain forms of cancer. These include (−)-β-L-1-[2-(hydroxymethyl)-1,3-oxathiolan-4-yl]-5-fluorocytosine (FTC; Furman, P. A., et al, *Antimicrob. Agents Chemother.*, 36, 2686–2692, 1992), (−)-β-L-2',3'-dideoxypentofuranosyl-5-flurocytosine (L-FddC; Gosselin, G., et al, *Antimicrob. Agents Chemother.*, 38, 1292–1297, 1994), (−)-β-L-1-[2-(hydroxymethyl)-1,3-oxathiolan-4-yl] cytosine [(−)-OddC; Grove, K. L., et al, *Cancer Res.*, 55, 3008–3011, 1995], 2',3'-dideoxy-β-L-cystidine (β-L-ddC; Lin, T. S., et al, *J. Med. Chem.*, 37, 798–803, 1994), 2'fluoro-5-methyl-β-L-arabinofuranosyluracil (L-FMAU; U.S. Pat. No. 5,567,688), 2',3'-dideoxy-2',3'-didehydro-β-L-cystidine (β-L-d4C; Lin, T. S., et al, *J. Med. Chem.*, 39, 1757–1759, 1996), 2',3'-dideoxy-2',3'-didehydro-β-L-5-fluorocystidine (β-L-Fd4C; Lin, T. S., et al, *J. Med. Chem.*, 39, 1757–1759, 1996), L-cyclopentyl carbocyclic nucleosides (Wang, P., et al, *Tetrahedron Letts.*, 38, 4207–4210, 1997) and variety of 9-(2'-deoxy-2'-fluoro-β-L-arabinofuranosyl)purine nucleosides (Ma, T.' et al, *J. Med. Chem.*, 40, 2750–2754, 1997).

Other research on L-nucleosides has also been reported. U.S. Pat. No. 5,009,698, for example, describes the synthesis and use of L-adenosine to stimulate the growth of a plant. WO 92/08727 describes certain L-2'-deoxyuridines and their use for treating viruses. Spadari, S., et al, *J. Med. Chem.*, 35, 4214–4220, 1992, describes the synthesis of certain L-β-nucleosides useful for treating viral infections including Herpes Simplex Virus Type I. U.S. Pat. No. 5,559,101 describes the synthesis of α- and β-L-ribofuranosyl nucleosides, processes for their preparation, pharmaceutical composition containing them, and method of using them to treat various diseases in mammals. A German patent (De 195 18 216) describes the synthesis of 2'-fluoro-2'-deoxy-L-β-arabinofuranosyl pyrimidine nucleosides. U.S. Pat. Nos. 5,565,438 and 5,567,688 describe the synthesis and utility of L-FMAU. WO Patent 95/20595 describes the synthesis of 2'-deoxy-2'-fluoro-L-3-arbinofuranosyl purine and pyrimidine nucleosides and method of treating HBV or EBV. U.S. Pat. No. 5,567,689 describes methods for increasing uridine levels with L-nucleosides. WO patent 96/28170 describes a method of reducing the toxicity of D-nucleosides by co-administering an effective amount of L-nucleoside compounds.

Significantly, while some of the known L-nucleosides have shown potent antiviral activity with lower toxicity profiles than their D-counterparts, none of these L-nucleoside compounds have been shown to posses immunomodulatory properties. Moreover, at present there is no effective treatment for the modulation of the immune system where lymphokine profiles (Th1 and Th2 subsets) have been implicated. Thus, there remains a need for novel L-nucleoside analogs, especially a need for L-nucleoside analogs which modulate the immune system, and most especially L-nucleoside analogs which specifically modulate Th1 and Th2.

BRIEF DESCRIPTION OF THE INVENTION

The present invention is directed to novel L-nucleoside compounds, their therapeutic uses and synthesis.

In one aspect of the invention, novel L-nucleoside compounds are provided according to the following formula:

Formula I

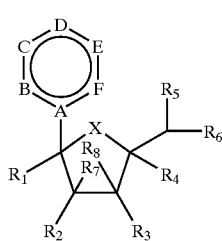

wherein:

A is independently selected from N or C;

B, C, E, F are independently selected from CH, CO, N, S, Se, O, $NR^1$, $CCONH_2$, $CCH_3$, C—$R^2$ or P; $R^1$ is independently H, lower alkyl, lower alkylamines, $COCH_3$, lower alkyl alkenyl, lower alkyl vinyl or lower alkyl aryls. $R^2$ is independently H, OH, halogens, CN, $N_3$, $NH_2$, C(=O)$NH_2$, C(=S)$NH_2$, C(=NH)$NH_2$.HCl, C(=NOH)$NH_2$, C(=NH)OMe, lower alkyl, lower alkylamines, lower alkyl alkenyl, lower alkyl vinyl, lower alkyl aryls or substituted heterocycles;

D is independently selected from CH, CO, N, S, Se, O, $NR^1$, $CCONH_2$, $CCH_3$, C—$R^2$, P or nothing, where $R^1$ is independently H, O, lower alkyl, lower alkylamines, $COCH_3$, lower alkyl alkenyl, lower alkyl vinyl or lower alkyl aryls, and $R^2$ is independently H, OH, halogens, CN, $N_3$, $NH_2$, lower alkyl, lower alkylamines, lower alkyl alkenyl, lower alkyl vinyl, lower alkyl aryls or substituted heterocycles;

X is independently O, S, $CH_2$ or NR; where R is $COCH_3$;

$R_1$ and $R_4$ are independently selected from H, CN, $N_3$, $CH_2OH$, lower alkyl and lower alkyl amines;

$R_2$, $R_3$, $R_5$, $R_6$, $R_7$ and $R_8$, are independently selected from H, OH, CN, $N_3$, halogens, $CH_2OH$, $NH_2$, $OCH_3$, $NHCH_3$, $ONHCH_3$, $SCH_3$, SPh, alkenyl, lower alkyl, lower alkyl amines and substituted heterocycles; and $R_1$, $R_2$, $R_3$, $R_4$, $R_5$, $R_6$, $R_7$ and $R_8$ are not all substituted at the same time; such that when $R_2$=$R_3$=H, then $R_7$ and $R_8$ are hydrogens or nothing;

when $R_1$, $R_4$ or $R_5$ are substituted, then $R_7$=$R_8$=H and $R_2$=$R_3$=OH;

when $R_2$ or $R_3$ are substituted, then $R_7$ and $R_8$ are H or OH;

when $R_7$ or $R_8$ are substituted, then $R_2$ and $R_3$ are H or OH;

when $R_7$ and $R_8$ are hydroxyl, then $R_2$ and $R_3$ are not OH;

when A=N; B=CO; C=N or NH; D=CO or C—$NH_2$; E is CH or C-substituted; F=CH; X=O, S or $CH_2$, then $R_2$ will not be H, OH, $CH_3$, halogens, $N_3$, CN, SH, SPh, $CH_2OH$, $CH_2OCH_3$, $CH_2SH$, $CH_2F$, $CH_2N_3$, aryl, aryloxy or heterocycles;

when A=N; B=CO; C=N or NH; D=CO or C—$NH_2$; E is CH, C—$CH_3$ or halogen; F=CH; X=N—$COCH_3$, then $R_2$ will not be H or OH;

when A=N; B=CH; C=CH or $CH_3$; D=CH or C—$CH_3$; E is CH, C—$CH_3$ or C—$CONH_2$; F=CH; X=O, or $CH_2$, then $R_2$ will not be H or OH;

when A=N; B=N, CO or CH; C=CH, C—Cl or C—$OCH_3$; D=CH or C—Ph; E is CH, C—Cl or C—Ph; F=N or CO; X=O, then $R_2$ will not be H or OH;

when A=N; B=CO or CS; C=N or NH; D=CO or C—$NH_2$; E is CH or N; F=N or CH; X=O, then $R_2$ will not be H or OH; and when A=C; B=CH; C=NH; D=CO, CS or C—$NH_2$; E is N or NH; F=CO or CH; X=O, then $R_2$ will not be H or OH.

In one class of preferred embodiments of the invention, the compound comprises a ribofuranosyl moiety, and in a particularly preferred embodiment the compound comprises L-Ribavirin.

In another aspect of the invention, a pharmaceutical composition comprises a therapeutically effective amount of a compound of Formulas 1 and 3–5, or a pharmaceutically acceptable ester or salt thereof admixed with at least one pharmaceutically acceptable carrier.

In yet another aspect of the invention, a compound according to Formulas 1 and 3–5 is used in the treatment of any condition which responds positively to administration of the compound, and according to any formulation and protocol which achieves the positive response. Among other things it is contemplated that compounds of Formula I may be used to treat an infection, an infestation, a cancer or tumor or an autoimmune disease.

DETAILED DESCRIPTION

Figure 1:
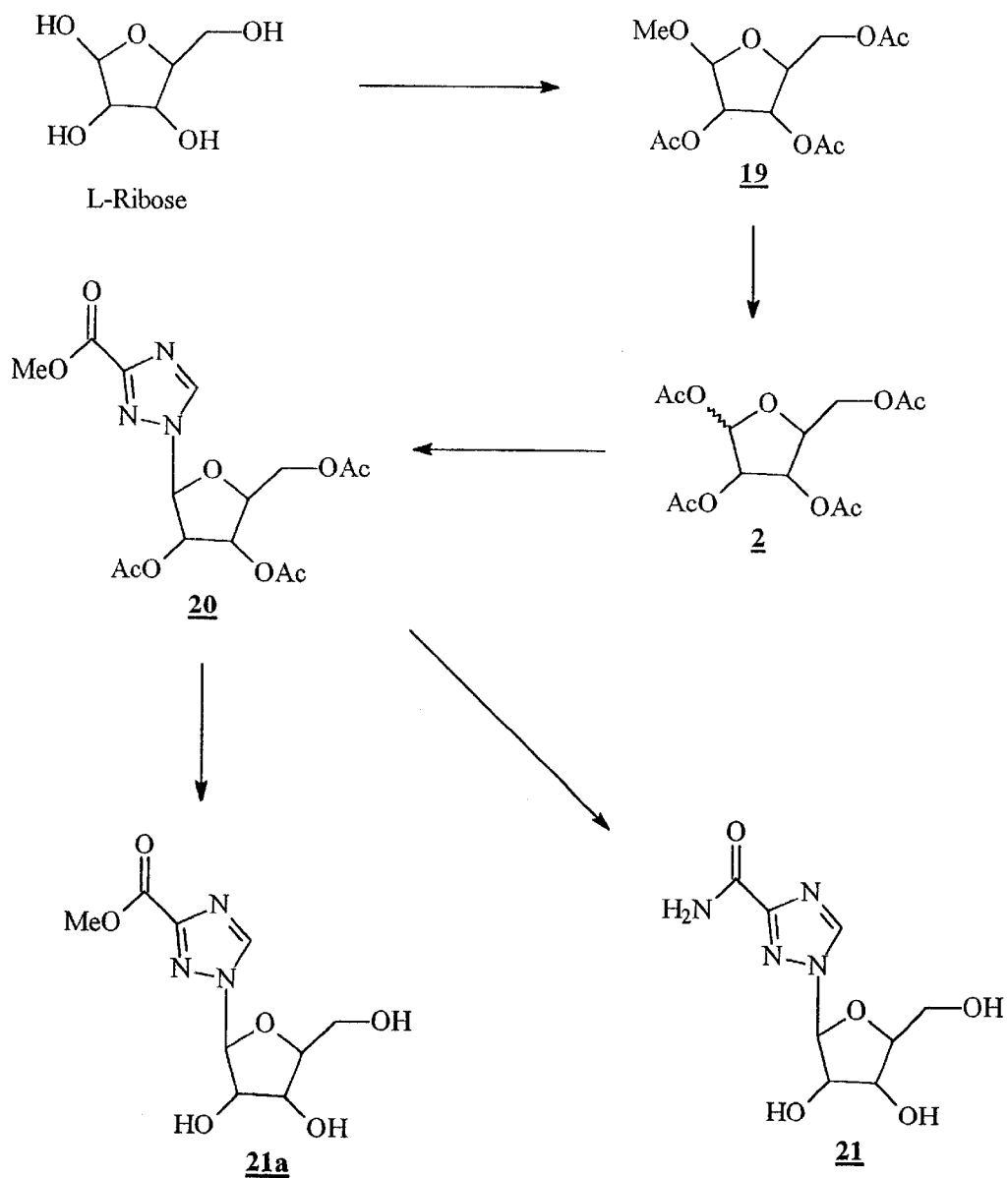
FIGS. 1–12 are schematic representations of synthetic chemical steps which may be used to prepare compounds in the examples section below.
Figure 2:
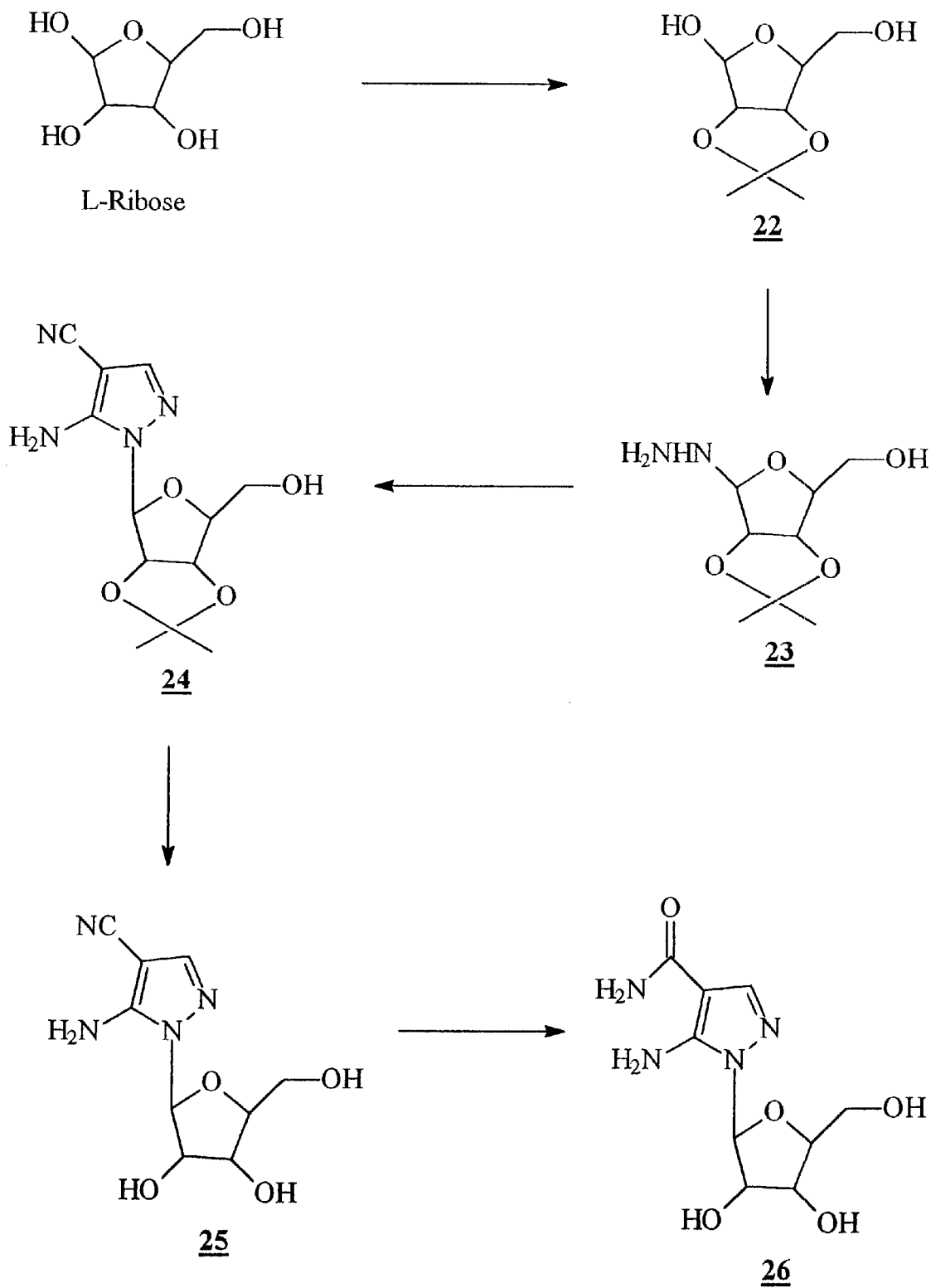
Figure 3:
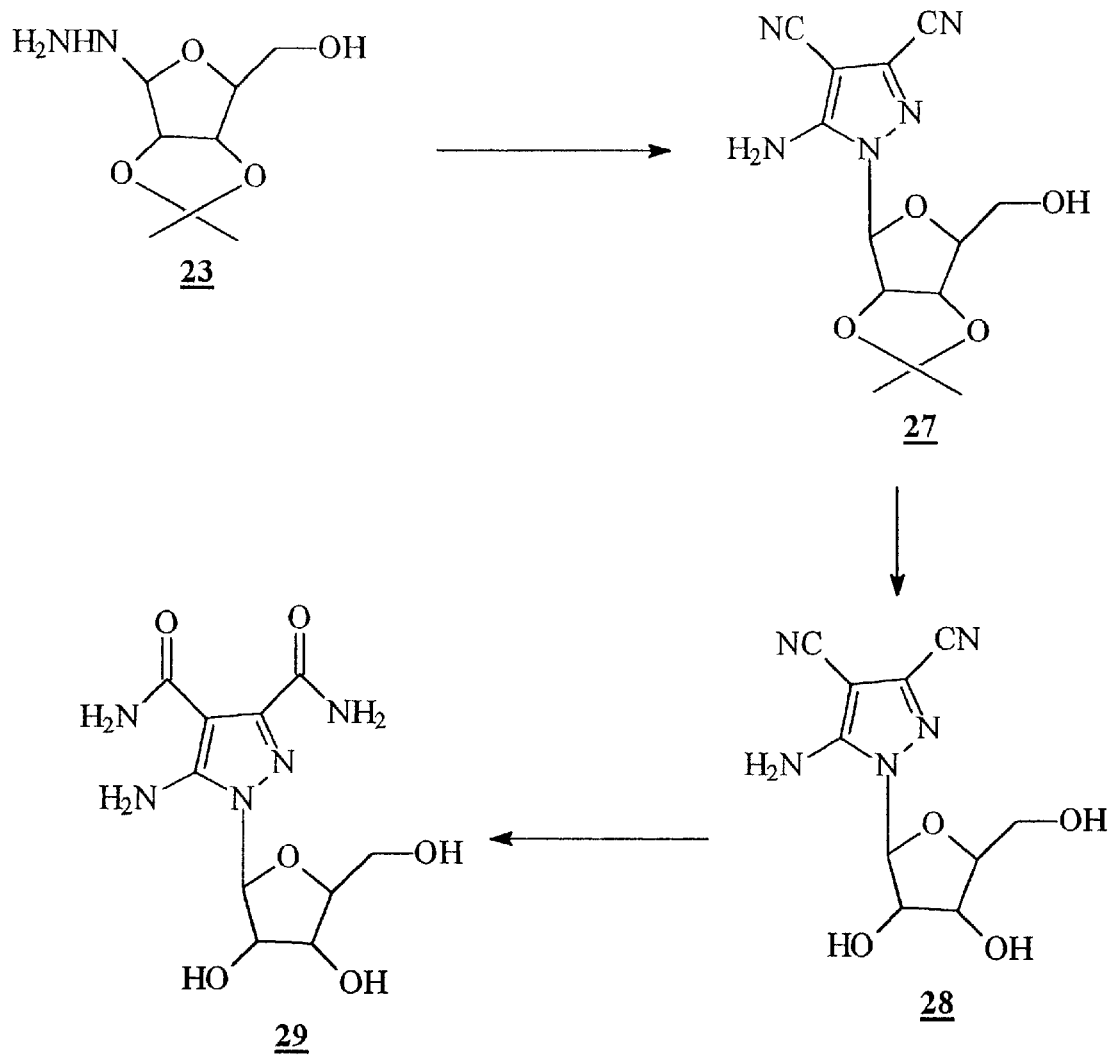
Figure 4:
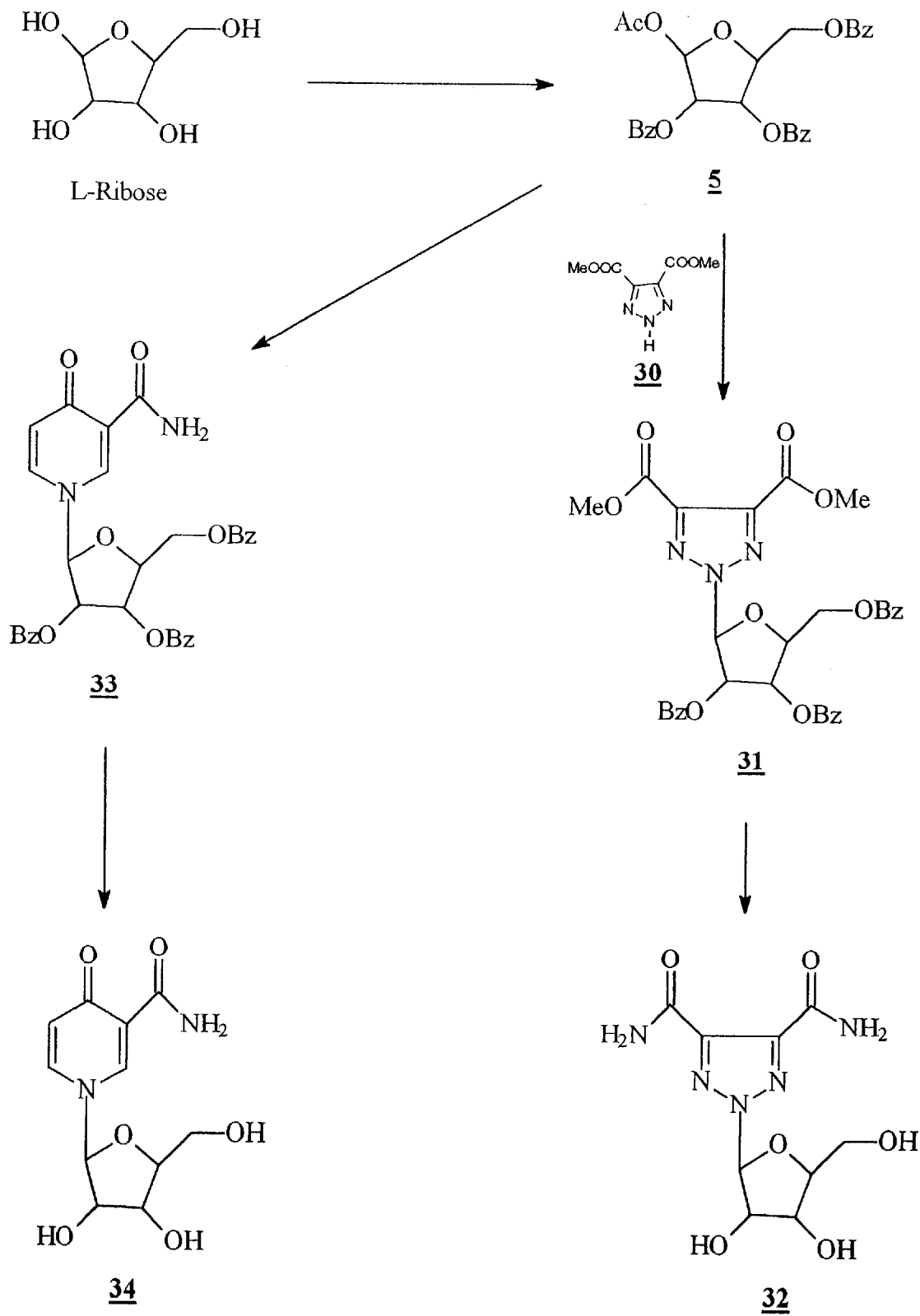
Figure 5:
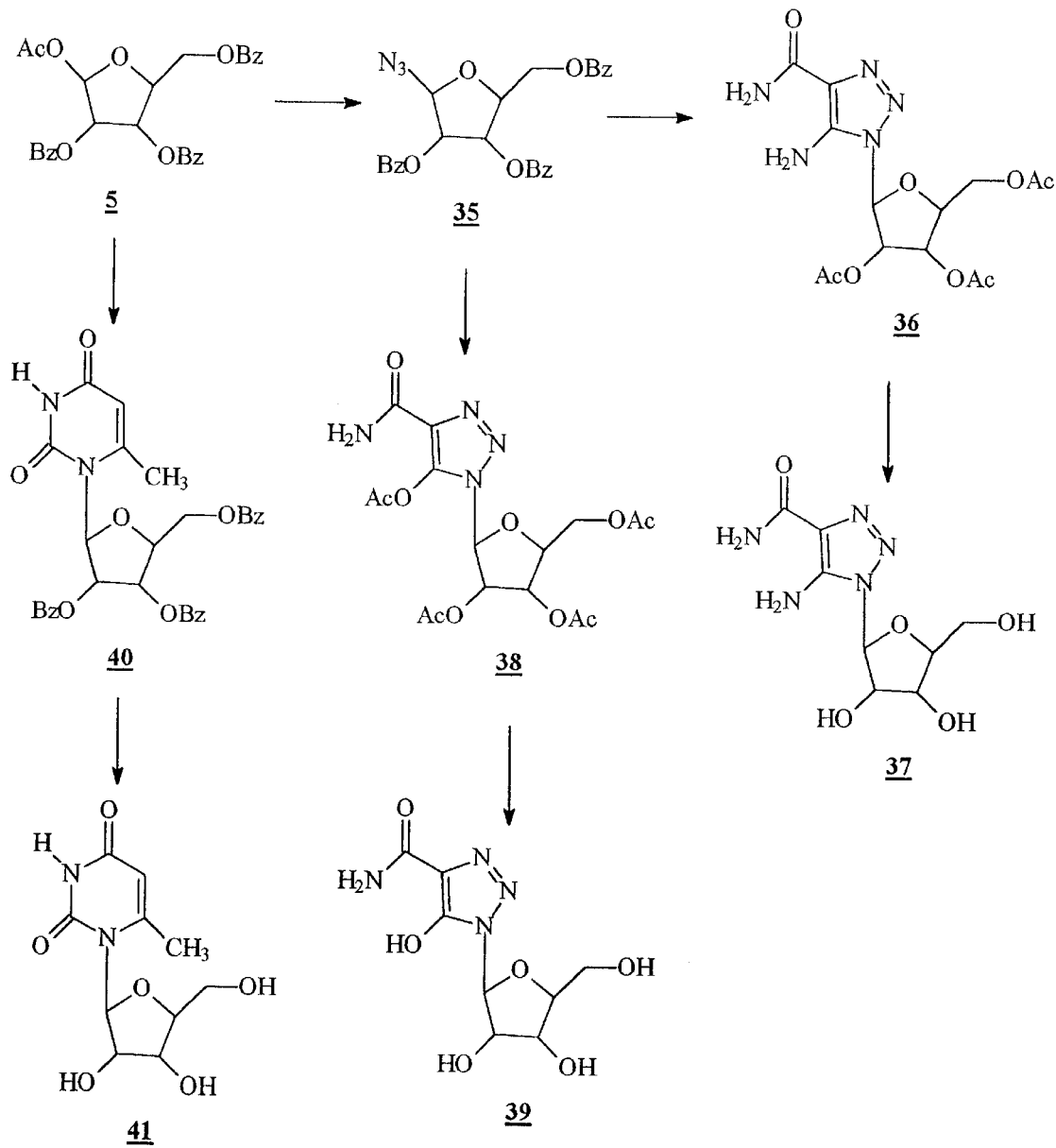
Figure 6:
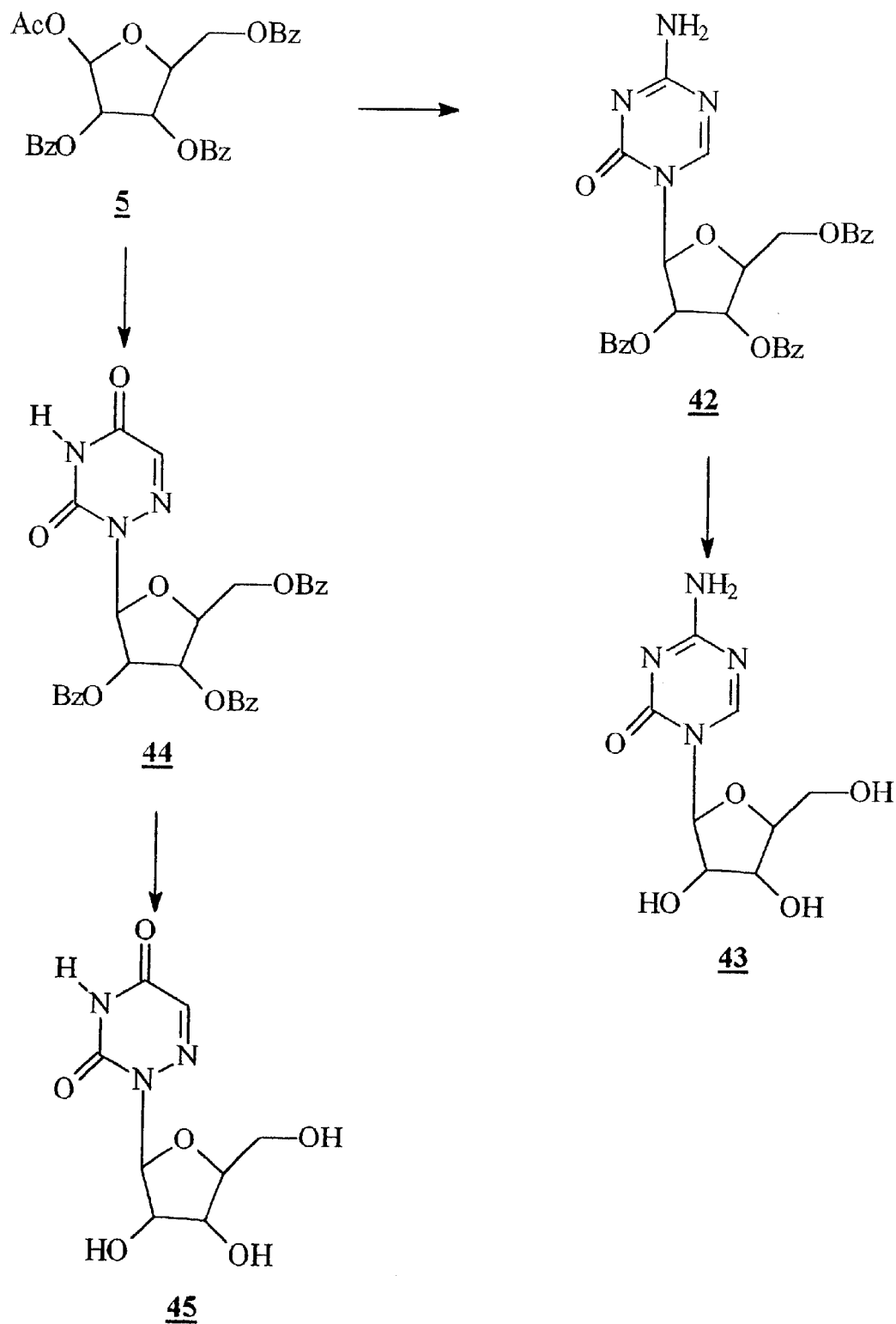
Figure 7:
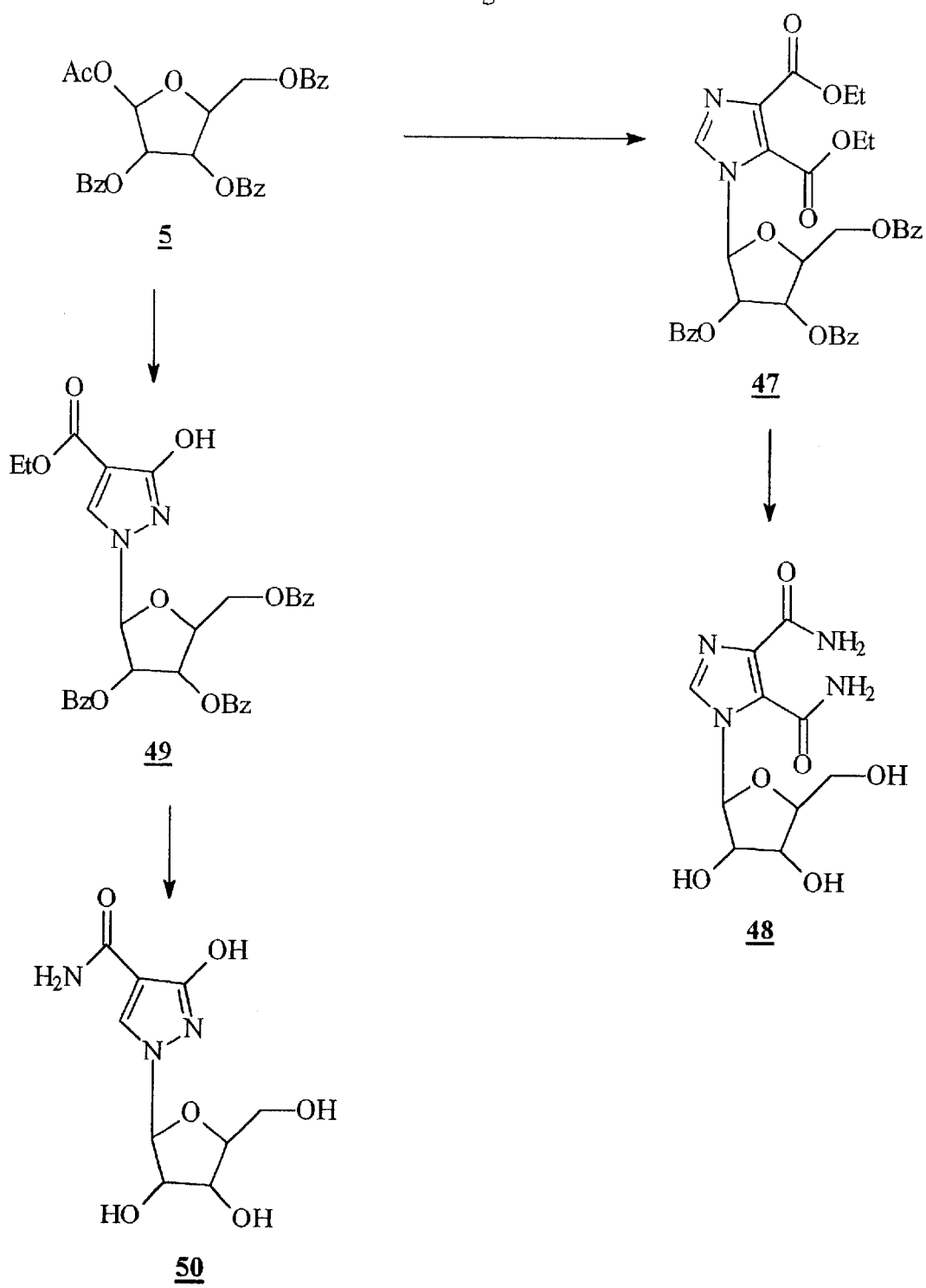
Figure 8:
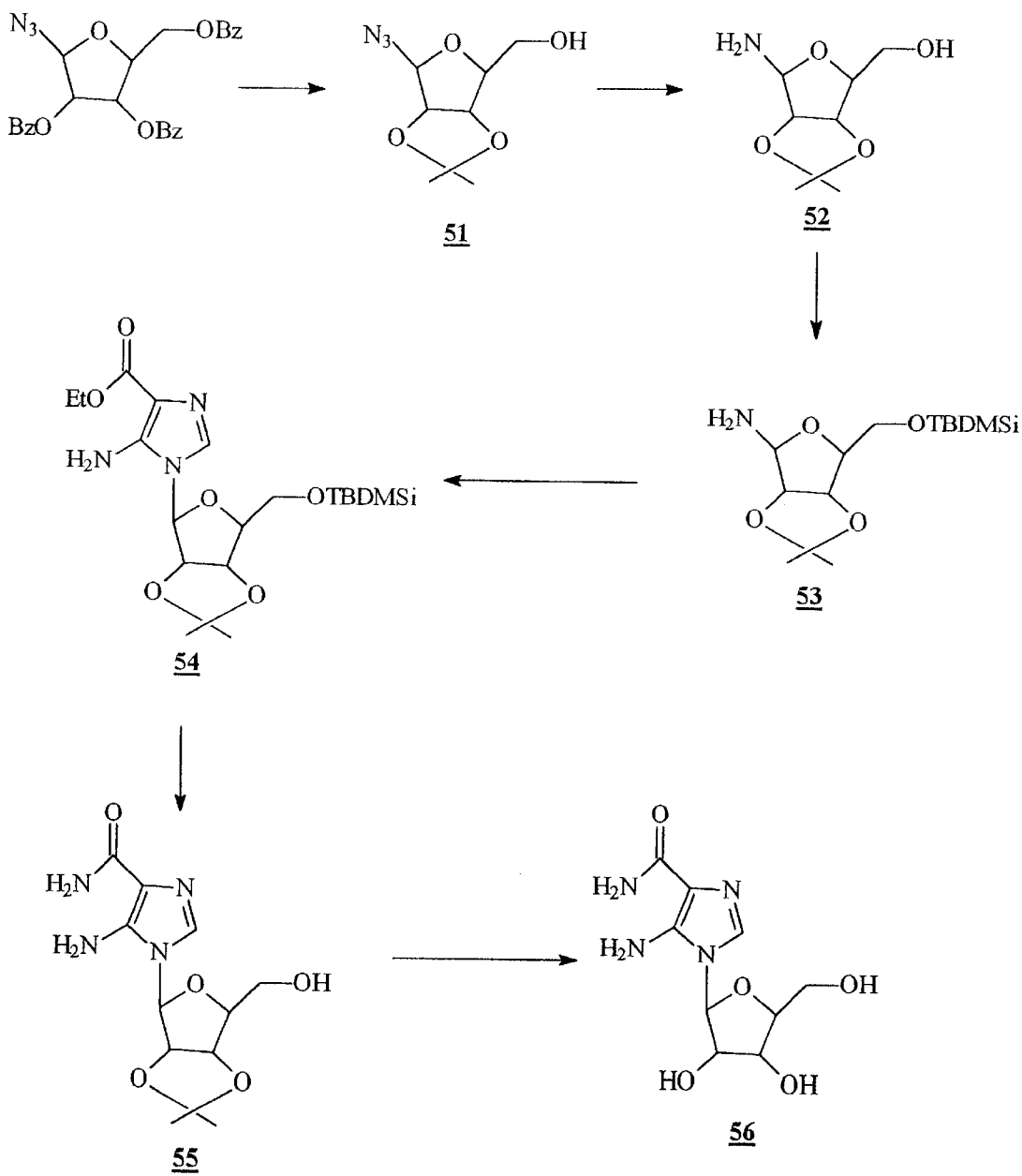
Figure 9:
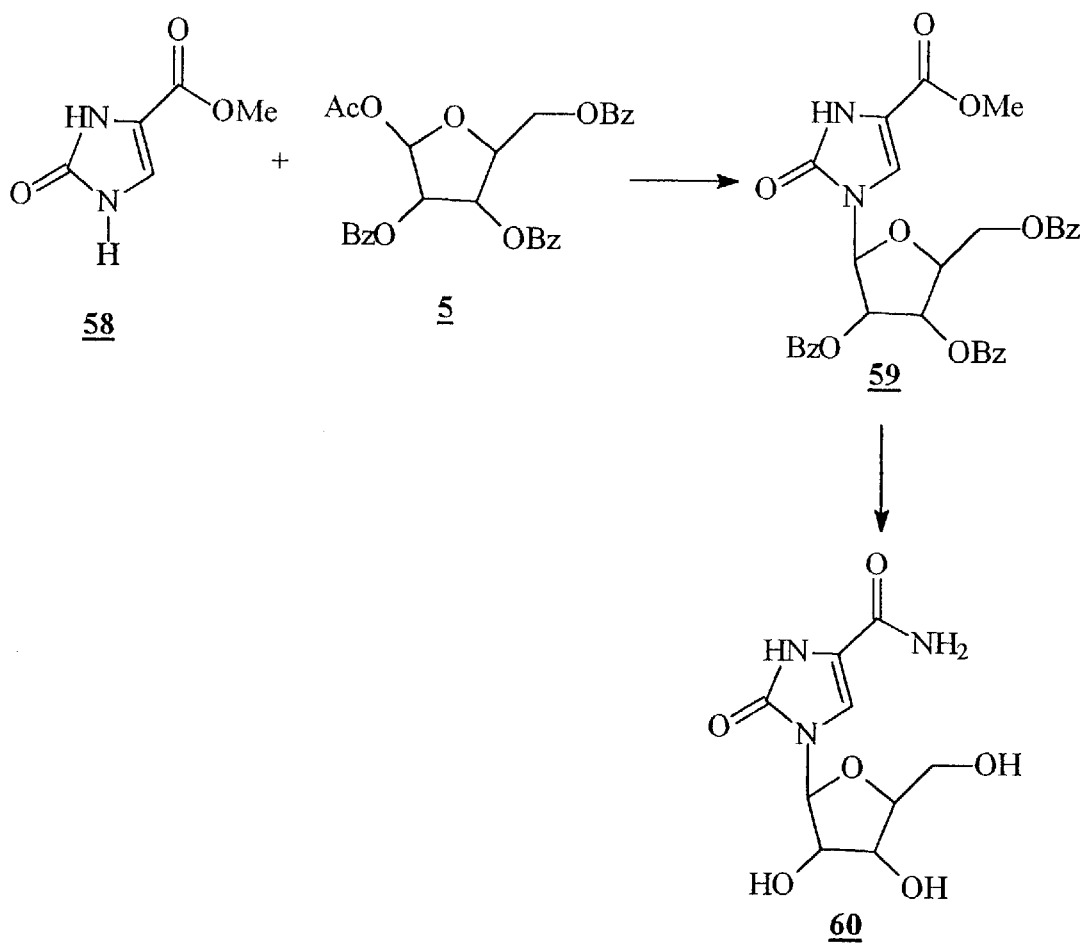
Figure 10:
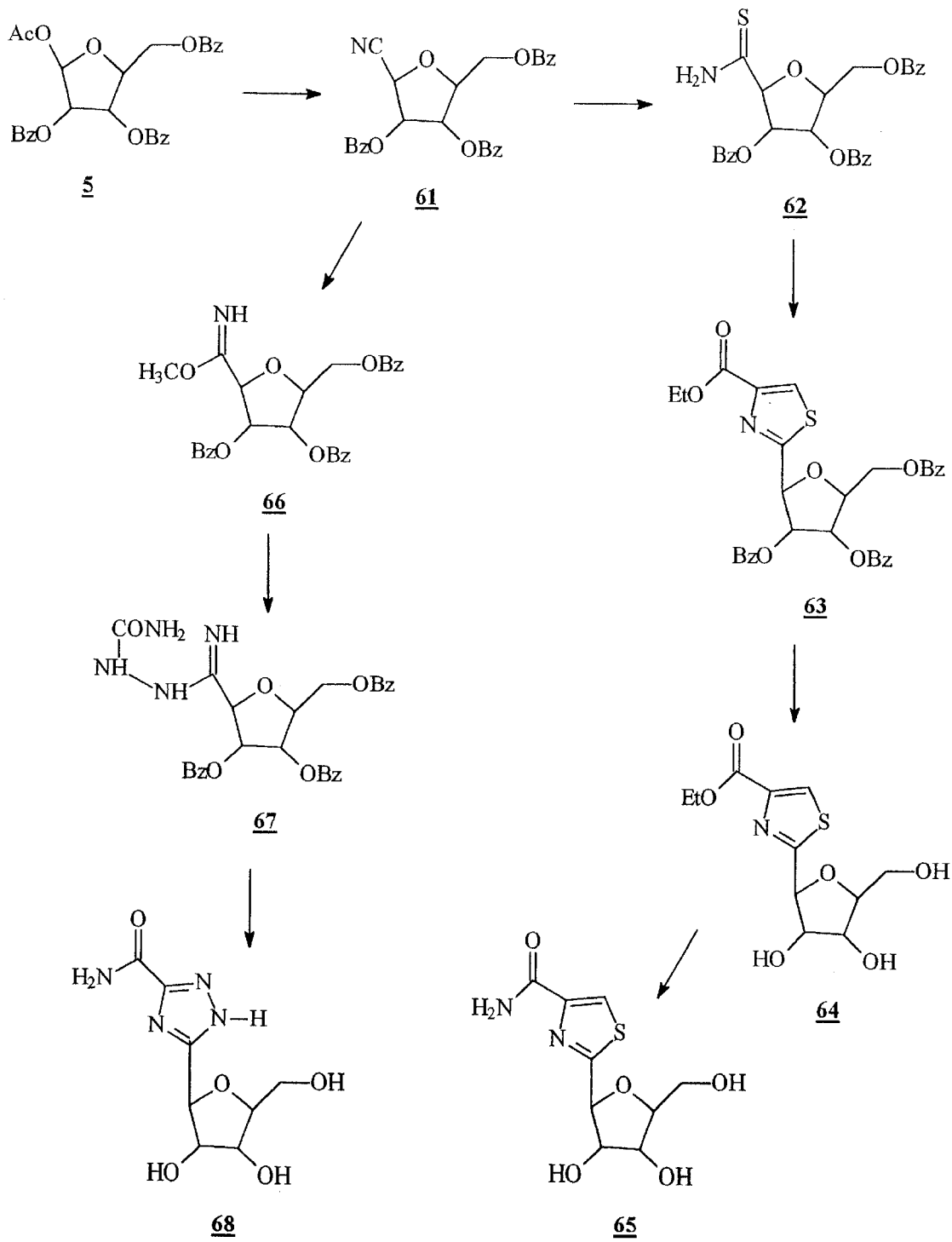
Figure 11:
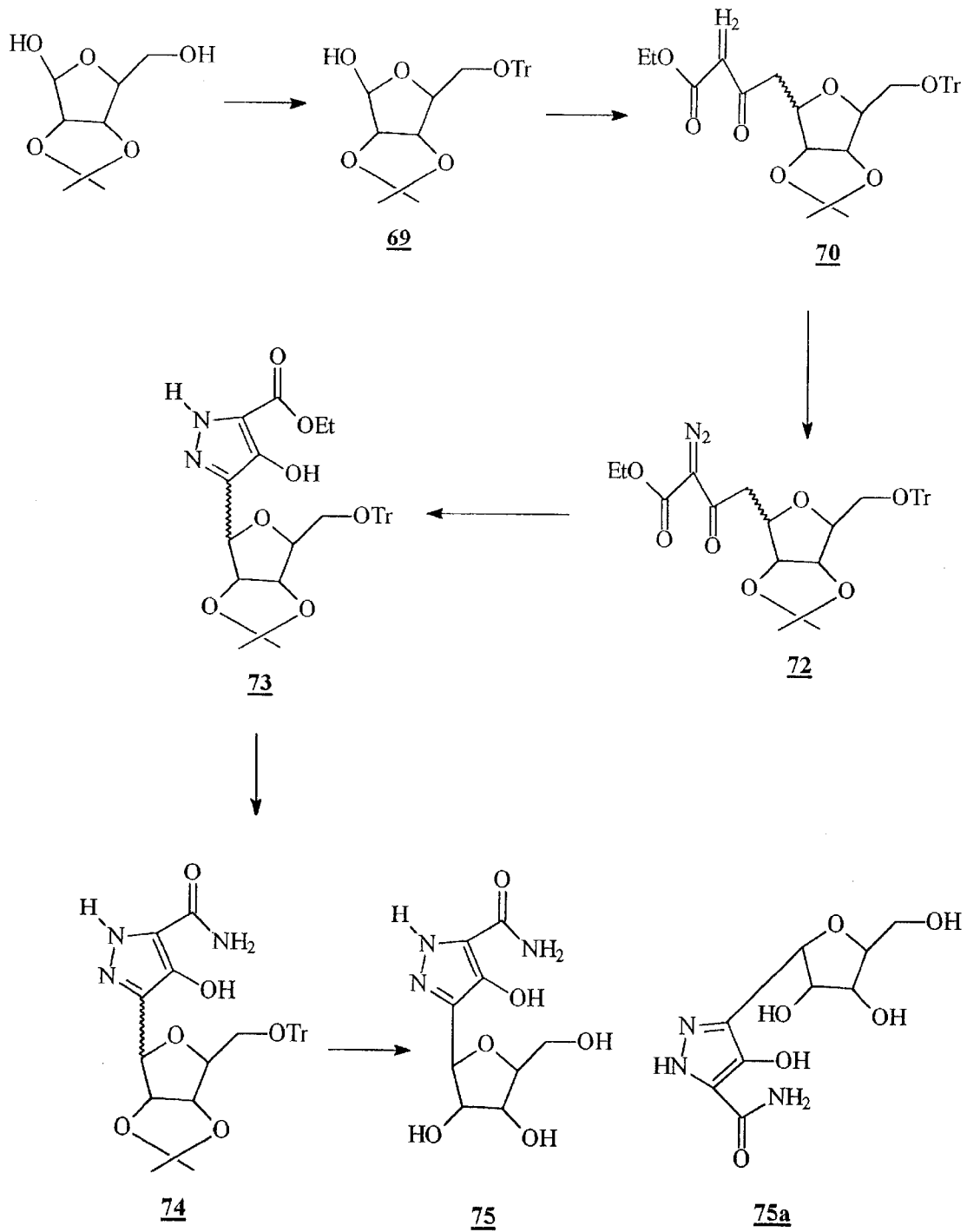
Figure 12:
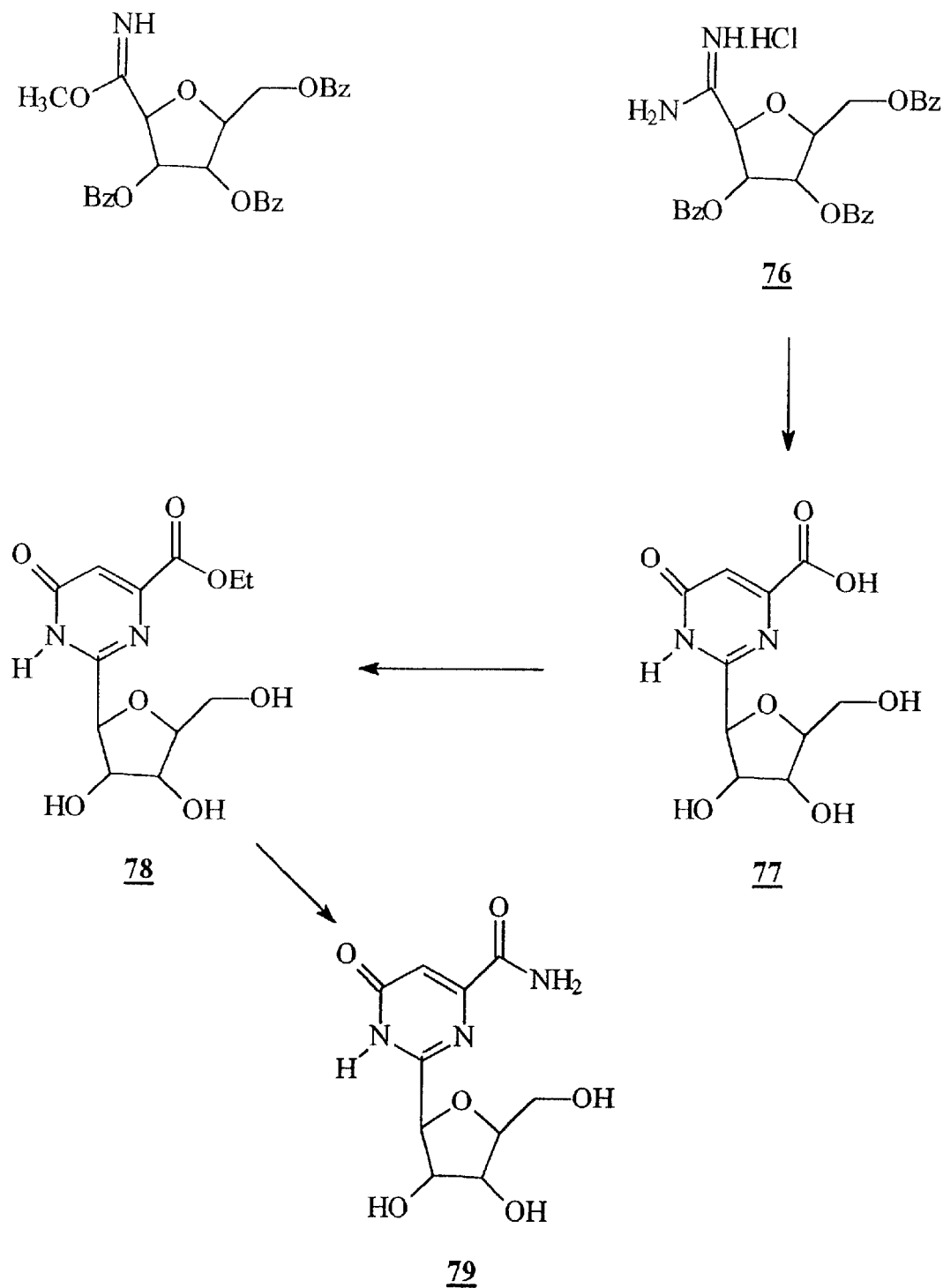

Where the following terms are used in this specification, they are used as defined below.

The term "nucleoside" refers to a compound composed of any pentose or modified pentose moiety attached to a specific position of a heterocycle or to the natural position of a purine (9-position) or pyrimidine (1-position) or to the equivalent position in an analog.

The term "nucleotide" refers to a phosphate ester substituted on the 5'-position of a nucleoside.

The term "heterocycle" refers to a monovalent saturated or unsaturated carbocyclic radical having at least one hetero atom, such as N, O or S, within the ring each available position of which can be optionally substituted, independently, with, e.g., hydroxy, oxo, amino, imino, lower alkyl, bromo, chloro and/or cyano. Included within this class of substituents are purines, pyrimidines.

The term "purine" refers to nitrogenous bicyclic heterocycles.

The term "pyrimidine" refers to nitrogenous monocyclic heterocycles.

The term "D-nucleosides" that is used in the present invention describes to the nucleoside compounds that have a D-ribose sugar moiety (e.g., Adenosine).

The term "L-nucleosides" that is used in the present invention describes to the nucleoside compounds that have an L-ribose sugar moiety.

The term "L-configuration" is used throughout the present invention to describe the chemical configuration of the ribofuranosyl moiety of the compounds that is linked to the nucleobases. The L-configuration of the sugar moiety of compounds of the present invention contrasts with the D-configuration of ribose sugar moieties of the naturally occurring nucleosides such as cytidine, adenosine, thymidine, guanosine and uridine.

The term "C-nucleosides" is used throughout the specification to describe the linkage type that formed between the ribose sugar moiety and the heterocyclic base. In C-nucleosides, the linkage originates from the C-1 position of the ribose sugar moiety and joins the carbon of the heterocyclic base. The linkage that forms in C-nucleosides are carbon to carbon type.

The term "N-nucleosides" is used throughout the specification to describe the linkage type that formed between the ribose sugar moiety and the heterocyclic base. In N-nucleosides, the linkage originates from the C-1 position of the ribose sugar moiety and joins the nitrogen of the heterocyclic base. The linkage that forms in N-nucleosides are carbon to nitrogen type.

The term "protecting group" refers to a chemical group that is added to, oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

The term "lower alkyl" refers to methyl, ethyl, n-propyl, isopropyl, n-butyl, t-butyl, i-butyl or n-hexyl. This term is further exemplified to a cyclic, branched or straight chain from one to six carbon atoms.

The term "aryl" refers to a monovalent unsaturated aromatic carbocyclic radical having a single ring (e.g., phenyl) or two condensed rings (e.g., naphthyl), which can optionally be substituted with hydroxyl, lower alky, chloro, and/or cyano.

The term "heterocycle" refers to a monovalent saturated or unsaturated carbocyclic radical having at least one hetero atom, such as N, O, S, Se or P, within the ring, each available position of which can be optionally substituted or unsubstituted, independently, with e.g., hydroxy, oxo, amino, imino, lower alkyl, bromo, chloro, and/or cyano.

The term "monocyclic" refers to a monovalent saturated carbocyclic radical having at least one hetero atom, such as ON, S, Se or P, within the ring, each available position of which can be optionally substituted, independently, with a sugar moiety or any other groups like bromo, chloro and/or cyano, so that the monocyclic ring system eventually aromatized [e.g., Thymidine; 1-(2'-deoxy-∃-D-erythro-pentofuranosyl)thymine].

The term "immunomodulators" refers to natural or synthetic products capable of modifying the normal or aberrant immune system through stimulation or suppression.

The term "effective amount" refers to the amount of a compound of formula (I) which will restore immune function to normal levels, or increase immune function above normal levels in order to eliminate infection.

The compounds of Formula I may have multiple asymmetric centers. Accordingly, they may be prepared in either optically active form or as a racemic mixture. The scope of the invention as described and claimed encompasses the individual optical isomers and non-racemic mixtures thereof as well as the racemic forms of the compounds of Formula I.

The terms "∀" and "∃" indicate the specific stereochemical configuration of a substituent at an asymmetric carbon atom in a chemical structure as drawn. The compounds described herein are all in the L-furanosyl configuration.

The term "enantiomers" refers to a pair of stereoisomers that are non-superimposable mirror images of each other. A mixture of a pair of enantiomers, in a 1:1 ratio, is a "racemic" mixture.

The term "isomers" refers to different compounds that have the same formula. "Stereoisomers" are isomers that differ only in the way the atoms are arranged in space.

A "pharmaceutically acceptable salts" may be any salts derived from inorganic and organic acids or bases.

Compounds of the present invention are named according to the convention of Formula II:

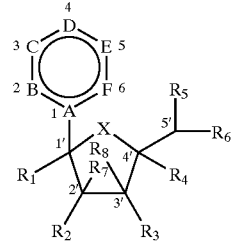

Formula II

Compounds

The compounds of the present invention are generally described by Formula I. There are, however, several subsets of compounds which are of particular interest, including compounds according to Formulas III, IV and V below.

Compounds according to Formula III have the following structure:

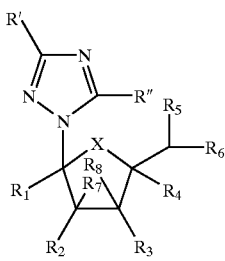

Formula III wherein:
X is independently O, S, CH$_2$ and NR, where R is COCH$_3$;
R' and R" are independently selected from H, CN, C(=O)NH$_2$, NH$_2$, C(=S)NH$_2$, C(=NH)NH$_2$.HCl, C(=NOH)NH$_2$, C(=NH)OMe, heterocycles, halogens, lower alkyl or lower alkyl aryl;
R$_1$ and R$_4$ are independently selected from H, CN, N$_3$, CH$_2$OH, lower alkyl or lower alkyl amines; and
R$_2$, R$_3$, R$_5$, R$_6$, R$_7$ and R$_8$ are independently selected from H, OH, CN, N$_3$, halogens, CH$_2$OH, NH$_2$, OCH$_3$, NHCH$_3$, ONHCH$_3$, SCH$_3$, SPh, alkenyl, lower alkyl, lower alkyl amines or substituted heterocycles; such that
when R$_2$=R$_3$=H, then R$_7$ and R$_8$ are hydrogens or nothing.

In compounds of Formula III, R' preferably carboxamide or CN and R" is hydrogen or halogens; R$_1$=R$_4$=R$_5$=R$_7$=R$_8$=H and R$_2$=R$_3$=OH, and preferably X is oxygen.

Compounds according to Formula IV have the following structure:

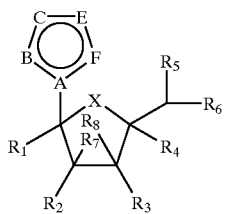

Formula IV wherein:
A is independently selected from N or C;
B, C, E and F are independently selected from CH, CO, N, S, Se, O, NR$^1$, CCONH$_2$, CCH$_3$, C—R$^2$ or P; R$^1$ is independently H, lower alkyl, lower alkylamines, COCH$_3$, lower alkyl alkenyl, lower alkyl vinyl or lower alkyl aryls. R$^2$ is independently H, OH, halogens, CN, N$_3$, NH$_2$, C(=O)NH$_2$, C(=S)NH$_2$, C(=NH)NH$_2$.HCl, C(=NOH)NH$_2$, C(=NH)OMe, lower alkyl, lower alkylamines, lower alkyl alkenyl, lower alkyl vinyl, lower alkyl aryls or substituted heterocycles;
X is independently O, S, CH$_2$ or NR; where R is COCH$_3$;
R$_1$ and R$_4$ are independently selected from H, CN, N$_3$, CH$_2$OH, lower alkyl or lower alkyl amines; and
R$_2$, R$_3$, R$_5$, R$_6$, R$_7$ and R$_8$ are independently selected from H, OH, CN, N$_3$, halogens, NH$_2$, CH$_2$OH, OCH$_3$, NHCH$_3$, ONHCH$_3$, SCH$_3$, SPh, alkenyl, allyl, lower alkyl, lower alkyl amines or substituted heterocycles; such that
when R$_2$=R$_3$=H, then R$_7$ and R$_8$ are hydrogens or nothing;
when A is carbon; B=E=N; C is N—Ph, then F is not CH;
when A=N; C is CH; B=E=C—CH$_3$, then F is not nitrogen; and
when A is carbon, B=N; C=C—CONH$_2$; E=CH; F=S, then X is not CH$_2$.

In compounds of Formula IV, R$^1$ is preferably H, lower alkyl or allyl; R$^2$ is preferably H, OH, halogens, CN, N$_3$, NH$_2$, C(=O)NH$_2$, C(=S)NH$_2$, C(=NH)NH$_2$.HCl, C(=NOH)NH$_2$ or C(=NH)OMe; and when R$_1$=R$_4$=R$_5$=R$_7$=R$_8$=H, then preferably R$_2$=R$_3$=OH and preferably X is oxygen.

Compounds according to Formula V have the following structure:

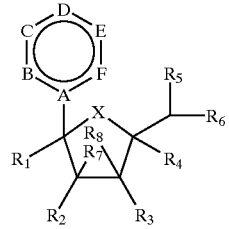

Formula V wherein:
A is independently selected from N or C;
B, C, E, F are independently selected from CH, CO, N, S, Se, O, NR$^1$, CCONH$_2$, CCH$_3$, C—R$^2$ or P; R$^1$ is independently H, lower alkyl, lower alkylamines, COCH$_3$, lower alkyl alkenyl, lower alkyl vinyl or lower alkyl aryls. R$^2$ is independently H, OH, halogens, CN, N$_3$, NH$_2$, C(=O)NH$_2$, C(=S)NH$_2$, C(=NH)NH$_2$.HCl, C(=NOH)NH$_2$, C(=NH)OMe, lower alkyl, lower alkylamines, lower alkyl alkenyl, lower alkyl vinyl, lower alkyl aryls or substituted heterocycles;
D is independently selected from CH, CO, N, S, Se, O, NR$^1$, CCONH$_2$, CCH$_3$, C—R$^2$, P or nothing; R$^1$ is independently H, O, lower alkyl, lower alkylamines, COCH$_3$, lower alkyl alkenyl, lower alkyl vinyl or lower alkyl aryls. R$^2$ is independently H, OH, halogens, CN, N$_3$, NH$_2$, lower alkyl, lower alkylamines, lower alkyl alkenyl, lower alkyl vinyl, lower alkyl aryls or substituted heterocycles;
X is independently O, S, CH$_2$ or NR where R is COCH$_3$;
R$_1$ and R$_4$ are independently selected from H, CN, N$_3$, CH$_2$OH, lower alkyl and lower alkyl amines; and
R$_2$, R$_3$, R$_5$, R$_6$, R$_7$ and R$_8$ are independently selected from H, OH, CN, N$_3$, halogens, CH$_2$OH, NH$_2$, OCH$_3$, NHCH$_3$, ONHCH$_3$, SCH$_3$, SPh, alkenyl, lower alkyl, lower alkyl amines and substituted heterocycles; such that
when R$_2$=R$_3$=H, then R$_7$ and R$_8$ are hydrogens or nothing.
when A=N; B=CO; C=N or NH; D=CO or C—NH$_2$; E is CH or C-substituted; F=CH; X=O, S or CH$_2$, then R$_2$ will not be H, OH, CH$_3$, halogens, N$_3$, CN, SH, SPh, CH$_2$OH, CH$_2$OCH$_3$, CH$_2$SH, CH$_2$F, CH$_2$N$_3$, aryl, aryloxy or heterocycles.
when A=N; B=CO; C=N or NH; D=CO or C—NH$_2$; E is CH, C—CH$_3$ or halogen; F=CH; X=N—COCH$_3$, then R$_2$ will not be H or OH;
when A=N; B=CH; C=CH or CH$_3$; D=CH or C—CH$_3$; E is CH, C—CH$_3$ or C—CONH$_2$; F=CH; X=O or CH$_2$, then R$_2$ will not be H or OH;
when A=N; B=N, CO or CH; C=CH, C—Cl or C—OCH$_3$; D=CH or C—Ph; E is CH, C—Cl or C—Ph; F=N or CO; X=O, then R$_2$ will not be H or OH;

when A=N; B=CO or CS; C=N or NH; D=CO or C—NH$_2$; E is CH or N; F=N or CH; X=O, then R$_2$ will not be H or OH; and when A=C; B=CH; C=NH; D=CO, CS or C—NH$_2$; E is N or NH; F=CO or CH; X=O, then R$_2$ will not be H or OH.

A particular class of compounds contemplated herein includes nucleoside analogs having a ribofuranosyl moiety where the sugar has an L-configuration rather than the natural D-configuration. This class includes compounds which contain modified natural nucleic acid bases and/or synthetic nucleoside bases like triazole, 3-cyano-1,2,4-triazol-3-carboxylate, 3-bromo-5-nitro-1,2,4-triazole, imidazole, 2-nitroimidazole,2-bromo-4(5)-aminoimidazole, pyrazole, 3(5)-aminopyrazole-4-carboxamide, triazines, pyrrole, pyridine, azapyridine, thiazole, 1,2,5-thiadiazole, selenadiazole, 4-amino-1,2,5-thiadiazole-3-carboxylic acid, methyl 4-oxo(5H)-1,2,5-thiadiazole-3-carboxylate, 4-amino-1,2,5-selenadiazole-3-carboxylic acid, tetrazole, azaphophole, 4-amino-1,3-azaphosphole-5-carbonitrile, 4-bromo-1,3-azaphosphole-5-crbonitrile, 2-aminophosphine-3-carbonitrile, methyl 2-amino-3-cyano-phosphole-4-carboxylate, 4,5-dicyano-1,3-diazaphophole, diazaphophole, isooxazole, 3-oxo(2H)-isothiazole-3-carboxylic acid, 5-amino-3-chloroisothiazole-4-carbonitrile, 5-methylthio-3-0xo(2H)-isothiazole-4-carbonitrile, isothiazole, pyrimidine and other substituted derivatives of these bases. Compounds of this class may also contain independently other hetero-monocyclic bases and their derivatives, certain modifications of the ribofuranosyl moiety, and both N- and C-linked L-nucleosides.

Especially preferred compounds in this class include L-Ribavirin, 1-ᴣ-L-ribofuranosyl-1,2,4-triazole-3-carboxamide. L-Ribavirin is described by Figure: where A, B and E are nitrogen; C is C—C(O)NH$_2$; D is nothing; F is CH; X is oxygen; R$_1$, R$_4$, R$_5$, R$_7$ and R$_8$ are hydrogens; and R$_2$, R$_3$, and R$_6$ are hydroxyl.

Ribavirin (1-ᴣ-D-ribafuranosyl-1,2,4-triazole-3-carboxamide) is a monocyclic synthetic D-nucleoside that has been demonstrated activity against variety of viral diseases (Huffman et al, *Antimicrob. Agents Chemother.*, 3, 235, 1975; Sidwell et al, *Science*, 177, 705, 1972) and currently undergoing clinical trials in combination with (-interferon for the treatment of Hepatitis C virus. In the past two decades, a variety of Ribavirin D-nucleoside analogs have been explored and many of them exhibit the exceptional antiviral and antitumor activities. However, no work has been reported on the synthesis of L-isomer of Ribavirin analogs and their biological activity. In single crystal X-ray analysis Ribavirin resemble structurally to guanosine (Prusiner et al., *Nature*, 244, 116, 1973). Because of the resemblance of Ribavirin to guanosine, we expected that Ribavirin nucleoside analogs should show similar or superior immuno-modulating activity than guanosine analogs (Robins et al, U.S. Pat. No. 5,041,426) in addition to the antiviral activity.

Uses

It is contemplated that the compounds of the present invention will used to treat a wide variety of conditions, and in fact any condition which responds positively to administration of one or more of the compounds. Among other things it is specifically contemplated that compounds of the invention may be used to treat an infection, an infestation, a cancer or tumor or an autoimmune disease.

Infections contemplated to be treated with the compounds of the present invention include respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, hantann virus (hemorrhagic fever), human papilloma virus (HPV), measles and fungus.

Infestations contemplated to be treated with the compounds of the present invention include protozoan infestations, as well as helminth and other parasitic infestations.

Cancers or tumors contemplated to be treated include those caused by a virus, and the effect may involve inhibiting the transformation of virus-infected cells to a neoplastic state, inhibiting the spread of viruses from transformed cells to other normal cells and/or arresting the growth of virus-transformed cells.

Autoimmune and other diseases contemplated to be treated include arthritis, psoriasis, bowel disease, juvenile diabetes, lupus, multiple sclerosis, gout and gouty arthritis), rheumatoid arthritis, rejection of transplantation, allergy and asthma.

Still other contemplated uses of the compounds according to the present invention include use as intermediates in the chemical synthesis of other nucleoside or nucleotide analogs which are, in turn, useful as therapeutic agents or for other purposes.

In yet another aspect, a method of treating a mammal comprises administering a therapeutically and/or prophylactically effective amount of a pharmaceutical containing a compound of the present invention. In this aspect the effect may relate to modulation of some portion of the mammal's immune system, especially modulation of lymphokines profiles of Th1 and Th2. Where modulation of Th1 and Th2 lymphokines occurs, it is contemplated that the modulation may include stimulation of both Th1 and Th2, suppression of both Th1 and Th2, stimulation of either Th1 or Th2 and suppression of the other, or a bimodal modulation in which one effect on Th1/Th2 levels (such as generalized suppression) occurs at a low concentration, while another effect (such as stimulation of either Th1 or Th2 and suppression of the other) occurs at a higher concentration.

In general, the most preferred uses according to the present invention are those in which the active compounds are relatively less cytotoxic to the non-target host cells and relatively more active against the target. In this respect, it may also be advantageous that L-nucleosides may have increased stability over D-nucleosides, which could lead to better pharmacokinetics. This result may attain because L-nucleosides may not be recognized by enzymes, and therefore may have longer half-lives.

It is contemplated that compounds according to the present invention will be administered in any appropriate pharmaceutical formulation, and under any appropriate protocol. Thus, administration may take place orally, parenterally (including subcutaneous injections, intravenous, intramuscularly, by intrastemal injection or infusion techniques), by inhalation spray, or rectally, topically and so forth, and in dosage unit formulations containing conventional non-toxic pharmaceutically acceptable carriers, adjuvants and vehicles.

By way of example, it is contemplated that compounds according to the present invention can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) derivatives, pyridine esters and various salt forms of the present compounds are preferred. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to a targeted site within the host organism or patient to maximize the intended effect of the compound.

In addition, compounds according to the present invention may be administered alone or in combination with other agents for the treatment of the above infections or conditions. Combination therapies according to the present invention comprise, the administration of at least one compound of the present invention, or a functional derivative thereof, and at least one other pharmaceutically active ingredient. The active ingredient(s) and pharmaceutically active agents may be administered separately or together and when administered separately this may occur simultaneously or separately in any order. The amounts of the active ingredient (s) and pharmaceutically active agent(s) and the relative timings of administration will be selected in order to achieve the desired combined therapeutic effect. Preferably the combination therapy involves the administration of one compound of the present invention or a physiologically functional derivative thereof and one of the agents mentioned herein below.

Examples of such further therapeutic agents include agents that are effective for the modulation of immune system or associated conditions such as AZT, 3TC, 8-substituted guanosine analogs, 2',3'-dideoxynucleosides, interleukin II, interferons such as (-interferon, tucaresol, levamisole, isoprinosine and cyclolignans. Certain compounds according to the present invention may be effective for enhancing the biological activity of certain agents according to the present invention by reducing the metabolism or inactivation of other compounds and as such, are co-administered for this intended effect.

With respect to dosage, one of ordinary skill in the art will recognize that a therapeutically effective amount will vary with the infection or condition to be treated, its severity, the treatment regimen to be employed, the pharmacokinetics of the agent used, as well as the patient (animal or human) treated. Effective dosages may range from 1 mg/kg of body weight, or less, to 25 mg/kg of body weight or more. In general a therapeutically effective amount of the present compound in dosage form usually ranges from slightly less than about 1 mg./kg. to about 25 mg./kg. of the patient, depending upon the compound used, the condition or infection treated and the route of administration. This dosage range generally produces effective blood level concentrations of active compound ranging from about 0.04 to about 100 micrograms/cc of blood in the patient. It is contemplated, however, that an appropriate regimen will be developed by administering a small amount, and then increasing the amount until either the side effects become unduly adverse, or the intended effect is achieved.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carrier, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Test Results

In vitro and in vivo tests on a compound of Formula I, L-Ribavirin, were performed, and the results are described below.

In a first series of experiments, peripheral blood mononuclear cells (PBMCs) were isolated from the buffy coat following Ficoll-Hypaque density gradient centrifugation of 60 ml blood from healthy donors. T-cells were then purified from the PBMCs using Lymphokwik lymphocyte isolation reagent specific for T-cells (LK-25T, One Lambda, Canoga Park Calif.). An average yield of 40–60×$10^6$ T-cells were then incubated overnight at 37° C. in 20–30 ml RPMI-AP5 (RPMI-1640 medium (ICN, Costa Mesa, Calif.) containing 20 mM HEPES buffer, pH 7.4, 5% autologous plasma, 1% L-glutamine, 1% penicillin/streptomycin and 0.05% 2-mercaptoethanol) to remove any contaminating adherent cells. In all experiments, T-cells were washed with RPMI-AP5 and then plated on 96-well microtitre plates at a cell concentration of 1×$10^6$ cells/ml.

The T-cells were activated by the addition of 500 ng ionomycin and 10 ng phorbol 12-myristate 13-acetate (PMA) (Calbiochem, La Jolla, Calif.) and incubated for 48–72 h at 37° C. PMA/ionomycin-activated T-cells were treated with 0.5–50 µM of either Ribavirin (D-Ribavirin) or L-Ribavirin, or with 250–10000 U/ml of a control antiviral, interferon-alpha (Accurate, Westbury, N.Y.) immediately following activation and re-treated 24 h later. T-cells from each plate were used for immunofluorescence analysis and the supernatants used for extracellular cytokine measurements. Following activation, 900 µl cell supernatant from each microplate was transferred to another microplate for analysis of cell-derived cytokine production. The cells are then used in immunofluorescence analyses for intracellular cytokine levels and cytokine receptor expression.

Cell-derived human cytokine concentrations were determined in cell supernatants from each microplate. Activation-induced changes in interleukin-2 (IL-2) levels were determined using a commercially available ELISA kit (R & D systems Quantikine kit, Minneapolis, Minn.) or by bioassay using the IL-2-dependent cell line, CTLL-2 (ATCC, Rockville, Md. Activation-induced changes in interleukin-4 (IL-4), tumor necrosis factor (TNFα) interleukin-8 (IL-8) (R & D systems (Quantikine kit, Minneapolis, Minn.) and interferon-gamma (IFN-γ) (Endogen (Cambridge, Mass.) levels were determined using ELISA kits. All ELISA results were expressed as pg/ml and the CTLL-2 bioassay as counts per minute representing the IL-2-dependent cellular incorporation of $^3$H-thymidine (ICN, Costa Mesa, Calif.) by CTLL-2 cells.

Figure 13:
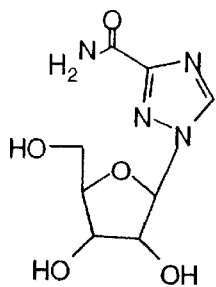
FIGS. 13–14 are graphical representations of the effect of D-Ribavirin and L-Ribavirin on IL-2 TNFα, IFN-γ, IL-4 and IL-5 levels of activated T-cells.
Figure 13:
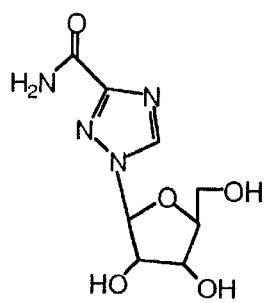
Figure 13:
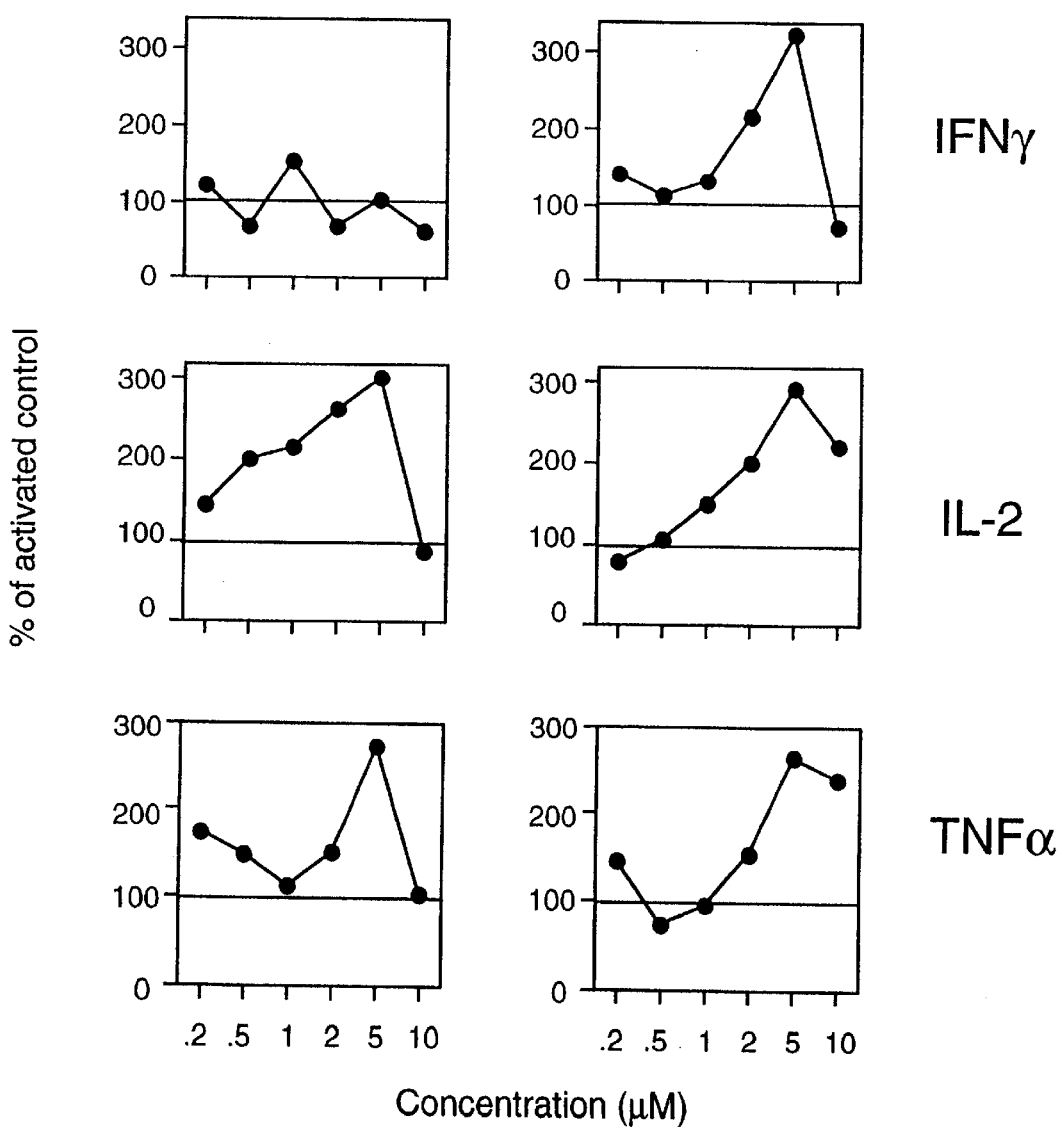
Figure 14:
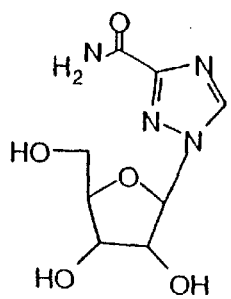
Figure 14:
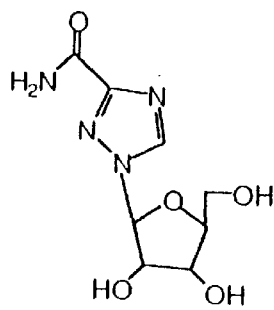
Figure 14:
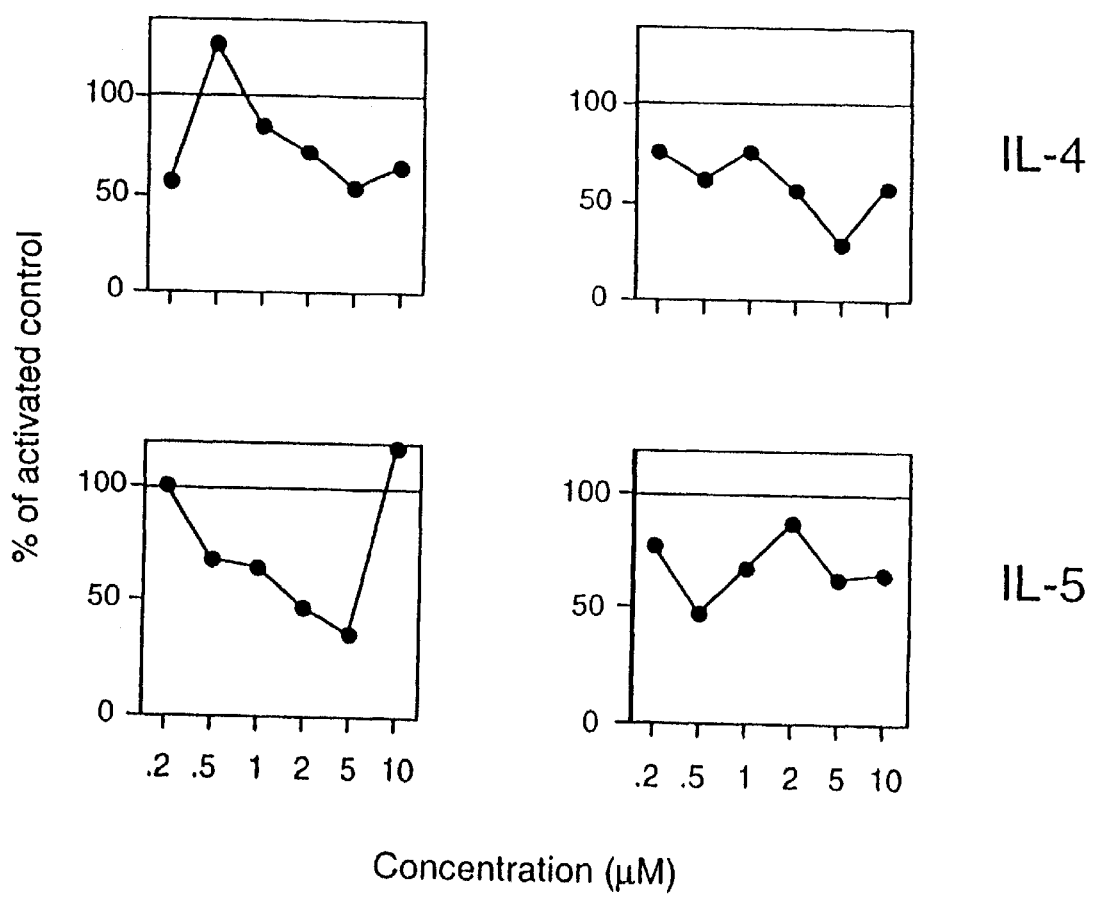

Comparison of the effects of D-Ribavirin and L-Ribavirin (expressed as a percentage of activated control) on IL-2 TNFα, IFN-γ, IL-4 and IL-5 levels are presented in FIGS. 13 and 14.

Figure 15:
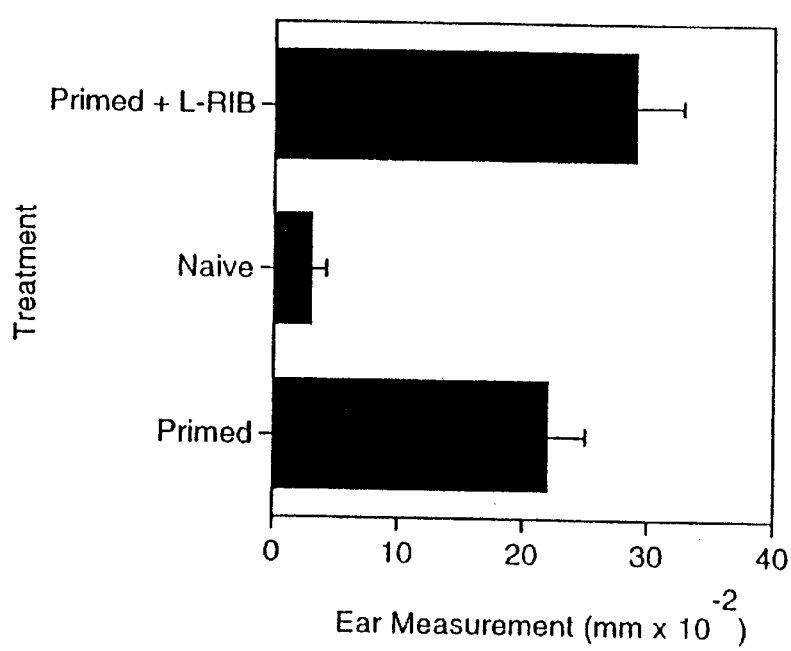
FIG. 15 is a graphical representation of the effects of L-Ribavirin on the inflammatory ear response to dinitrofluorobenzene.
Figure 16:
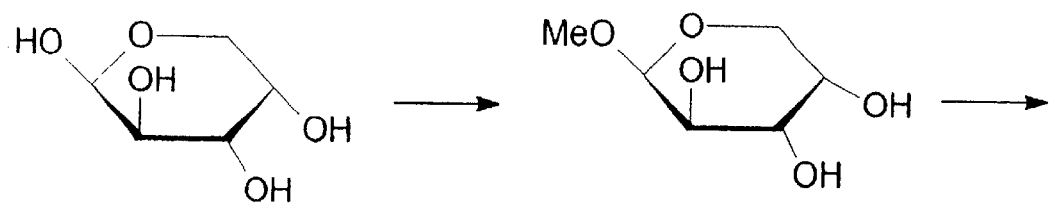
FIGS. 16–26 are schematic representations of synthetic chemical steps which may be used to prepare compounds in the examples section below.
Figure 16:
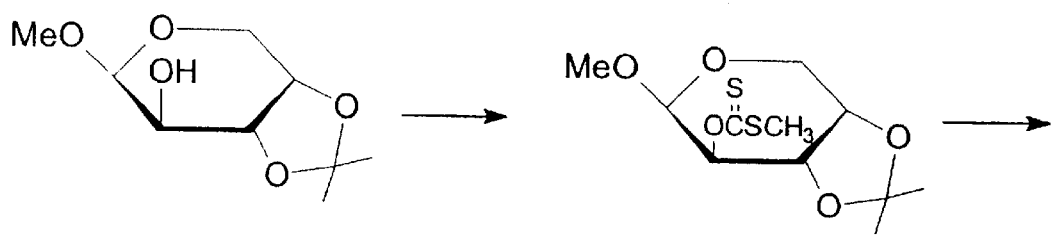
Figure 16:
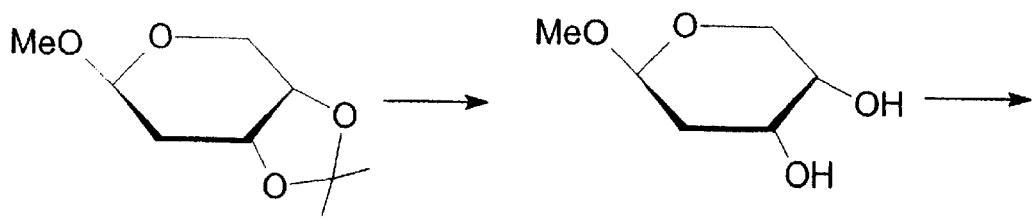
Figure 17:
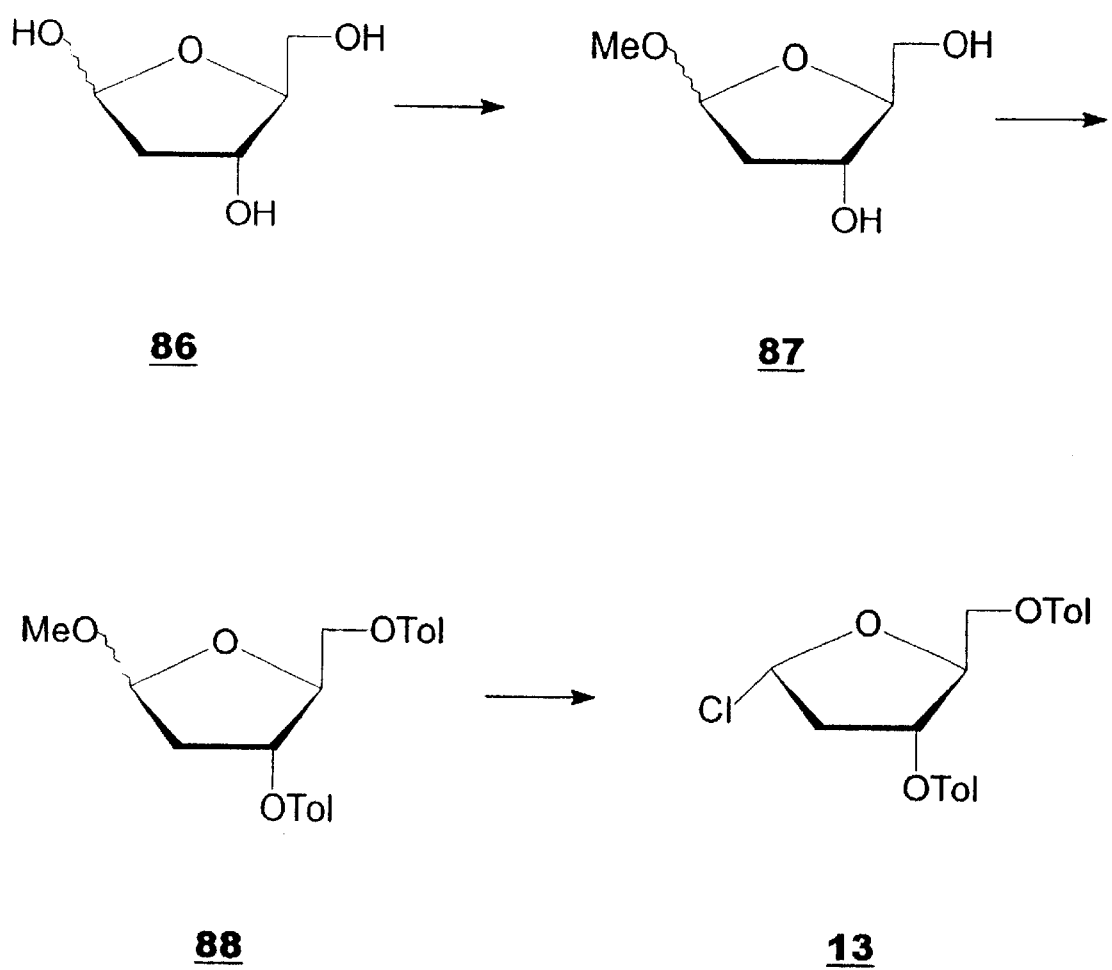
Figure 18:
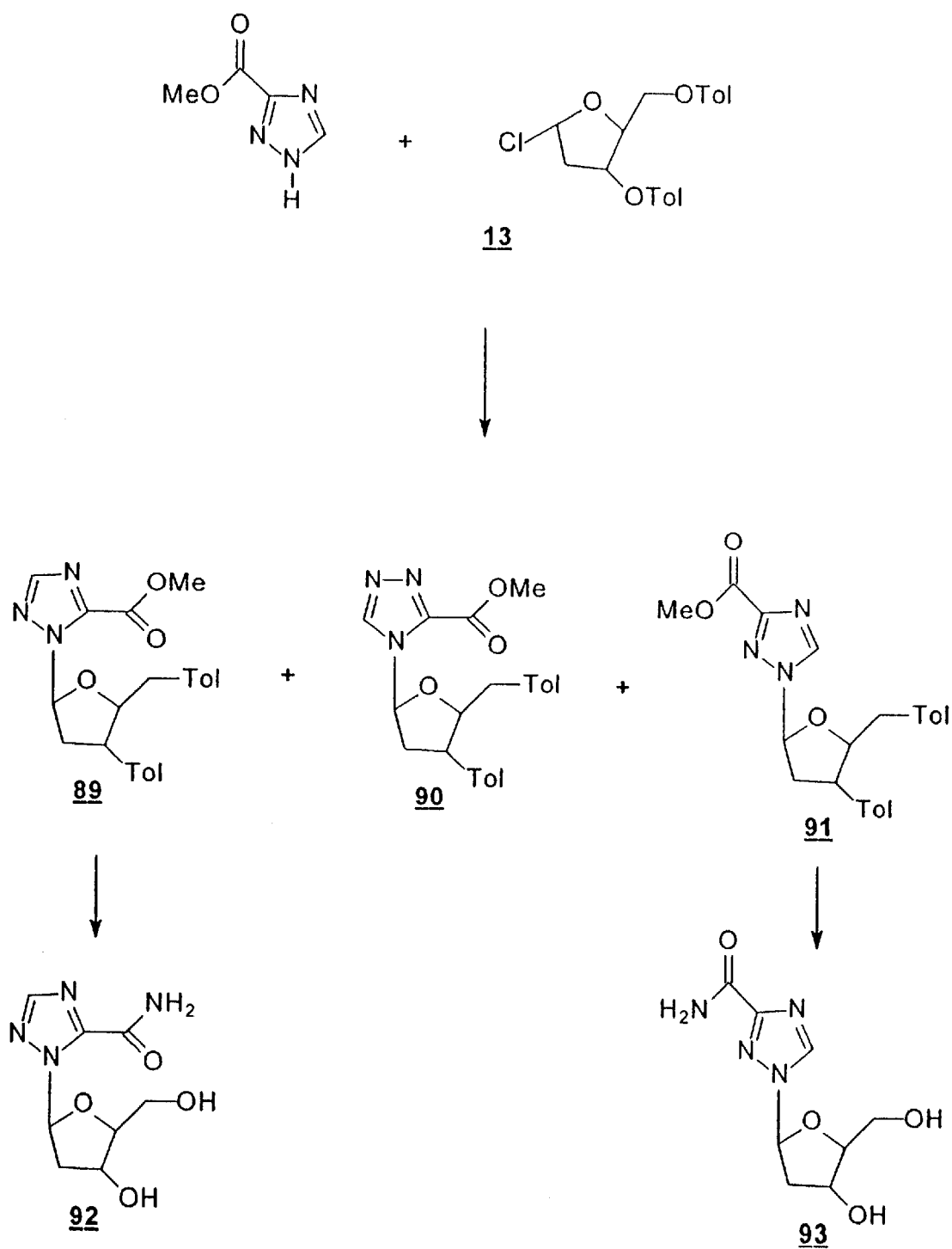
Figure 19A:
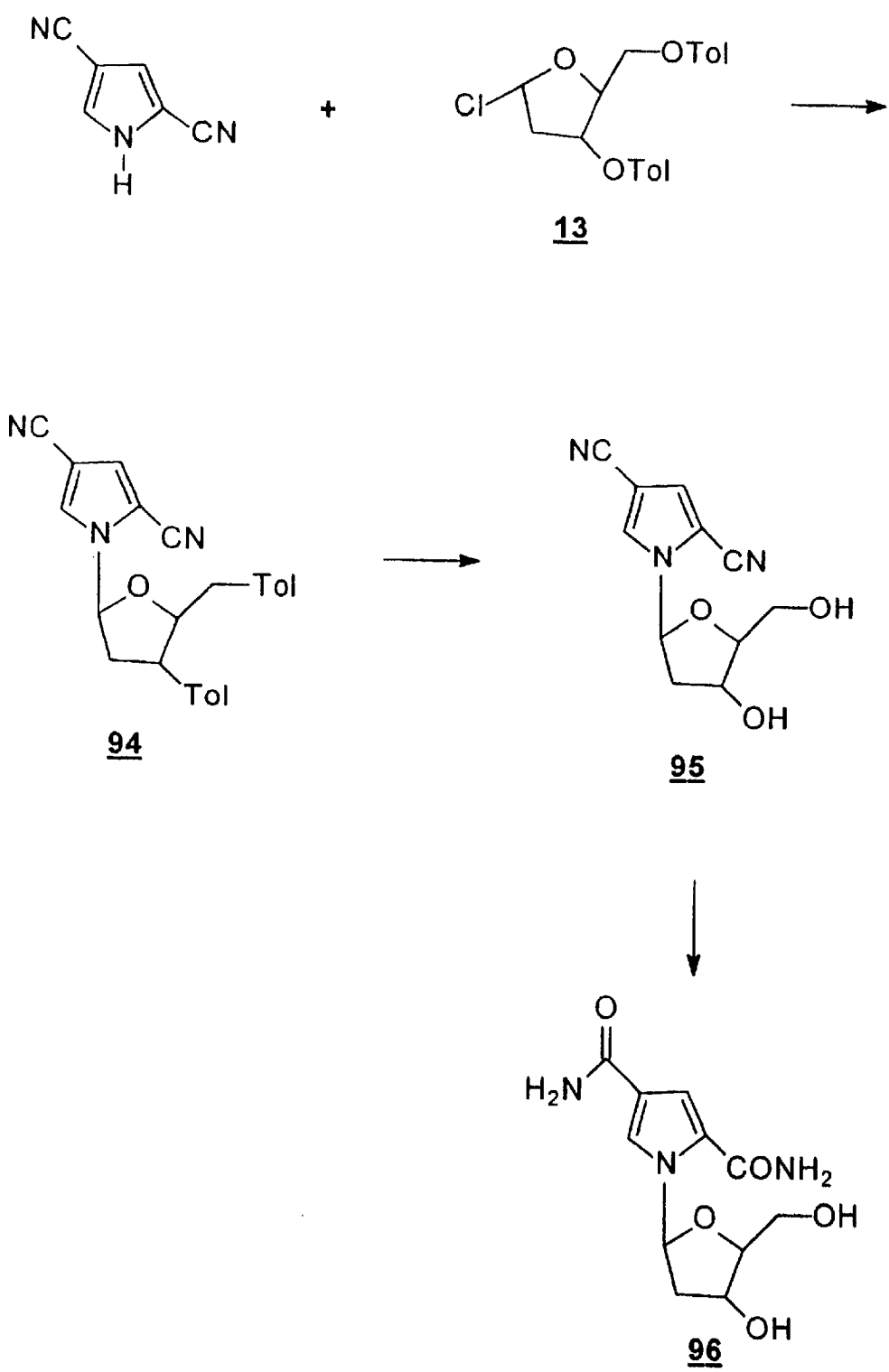
Figure 19B:
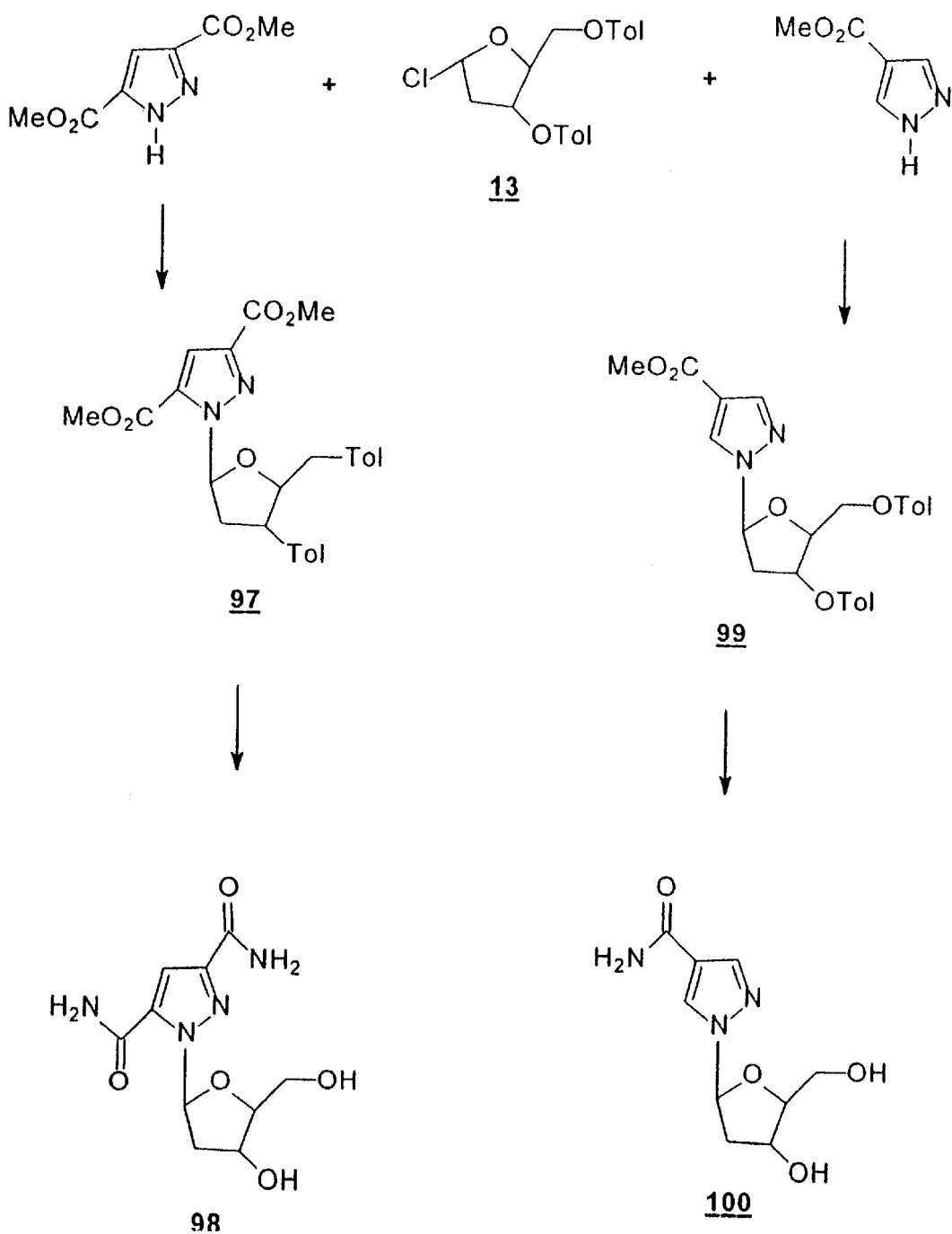
Figure 20:
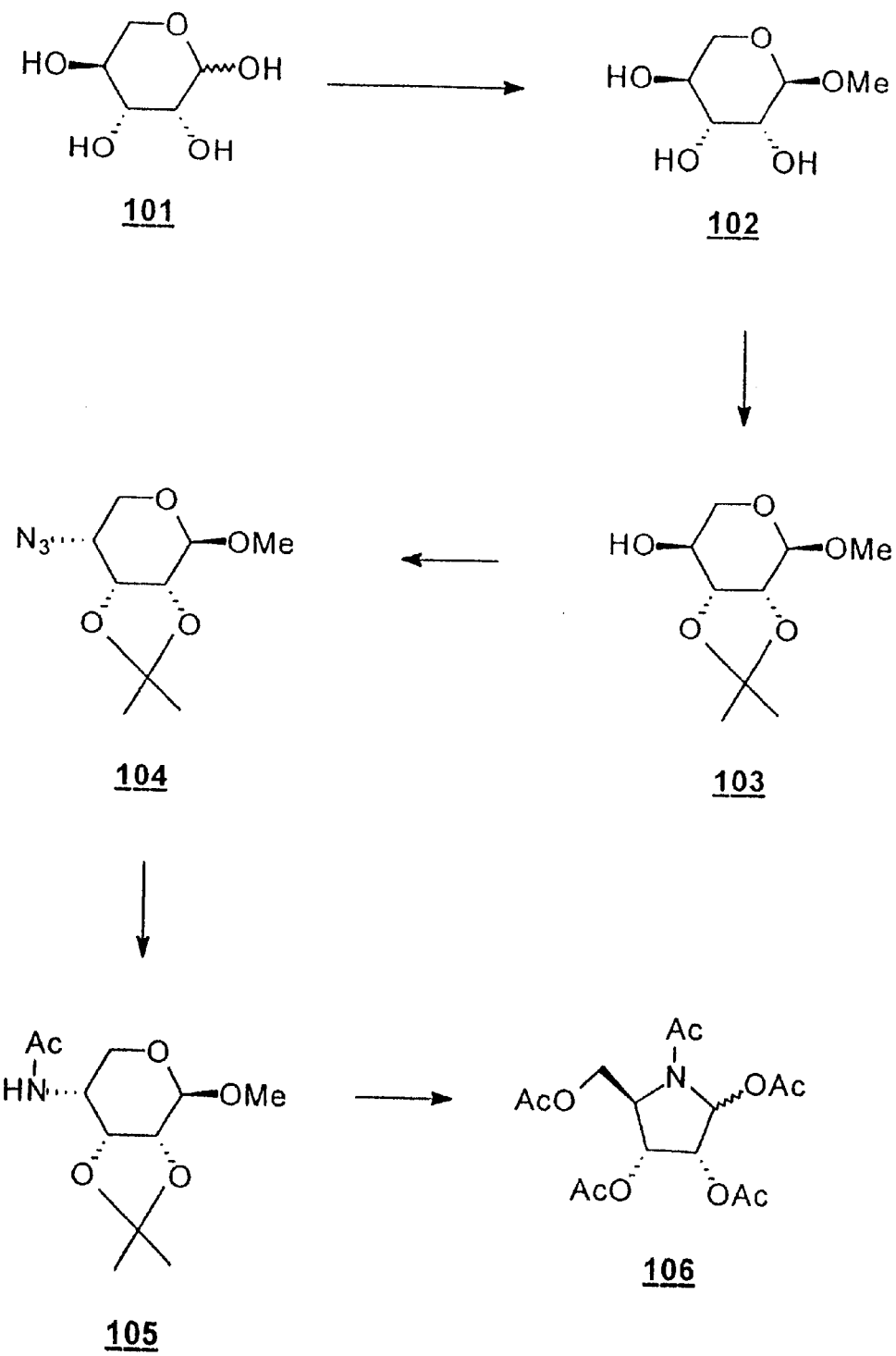
Figure 21:
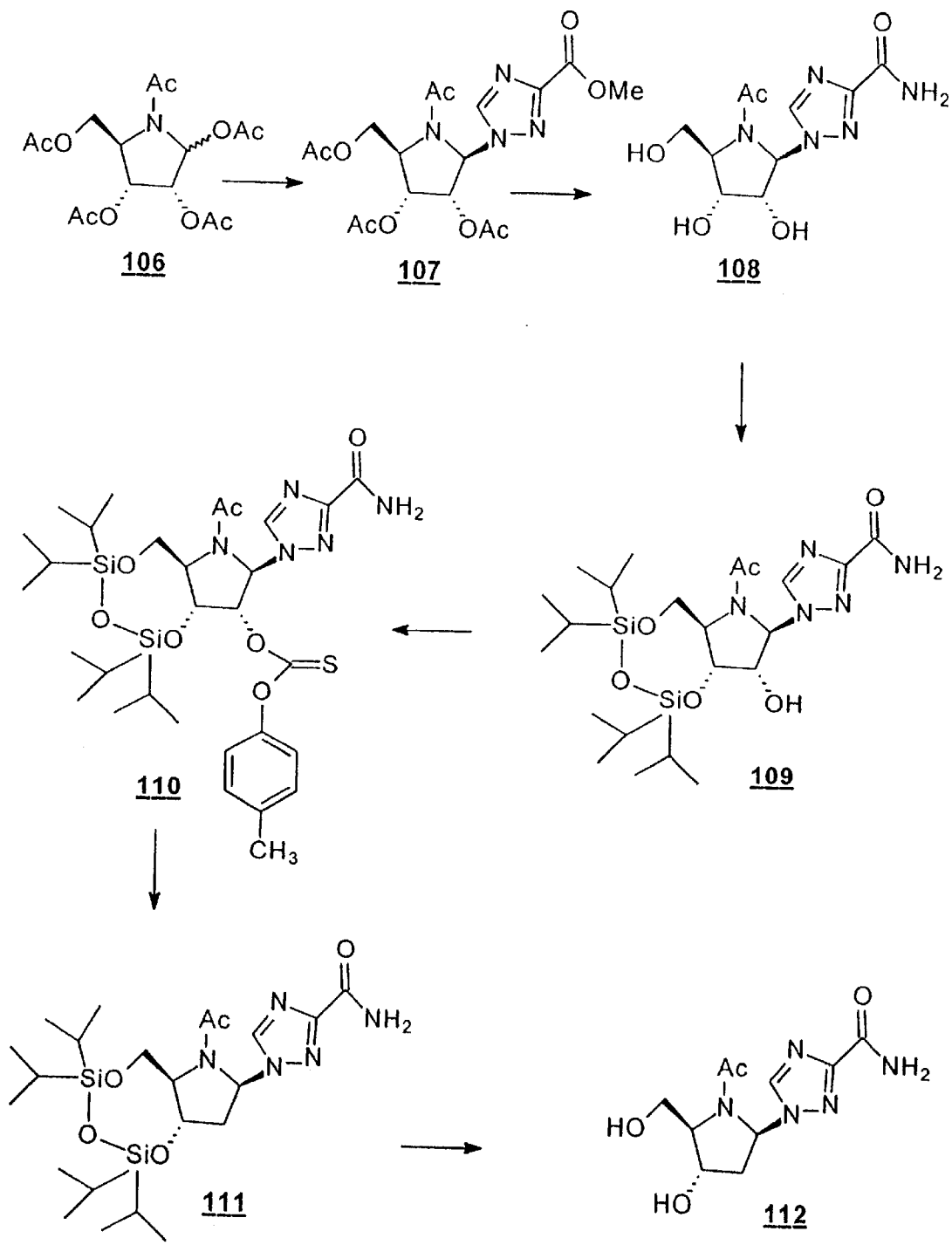
Figure 22:
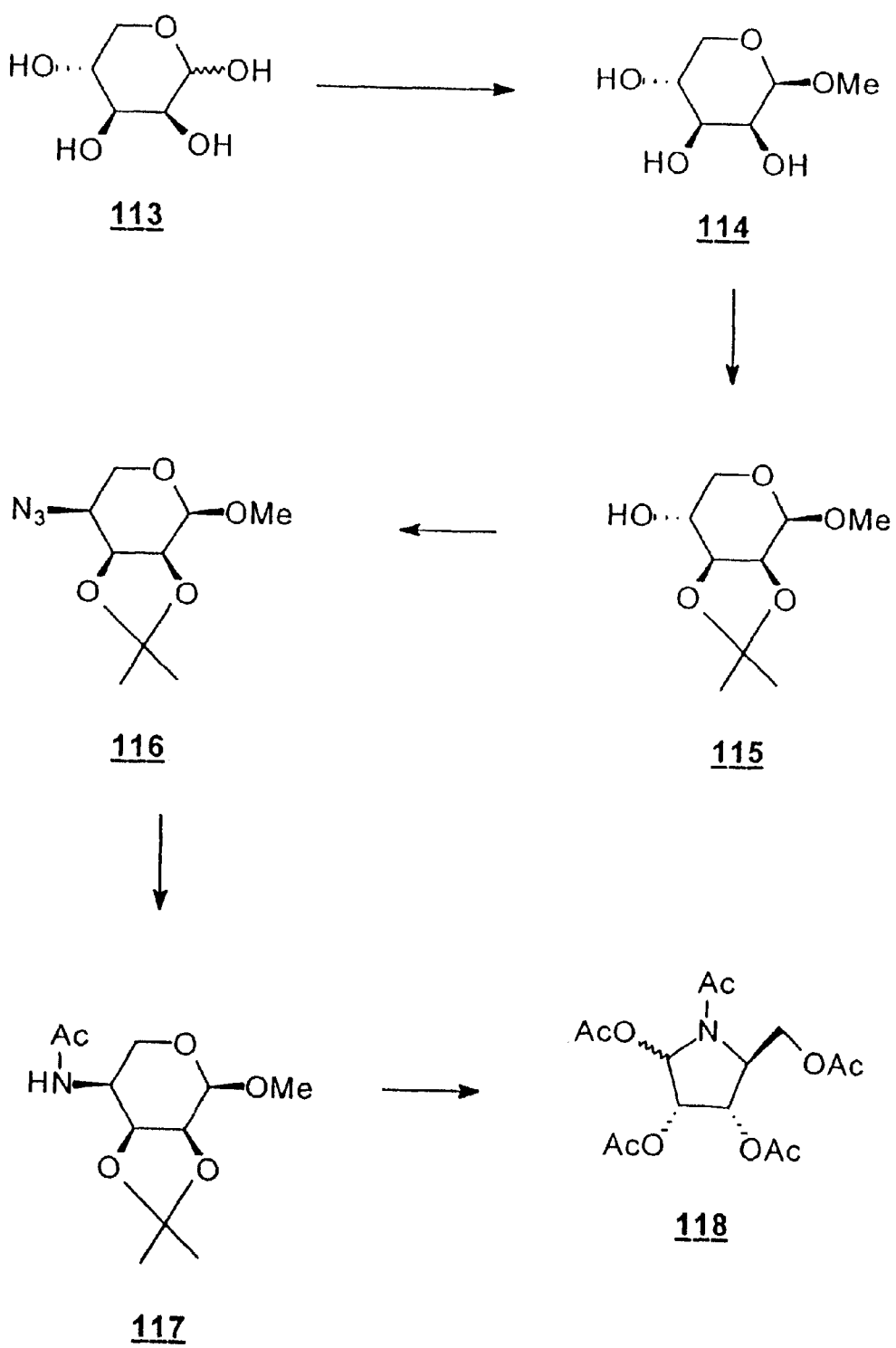
Figure 23:
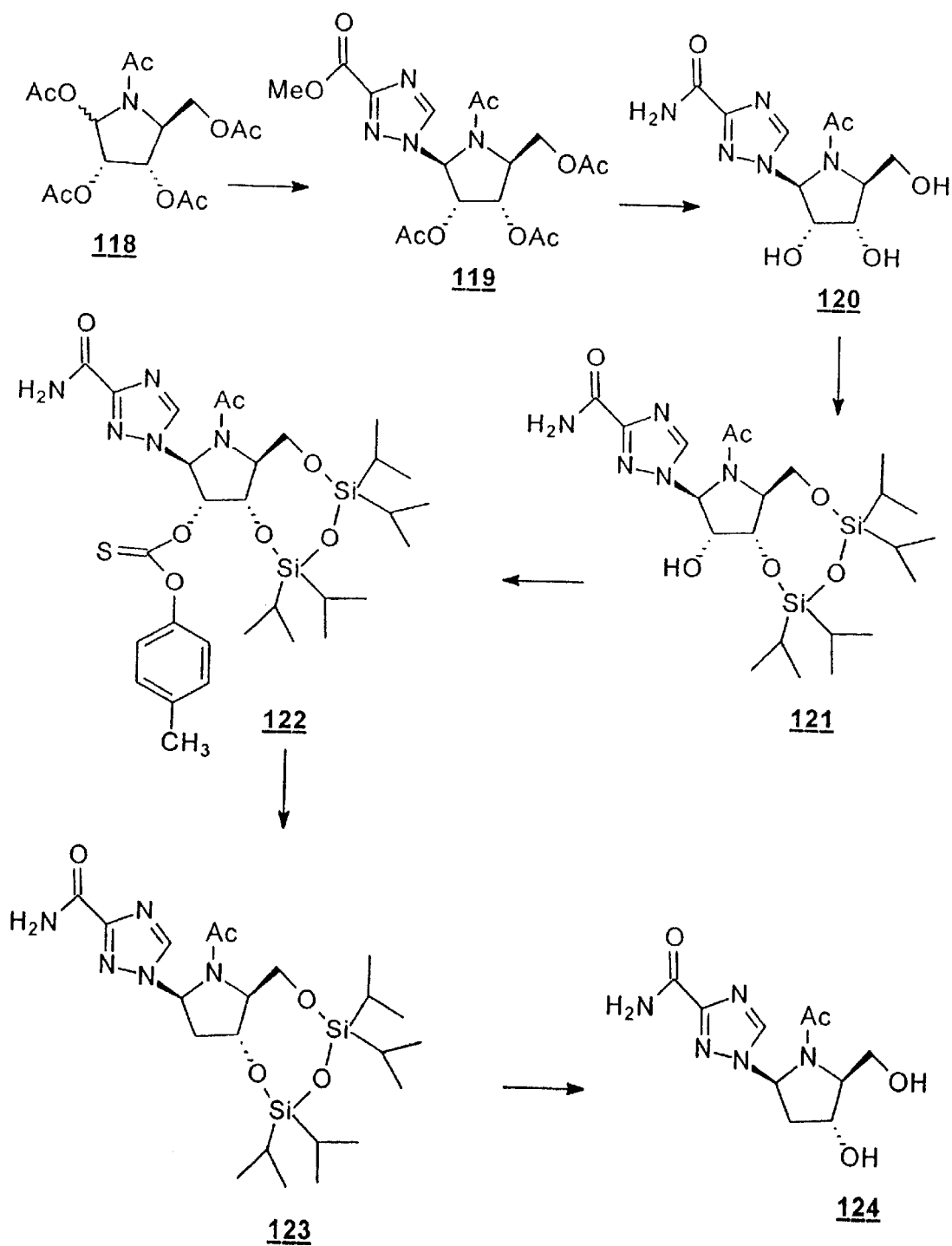
Figure 24:
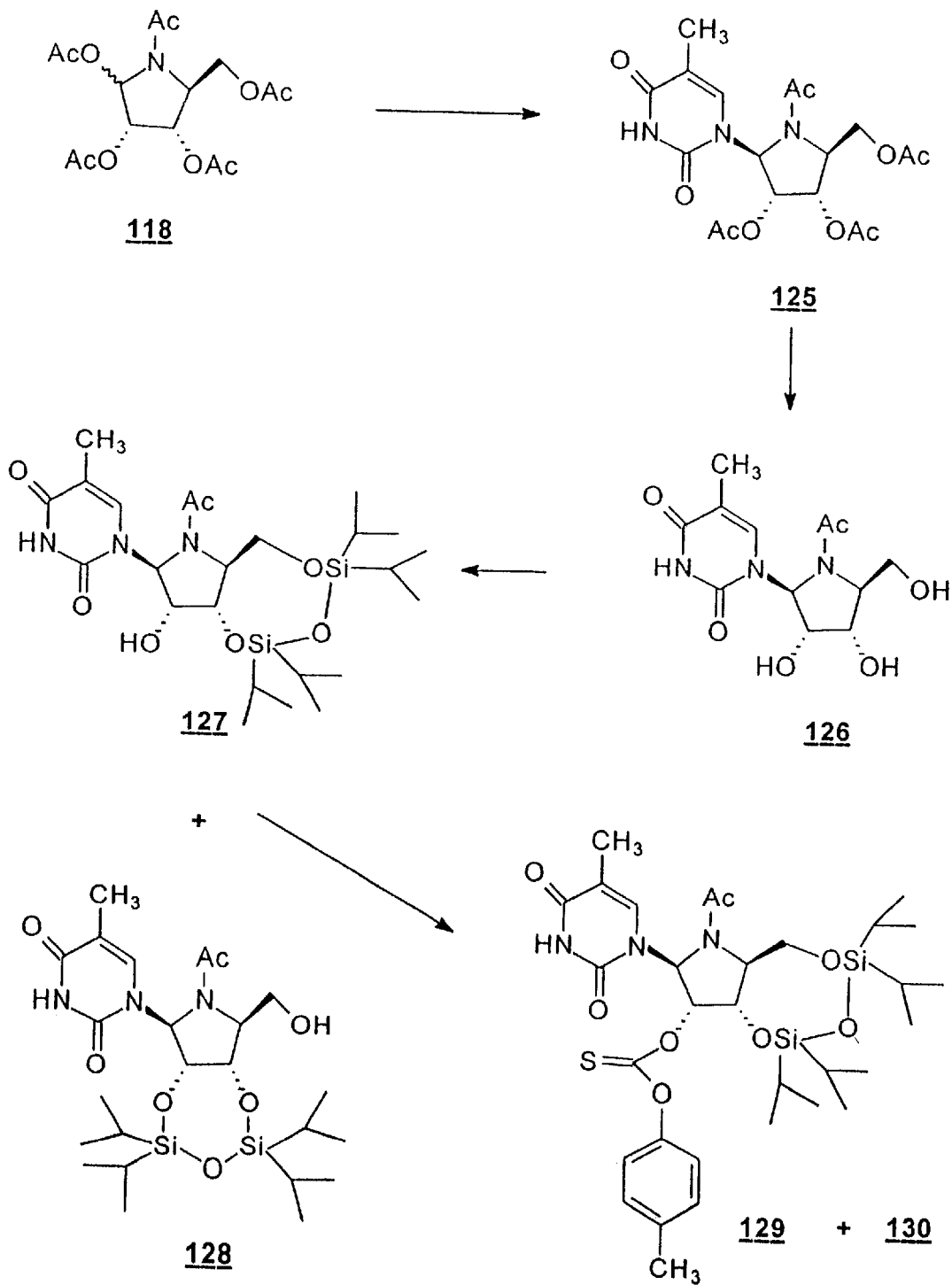
Figure 25:
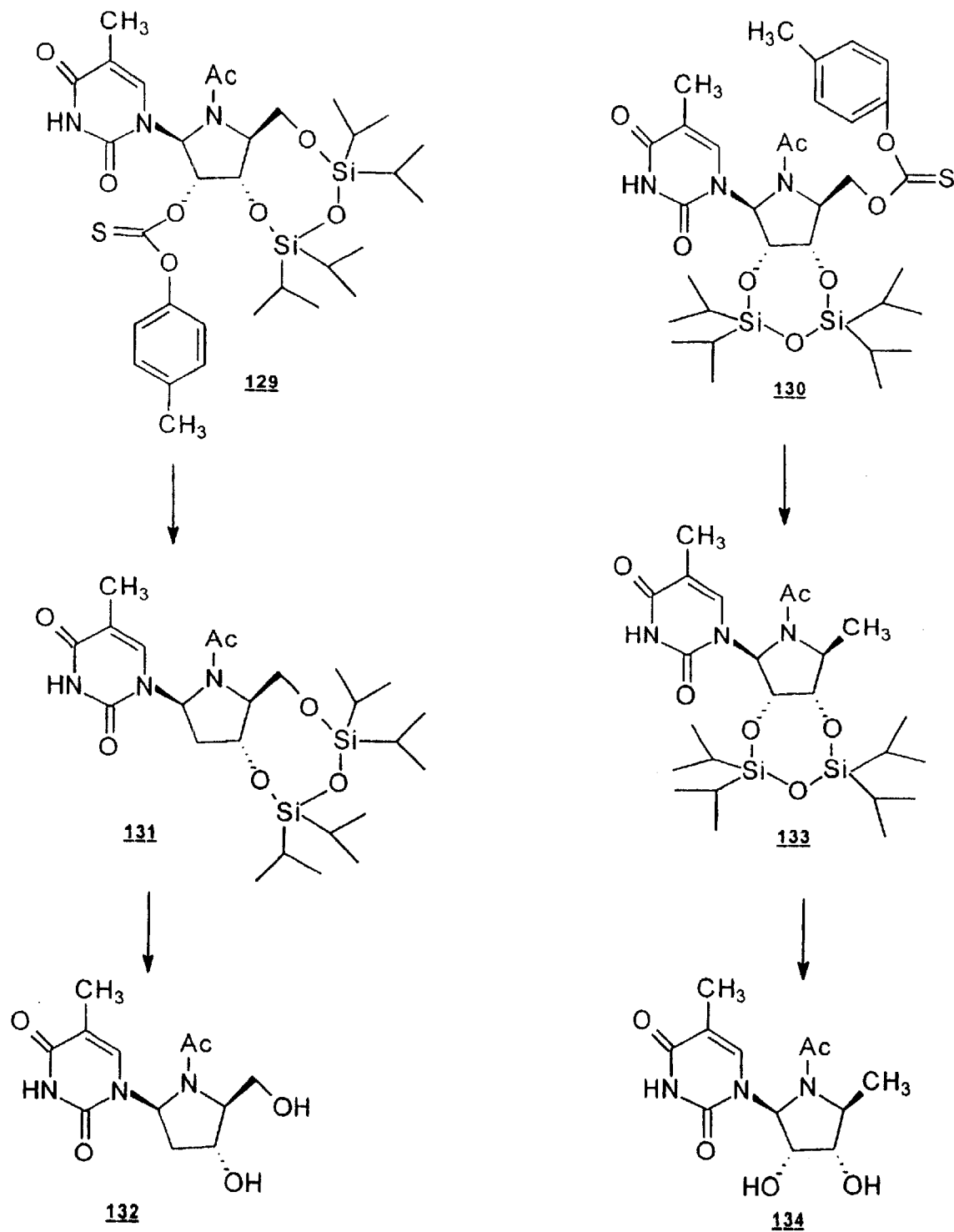
Figure 26:
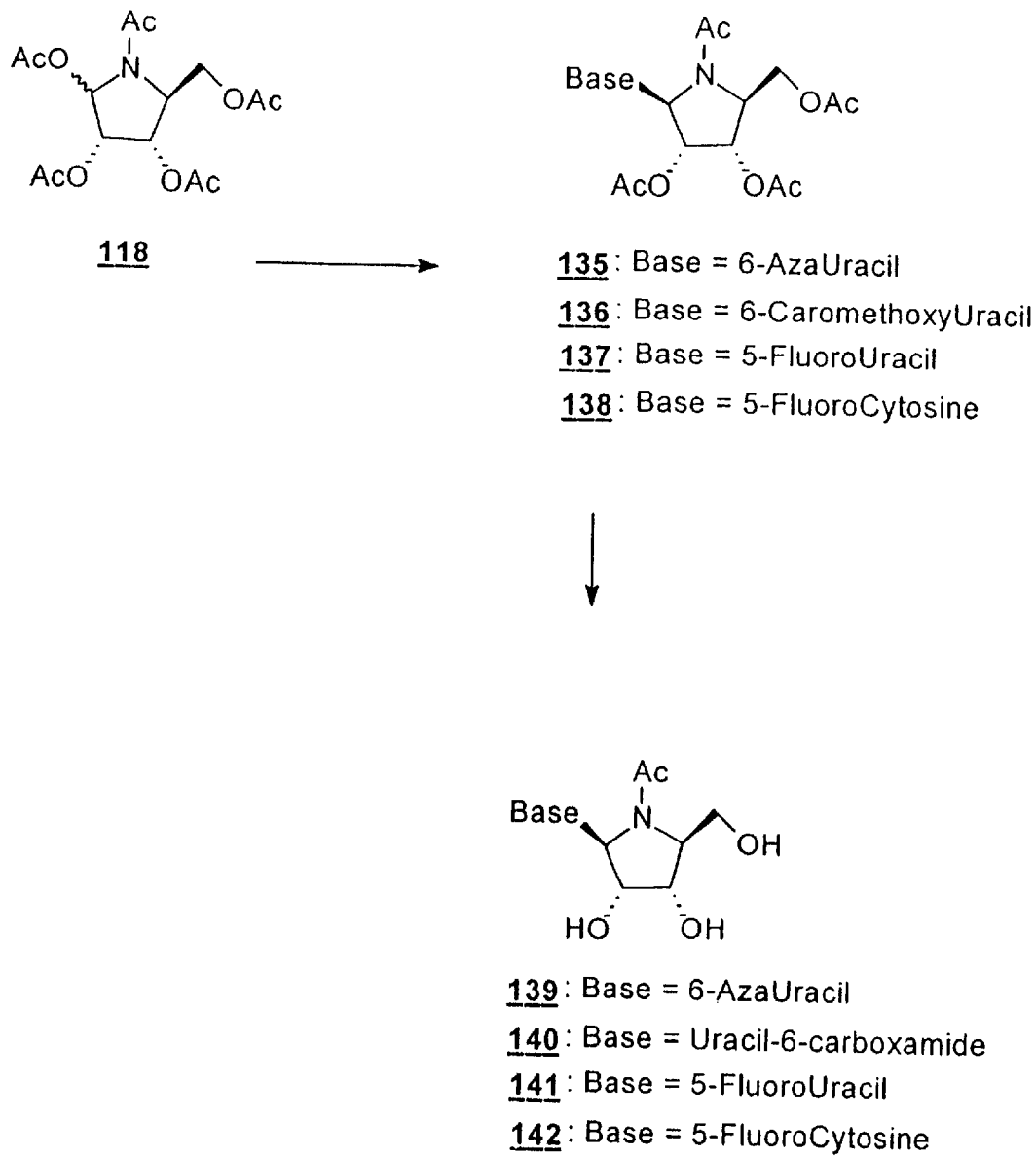

In another set of experiments the effects of L-Ribavirin on the inflammatory ear response to dinitrofluorobenzene were determined. The results of those experiments are shown in FIG. 15.

Synthesis

The compounds according to the present invention may be produced according to synthetic methods which are individually readily known to those of ordinary skill in the art. In general, compounds according to the present invention are synthesized by condensing appropriate nucleoside base with the necessary sugar synthon to give the protected L-nucleoside which on further manipulation and deprotection of the sugar hydroxyl protecting groups will ultimately give rise to nucleoside analog having the desired ribofuranosyl moiety of the L-configuration.

During chemical synthesis of the various compositions according to the present invention, one of ordinary skill in the art will be able to practice the present invention without undue experimentation. In particular, one of ordinary skill in the art will recognize the various steps that should be performed to introduce a particular substituent at the desired position of the base or a substituent at the desired position on the sugar moiety. In addition, chemical steps which are taken to protect fractional groups such as hydroxyl or amino groups, among others, as well as de-protected these same fractional groups, will be recognized as appropriate within the circumstances of the syntheses.

The invention is further defined by reference to the following examples, which are intended to be illustrative and not limiting. It will be understood by one of ordinary skill in the art that these examples are in no way limiting and that variations of detail can be made without departing from the spirit and scope of the present invention.

Compounds of The present invention may be prepared in accordance with well known procedures in the art. Particularly useful are the following synthetic schemes.

Scheme 1: Synthesis of ribofuranosyl (R1, R4, R5, R7 and R8, are hydrogens; R2, R3 and R6 are hydroxyl) nucleosides of formula (II): Triazole L-ribofuranosyl nucleosides were prepared by the acid catalyzed fusion procedure (Sato, T., et al, Nippon Kagaku Zasshi, 81, 1440, 1960). Accordingly, the triazoles (1 were mixed with 1,2,3,5-tetra-O-acetyl-L-ribose (2) and a catalytic amount of bis(p-nitrophenyl)phosphate and heated at 160–165 C. for 30 min under reduced pressure to provide the required nucleosides which on further deprotection furnished the triazole L-ribonucleosides (3) of formula (II).

Scheme 1

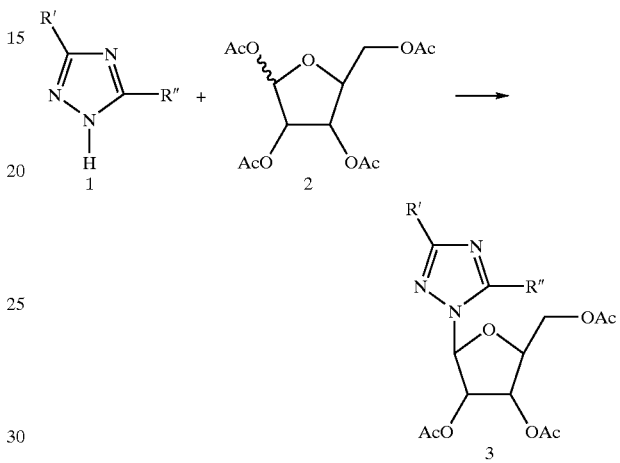

Scheme 2: Synthesis of L-ribofuranosyl (R1, R4, R5, R7 and R8, are hydrogens; R2, R3 and R6 are hydroxyl) nucleosides of formula (III): Triazole, pyrazole and other 5-membered heterocyclic L-ribofuranosyl nucleosides of the present invention were prepared by using Vorbruggen procedure involves the treatment of the heterocycles (4) with chlorotrimethylsilane to provide the silyl intermediate which on condensation with the protected ribose (5)in the presence of stannic chloride in an inert solvent affords the required nucleosides (6). After condensation the products are deprotected by conventional methods known to those skilled in the art, into compounds of the formula (III).

Scheme 2

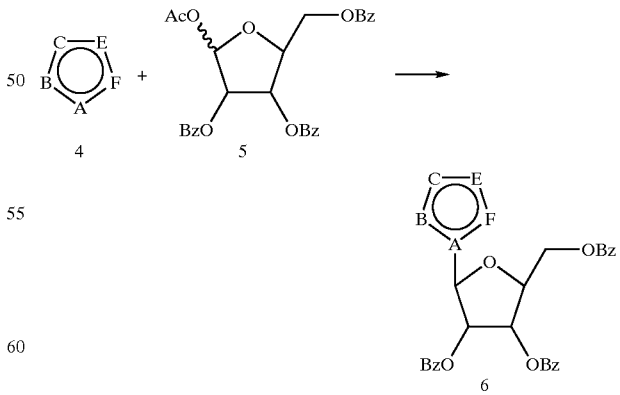

Most of compounds of the formula (III) can be prepared by using the above condensation procedure. The required 1,2,3,5-tetra-O-acetyl-L-ribose and 1-O-acetyl-2,3,5-tri-O-benzoyl-L-ribose were prepared as shown in Example 2 and Example 13 respectively. The hetero monocyclic bases are commercially available from Aldrich, Fluka, ICN, Acros, Alfa, Lancaster and TCI America or were prepared by following the reported procedure that are available in the literature articles (Robins, R. K., et al, Nucleosides & Nucleotides, 13, 17–76, 1994). The preparation pyrrole, pyrazole and other type triazole L-nucleosides of formula (IV) were achieved by following the procedures reported for the preparation of the corresponding D-nucleosides in Chemistry of Nucleosides and Nucleotides, Edited by Leroy B. Townsend, New York, Plenum Press, 3, 1–105, 1994. Various imidazole L-nucleosides were prepared by following the reported (Shaw, G., in Chemistry of Nucleosides and Nucleotides, Edited by Leroy B. Townsend, New York, Plenum Press, 3, 263–420, 1994) methods to imidazole D-nucleosides.

Scheme 3: The compounds of formula (I) could be obtained by reacting the heterocycles (7) with L-ribose (5) by following the Vorbruggen procedure (Niedballa, U., et al, J. Org. Chem., 39, 3654, 1974) described above for the preparation of compounds of formula (III).

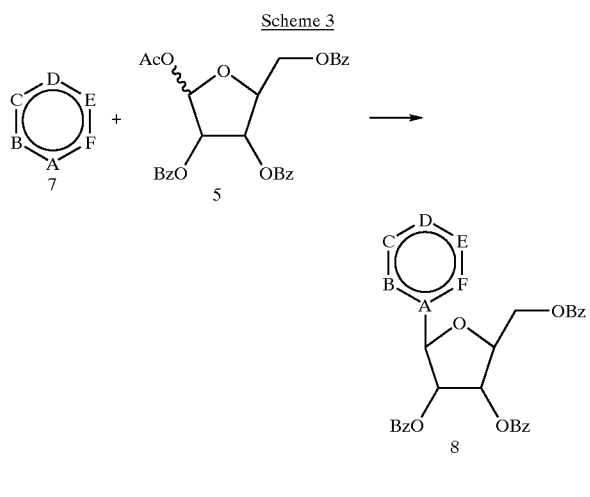

The C-nucleosides (where A is carbon in formulas I & III) of L-configuration were prepared by exemplifying the procedure reported (Watanabe, K. A., in Chemistry of Nucleosides and Nucleotides, Edited by Leroy B. Townsend, New York, Plenum Press, 3, 421–535, 1994) for the preparation their corresponding C-nucleosides of D-configuration.

Scheme 4: Preparation of L-arabinofuranosyl nucleosides ($R_1$, $R_2$, $R_4$, $R_5$ and $R_8$ are hydrogens; $R_3$, $R_6$ and $R_7$ are hydroxyl): The b-anomers of the arabinosyl L-nucleosides of formulae (I-III) may be prepared by reacting 2,3,5-tri-O-benzyl-L-arabinofuranosyl bromide (9; Baker, R., et al., J. Org. Chem., 26, 4605–4609, 1961) and the trimethylsilyl derivative of the base to give the intermediate L-nucleoside (10). Removal of the blocking groups of 10 should afford the required b-L-arabinofuranosyl nucleosides. In the case of pyrrole b-L-arabinonucleosides the sodium salt glycosylation procedure (Revankar, G. R., et al, Nucleosides & Nucleotides, 6, 261–264, 1987) was followed.

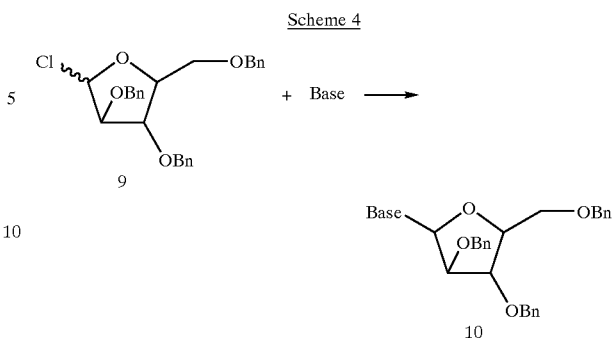

Scheme 5: Preparation of L-xylofuranosyl nucleosides ($R_1$, $R_3$, $R_4$, $R_5$ and $R_7$ are hydrogens; $R_2$, $R_6$ and $R_8$ are hydroxyl): The b-anomers of the xylofuranosyl L-nucleosides of formulae (I-III) may be prepared from 1,2-di-O-acetyl-3,5-di-O-benzyl-L-xylofuranose (11; Gosselin, G., et al., J. Heterocyclic Chem., 30, 1229–1233, 1993) and the appropriate base, by following the method analogous to that described in scheme 4.

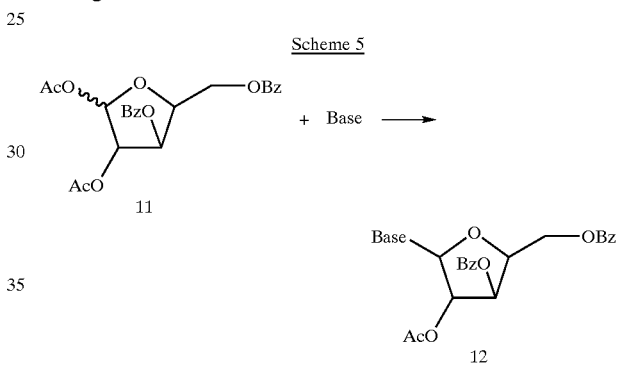

Scheme 6: Preparation of L-2'-deoxyribofuranosyl nucleosides ($R_1$, $R_2$, $R_4$, $R_5$, $R_7$ and $R_8$ are hydrogens; $R_3$ and $R_6$ are hydroxyl): The b-anomers of the 2'-deoxyribofuranosyl L-nucleosides of formulae (I–III) may be prepared by reacting 3',5'-Di-O-p-toluyl-2'-deoxyerythro-b-L-pentofuranosyl chloride (13) (Smejkal, J., et al, Collect. Czec. Chem. Commun. 29, 2809–2813, 1964) with the silyl derivative of the heterocycles in the presence of Bronsted acid to give exclusively the b-isomers (14) in good yield (Fujimori, S., et al, Nucleosides & Nucleotides, 11, 341–349, 1992; Aoyama, H., Bull. Chem. Soc., 60, 2073, 1987). The same b-L-2'-deoxyribofuranosyl nucleosides were also prepared by the reacting the chloro sugar (13) with sodium salt of the base (Kazimierczuk, Z., et al, J. Amer. Chem. Soc., 106, 6379–6382, 1984) in dry acetonitrile. The intermediate (14) on treatment with methanolic ammonia provided the required b-L-2'-deoxyerythro-pentofuranosyl nucleosides.

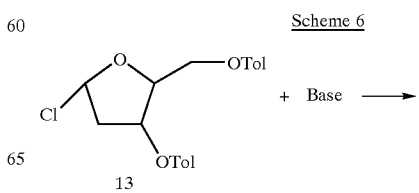

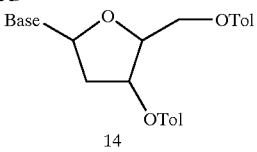

Scheme 7: Preparation of L-3'-deoxyribofuranosyl nucleosides ($R_1$, $R_3$, $R_4$, $R_5$, $R_6$, $R_7$ and $R_8$ are hydrogens; $R_2$ and $R_6$ are hydroxyl): The b-anomers of the 3'-deoxyribofuranosyl L-nucleosides of formulae (I–III) may be prepared by reacting 1,2-di-O-acetyl-5-O-benzoyl-3-deoxy-L-erythro-pentose (15) with the silyl derivative of the heterocycles in the presence of Lewis acid to give the b-isomers (16), which on deblocking with methanolic ammonia should give b-L-3'-deoxyerythro-pentofuranosyl nucleosides. The same compounds could also be prepared by reacting the corresponding 1-chloro derivative of (15) with sodium salt of the heterocyclic base, as in the case of 2'-deoxy L-nucleosides described in scheme 6.

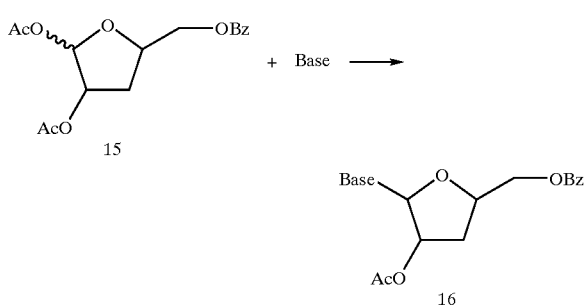

Scheme 8: Preparation of L-2',3'-dideoxyribofuranosyl nucleosides ($R_1$, $R_2$, $R_3$, $R_4$, $R_5$, $R_7$ and $R_8$ are hydrogens; $R_6$ is hydroxyl): The b-anomers of the 2',3'-dideoxyriboftiranosyl L-nucleosides of formulae (I–III) may be prepared by the treatment of their corresponding 5'-O-triphenylmethyl-2',3'-bis (methanesulfonate)-b-L-ribofuranosyl nucleosides (17) with sodium hydrogentelluride (Clive, D. L., et al, *J. Org. Chem.*, 61, 7426–7437, 1996) in $CH_3CN$ at room temperature as shown below. Finally the trityl group will be removed from (18) under mild condition to provide the 2',3'-dideoxyribofuranosyl b-L-nucleosides.

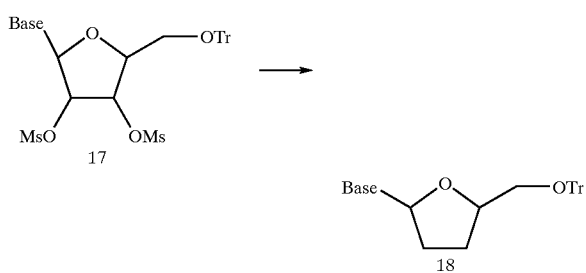

Furthermore, substituted sugars such as 1-bromo-2-deoxy-2-fluoro-3,6-O-benzoyl-L-arabinofuranose (Ma, T., et al, *J. Med. Chem.*, 39 2835–2843, 1996) and other modified sugars of L-configuration are known in U.S. Pat. No. 5,473,063; WO 96/13512; WO 96/13498; WO 96/22778; WO 95/20595; U.S. Pat. Nos. 5,473,063; 5,567,688; WalczaK, K., et al, *Monatsh. fur Chemie*, 123, 349–354 (1992); Wengel, J., et al, *J. Org. Chem.*, 56, 3591–3594 (1991); Genu-Dellac, C., et al, *Tetrahedron Letts.*, 32, 79–82 (1991) and Czemecki, S., et al, *Synthesis*, 783(1991). In addition, preparation of modified sugars and nucleosides of D-configuration are described in U.S. Pat. No. 5,192,749; WO 94/22890; Uteza, V., et al, *Tetrahedron*, 49, 8579–8588 (1993); Thrane, H., et al, *Tetrahedron*, 51, 10389–10403 (1995); Yoshimura, Y., et al, *Nucleosides & Nucleotides*, 14, 427–429 (1993; Lawrence, A. J., et al, *J. Org. Chem.*, 61, 9213–9222(1996); Ichikawa, S., et al, *J. Org. Chem.*, 62, 1368–1375(1997); EP 0 457 326 A1; U.S. Pat. No. 3,910,885; WO 96/13498 and Karpeisky, M, Y., et al, *Nucleic Acids Res. Symposium Series*, 9, 157 (1981). By applying the synthetic procedures (schemes) that has been described in these articles for the preparation of D-nucleosides, the corresponding modified L-nucleosides could also be achieved.

Other compounds within the scope of the invention can be synthesized using the teachings of the schematics provided herein, as well as the specific examples and other schemes set forth below. In addition to the teachings provided herein, the skilled artisan will readily understand how to make compounds within the scope of the present invention by applying well known techniques such as those described in Nucleic Acid Chemistry, Improved and New Synthetic Procedures, Methods and Techniques, Edited by Leroy B. Townsend and R. Stuart Tipson, John Wiley & Sons, New York (1978–1991); Chemistry of Nucleosides and Nucleotides, Edited by Leroy B. Townsend, New York, Plenum Press (1988–1994) and Nucleosides and Nucleotides as Antitumor and Antiviral Agents, Edited by Chung K. Chu and David C. Baker, New York, Plenum Press (1993). Suitable methods for making substitution within the sugar moiety of the presently claimed compounds are known to those skilled in the art and are described in various publications including: U.S. Pat. Nos. 5,559,101; 5,192,749; 5,473,063; 5,565,438. Suitable methods for making various heterocyclic compounds and substitution on them are provided in Chemistry of Nucleosides and Nucleotides, Edited by Leroy B. Townsend, New York, Plenum Press, 2, 161–398 (1991) and Chemistry of Nucleosides and in Nucleotides, Edited by Leroy B. Townsend, New York, Plenum Press, 3, 1–535 (1994).

EXAMPLES

The invention can be further understood by referring to the following examples below, wherein the compound numerals in bold correspond to like numbered numerals in FIGS. 1–12.

Example 1

1-O-Methyl-2,3,5-Tri-O-acetyl-β-L-ribofuranose (19)

L-Ribose (15.0 g, 100 mmol) was dissolved in dry methanol (200 mL) and cooled to 0° C. To this cold stirred solution $H_2SO_4$ (2 mL) was added slowly and the reaction mixture stirred at below 20° C. for 12 h under argon atmosphere. Dry pyridine (75 mL) was added and evaporated to dryness. Dry pyridine (100 mL) was added and evaporated under reduced pressure to an oily residue. This residue was dissolved in dry pyridine (150 mL) and treated with acetic anhydride (50 mL) at 0° C. under argon atmosphere. TEA (41 mL) was added, the reaction stirred at 0° C. for 1 h and at room temperature for 36 h, evaporated to dryness. The residue was dissolved in water (200 mL), solid NaHCO$_3$ was added slowly to adjust the pH of the solution to 7. The aqueous mixture was extracted in CH$_2$Cl$_2$ (250 mL), washed with water (150 mL) and brine (100 mL), dried and concentrated. The oily residue was filtered on a bed of silica gel (200 g), washed with CH$_2$Cl$_2$:EtOAc (8:2, 1000 mL). The filtrate was evaporated and the oil was used as such for the next reaction.

Example 2

1,2,3,5-Tetra-O-acetyl-β-L-ribofuranose (2)

The syrup (19) (29.0 g, 100 mmol) from the above reaction was co-evaporated with dry toluene (2×100 mL) and dried overnight under solid NaOH at room temperature in vacuo. The dried syrup was dissolved in glacial acetic acid (150 mL) and cooled to 0° C. under argon atmosphere. To this cold solution was added acetic anhydride (35 mL) followed by H$_2$SO$_4$ (10 mL) very slowly during 15 minute period. The reaction mixture was stirred at room temperature overnight and poured into ice (200 g) with stirring. The mixture was extracted with CHCl$_3$ (2×200 mL) and the organic extract was washed with water (200 mL), sat. NaHCO$_3$ (200 mL) and brine (150 mL), dried over anhydrous Na$_2$SO$_4$ and evaporated to dryness. The syrup 30 g (94%) that obtained was found to be pure enough for glycosylation reactions.

Example 3A

Methyl 1-(2,3,5-Tri-O-acetyl-β-L-ribofuranosyl)-1,2,4-triazole-3-carboxylate (20)

A mixture of methyl 1,2,4-triazole-3-carboxylate (0.64 g, 5 mmol), 1,2,3,5-tetra-O-acetyl-β-L-ribofuranose (2) (1.5 g, 4.72 mmol) and bis(p-nitrophenyl)-phosphate (20 mg) were placed in a pear shaped flask and placed in a preheated oil bath at (160–165° C.). The flask was connected to a water aspirator and kept at 160–165° C. (oil bath temperature) under reduced pressure with stirring for 25 min. The reaction mixture was removed, cooled and diluted with EtOAc (150 mL) and sat. NaHCO$_3$ (100 mL). The product was extracted in EtOAc. The organic extract was washed with water (100 mL) and brine (50 mL), dried and evaporated to dryness. The residue that obtained was purified by flash column of silica gel using CHCl$_3$→EtOAc as the eluent. The pure fractions were collected and evaporated to dryness to give 1.2 g (66%) of pure product: $^1$H NMR (CDCl$_3$) δ2.10 (3s, 9H, 3 COCH$_3$), 3.98 (s, 3H, OCH$_3$), 422 (m, 1H), 4.46 (m, 2H), 5.54 (t, 1H), 5.76 (m, 1H), 6.04 (d, 1H, C$_1$,H), and 8.38 (s, 1H, C$_3$H). Anal Calc. for C$_{15}$H$_{19}$N$_3$O$_9$ (385.22): C, 46.75; H, 4.97; N,10.91. Found: C, 46.82; H, 4.57; N=10.71.

Example 3B

1-β-L-Ribofuranosyl-1,2,4-triazole-3-carboxamide (21)

The substrate (20) (1.1 g) was dissolved in CH$_3$OH/NH$_3$ at 0° C. and placed in a steel bomb. The bomb was closed and stirred at room temperature for 18 h. The steel bomb was cooled, opened and evaporated to dryness. The residue was tried to crystallization with little ethanol. The product crystallized, but on filtration, the crystals re-absorbed water and became a paste. The crystallization repeated several times. Finally it crystallized from Methanol/Ethanol mixture. The colorless crystals was filtered, washed with methanol and dried in vacuo. The filtrate was evaporated again which on standing gave further crystals. Total yield 0.5 g (72%); mp: 177–179° C.; [a]$_D$=+38.33 (c 3 mg/mL H$_2$O); D form of Ribavirin [a]$_D$=−36.0 (c 3.0 mg/mL H$_2$O); $^1$H NMR (Me$_2$SO-d$_6$) δ3.46 (m, 1H, C$_5$,H), 3.60 (m, 1H, C$_5$,H), 3.92 (q, 1H, C$_4$,H), 4.12 (q, 1H), 4.34 (q, 1H), 4.88 (t, 1H, C$_5$,OH), 5.20 (d, 1H), 5.58 (d, 1H), 5.80 (d, 1H, C$_1$,H), 7.60 (bs, 1H, NH), 7.82 (bs, 1H, NH), and 8.82 (s, 1H, C$_3$H). Anal. Calc. for C$_8$H$_{12}$N$_4$O$_5$ (244.20): C, 39.34; H, 4.95; N, 22.94. Found: C, 39.23; H, 4.97; N, 22.91.

Example 4

2,3-O-Isopropylidene-L-ribose (22)

To a stirred suspension of L-ribose (30.0 g, 260 mmol) in dry acetone (200 mL) was added iodine (1.27 g, 10 mmol) at room temperature under argon atmosphere. The reaction mixture was stirred for 1 h (the solution becomes homogeneous during this period) and quenched with sodium thiosulfate solution (1 M). The solution was evaporated to dryness. The residue was dissolved in CH$_2$Cl$_2$ (250 mL), dried over anhydrous MgSO$_4$, filtered and the solid was washed with CH$_2$Cl$_2$ (150 mL). The combined filtrate was evaporated to dryness. The residue was placed on top of silica column (8×116 cm) packed in CHCl$_3$. The column was eluted with CHCl$_3$ (500 mL), CHCl$_3$:EtOAc (9:1, 1000 mL) and CHCl$_3$:EtOAc (7.3. 1500 mL). The pure product eluted in CHCl$_3$:EtOAc (7:3) was collected and evaporated to give an oily residue 34.5 g (90%). The oily product used as such for the next reaction. $^1$H NMR (CDCl$_3$) δ1.30 and 1.38 (2s, 6H, isopropylidene CH$_3$), 3.70 (m, 3H), 4.08 (m, 1H), 4.38 (m, 1H), 4.55 (d, 1H), 4.81 (d, 1H) and 5.38 (m, 1H).

Example 5

1-Deoxy-1-hydrazinyl-2,3-O-isopropylidene-L-ribose (23)

A solution of 2,3-O-isopropylidene-L-ribose 22 (34.5 g, 182 mmol) in absolute methanol (200 mL) was treated with a solution of anhydrous hydrazine (42.0 g, 1313 mmol) in absolute methanol (100 mL) drop-wise over a period of 30 min and at room temperature under argon atmosphere. The nearly colorless solution was stirred at room temperature and under anhydrous condition for 18 h. The solution was evaporated in vacuo to afford a colorless syrup. The syrup was repeatedly co-evaporated with absolute methanol (5×100 m). The resulting syrup was momentarily warmed (70° C.) under vacuum pump pressure (0.1 torr) and then kept at this pressure for drying for 12 h. The yield was 35.0 g (95%). This material was used as such without further purification for the next step.

Example 6

5-Amino-4-cyano-1-(2',3'-O-isopropylidene-β-L-riboftiranosyl)pyrazole (24)

A solution of 1-deoxy-1-hydrazinyl-2,3-O-isopropylidene-L-ribose (23) (16.3 g, 79.90 mmol) in absolute ethanol (100 mL) was purged with a steady stream of argon for 30 min. A similarly purged solution of (ethoxymethylene)-malanonitrile (10.37 g, 85 mmol) in absolute ethanol (100 mL) was added drop-wise to the rapidly stirred solution at room temperature during a 1 h period. The solution was stirred under argon for an additional 30 min and then heated at reflux for 12 h. The orange solution was cooled to room temperature and evaporated in vacuo to dryness. This material was dissolved in ethyl acetate (100 mL) and then treated with silica gel (50 g). The mixture was evaporated to dryness in vacuo and the powder which resulted was applied to the top of a silica gel (500 g) column (6×30 cm, dry packed). The column was eluted with gradient of $CH_2Cl_2 \rightarrow$ EtOAc solvent. Fractions having the pure product were pooled together and evaporated to a foam: Yield 17 g (76%); $^1$H NMR (CDCl$_3$) δ1.30 and 1.52 (2s, 6H, isopropylidene CH$_3$), 3.86 (m, 2H, C$_5$·H), 4.40 (m, 1H, C$_4$·H), 4.80 (bs, 2H, NH2), 5.00 (d, 1H), 5.20 (m, 1H), 5.80 (d, 1H, C$_1$·H) and 7.54 (bs, 1H, C$_3$H). Anal. Calc. for C$_{12}$H$_{16}$N$_4$O$_4$ (280.28): C, 51.43; H, 5.75; N, 19.99. Found: C, 51.20; H, 5.63; N, 19.98.

Example 7

5-Amino-1-(β-L-ribofuranosyl)pyrazole-4-carbonitrile (25)

A solution of 5-amino-1-(2',3'-O-isopropylidene-p-β-ribofuranosyl)-pyrazole-4-carbonitrile (24) (4.6 g, 16.43 mmol) in 90% trifluoroacetic acid (30 mL) was stirred at room temperature for 4 h. The reaction mixture was evaporated to dryness and the residue was co-evaporated with methanol (3×35 mL). The residue was used as such for further reactions.

Example 8

5-Amino-1-(β-L-ribofuranosyl)pyrazole-4-carboxamide (26)

To a solution of (25) (4.60 g) in ammonium hydroxide (35 mL) was added 30% hydrogen peroxide (2 mL). The mixture was stirred in a pressure bottle at room temperature for 18 h, the pressure bottle was cooled, opened carefully and the volatile products were evaporated to dryness. The residue thus obtained was co-evaporated with ethanol (3×20 mL). The crude product on crystallization with ethanol/water gave pure compound 3.5 g (71%): $^1$H NMR (DMSO-d$_6$) δ3.57 (m, 2H, C$_5$·CH$_2$), 3.86 (q, 1H, C$_4$·H), 4.11 (q, 1H, C$_3$·H) 4.43 (q, 1, C$_2$·OH), 5.63 (d, 1H, J=3.99 Hz, C$_1$·H), 6.51 (br s, 2H, NH$_2$), 6.71 and 7.26 (2br s, 2H, CONH$_2$) and 7.69 (s, 1H, C$_3$H). Anal. Calc. for C$_9$H$_{14}$N$_4$O$_5$ (258.23): C, 41.86; H, 5.46; N, 21.69. Found: C, 41.57; H, 5.40; N, 21.61.

Example 9

5-Amino-1-(2',3'-O-isopropylidene-β-L-ribofuranosyl)pyrazole-3,4-dicaronitrile (27)

A solution of tetracyanoethylene (24.32 g, 190 mmol) in absolute EtOH (100 mL) was added drop-wise with stirring to a solution of 1-deoxy-1-hydrazinyl-2,3-O-isopropylidene-L-ribose (223.0 g, 113.0 mmol) in EtOH (100 mL), over a period of 30 min at 0° C. The reaction mixture was stirred at ice-bath temperature for an additional 2 h and then stirred at room temperature for 15 h. The brown solution was filtered and evaporated to dryness. The residue was dissolved in MeOH (50 mL), adsorbed onto silica gel (90 g), and placed on top of a silica gel column (10×25 cm) packed with CH$_2$Cl$_2$. The column was eluted with CH$_2$Cl$_2$/EtOAc (10:1, v/v); the homogeneous fractions were pooled and evaporated to dryness. The residual yellow foam was crystallized from a ethanol on long standing at room temperature to yield 15 g (44%) of pure (27): mp° C.; $^1$H NMR (Me$_2$SO-d$_6$) δ1.31 and 1.48 (2s, 6H, isopropylidene-CH$_3$), 3.29 (m, 2H, C$_5$·CH$_2$), 4.13 (m, 1H, C$_4$·H), 4.83 (m, 1H, C$_3$·H), 4.97 (t, 1H, C$_5$·OH), 5.24 (m, 1H, C$_2$·H), 6.12 (s, 1H, C$_1$·H), 7.65 (s, 2H, NH$_2$). Anal. Calc. for C$_{13}$H$_{15}$N$_5$O$_4$ (305.29): C, 51.14; H, 4.95; N, 22.94. Found: C, 51.20; H, 5.04; N, 22.61.

Example 10

5-Amino-1-β-L-ribofuranosylpyrazole-3,4-dicarbonitrile (28)

A suspension of 5-amino-1-(2',3'-O-isopropylidene-β-L-ribofuranosyl)-pyrazole-3,4-dicarbonitrile (4.6 g, 15.0 mmol) in 90% TFA/water (50 mL) was stirred at room temperature for 12 h. The solvent was evaporated and the residue was co-evaporated with EtOH (3×50 mL). The light brown residue thus obtained was used as such for further reaction.

Example 11

5-Amino-1-β-L-ribofaranosylpyrazole-3,4-dicarboxamide (29)

The TFA salt of 5-amino-1-β-L-ribofuranosylpyrazole-3,4-dicarbonitrile (28) (2.60 g, 10.0 mmol) was dissolved in conc. NH$_4$OH (28%, 100 mL) and treated with H$_2$O$_2$ (30%, 15 mL). The reaction mixture was stirred at room temperature in a pressure bottle for 12 h, and then evaporated to dryness. The residue was co-evaporated with MeOH (3×50 mL). The crude product was crystallized from a mixture of EtOH/water to give 2.0 g (68%) of (29): mp×° C.; $^1$H NMR (Me$_2$SO-d$_6$) δ3.60 (m, 2H, C$_5$·CH$_2$) 3.87 (m, 1H, C$_4$·H), 4.18 (m, 1H, C$_3$·H), 4.54 (m, 1H, C$_2$·H), 4.91 (t, 1H, C$_5$·OH), 5.03 and 5.38 (2d, 2H, C$_{2',3'}$OH), 5.69 (d, 1H, C$_1$·H, 6.99 (br s, 3H, NH$_2$ and CONH(H)), 7.72 and 7.78 (2s, 2H, CONH$_2$), and 9.65 (d, 1H, CON(H)H). Anal. Calc. for C$_{10}$H$_{15}$N$_5$O$_6$ (301.26): C, 39.87; H, 5.03; N, 23.25. Found: C, 39.72; H, 5.40; N, 23.61

Example 12

Dimethyl 1,2,3-triazole-4,5-dicarboxylate (30)

To a stirred suspension of sodium azide (5.03 g, 77.39 mmol) in DMF (120 mL) was added dropwise at 0° C. over 30 min, a solution of dimethyl acetylene-dicarboxylate (10.0 g, 70.36 mmol) in DMF (100 mL). After 30 min the solvent was removed in vacuo at 30° C. to leave a light purple-brown solid. The solid was washed twice with ether and taken up in water (100 mL). The aqueous solution was acidified with conc. HCl to pH 2. The aqueous layer was first extracted with ether (100 mL) and then with chloroform (100 mL). The combined organic layers were evaporated to give a light red colored solid: 128–130° C. The solid was washed with hot hexane and crystallized from benzene: Yield 11.0 g (85%); $^1$H NMR (CDCl$_3$) δ4.00 (s, 6H), 11.87 (br s, 1H, NH).

Example 13

1-O-Acetyl-2,3,5-tri-O-benzoyl-β-L-ribofuranose (5)

To a solution of L-ribose (25.0 g, 166.66 mmol) in MeOH (300 mL), was added 25 mL of sat. methanolic hydrogen chloride and stirred at room temperature for 6 h. The reaction was complete after 6 h as indicated by TLC using CH$_2$Cl$_2$/MeOH 9:1. After completion of the reaction, dry pyridine (30 mL) was added and the solvents were evaporated. To the residue another 30 mL of pyridine was added and evaporated to dryness. The residue was dissolved in dry pyridine (200 mL) and CH$_2$Cl$_2$ (150 mL) then cooled to 0° C. Benzoyl chloride (96.26 mL, 830.12 mmol) was added drop-wise and stirred at room temperature overnight. TLC using hexane/ethyl acetate (7:3), indicated completion of the reaction. The solvents were evaporated and the residue dissolved in CHCl$_3$ (300 mL), and washed with H$_2$O (200 mL) and sat. NaHCO$_3$ (200 mL), and dried over anhydrous Na$_2$SO$_4$. After evaporating the CHCl$_3$, the residue was co-evaporated with toluene to give an oily residue. The residue was dissolved in AcOH (200 mL), acetic anhydride (85.0 mL; 770.9 mmol) and sulfuric acid (4.46 mL; 83.29 mmol). The reaction mixture was stirred at room temperature overnight, after which time TLC (hexane/ethyl acetate 7:3) indicated completion of the reaction. The solvents were evaporated in vacuo and the residue that obtained was co-evaporated with toluene. The brown residue was triturated with EtOH to give light brown crystals. Filtration of the solid and recrystallization from EtOH gave 1-O-acetyl-2,3,5-tri-O-benzoyl-L(+)-glucofuranose 40.5 g (48.0%) as white crystals: mp 125–125° C.; $^1$H NMR (CDCl$_3$) δ4.49 (m, 1H, C$_5$H), 4.77 (m, 2H, C$_4$H and C$_5$H), 5.80 (d, 1H), 5.93 (m, 1H, C$_2$H), 6.43 (d, 1H, C$_1$H, J$_{1,2}$=1.5 Hz) and 7.30–8.09 (m, 15H, PhH).

Example 14

Dimethyl 2-(2',3',5'-tri-O-benzoyl-β-L-ribofuranosyl)-1,2,3-triazole-4,5-dicarboxylate (31)

A mixture of dry dimethyl 1,2,3-triazole-4,5-dicarboxylate (3.70 g, 20.0 mmol), hexamethyldisilazane (HMDS, 60 mL), and (NH$_4$)$_2$SO$_4$ (0.1 g) was heated under reflux (oil-bath temperature 140° C.) for 12 h with the exclusion of moisture. Excess HMDS was removed by distillation in vacuo to provide the trimethylsilyl derivative, which was dissolved in anhydrous CH$_3$CN (100 mL).

To the above clear solution was added 1-O-acetyl2,3,5tri-O-benzoyl-L-ribofuranose (10.12 g, 20 mmol) and the mixture was stirred for 10 min. To this stirred solution was added trimethylsilyl trifluoromethanesulfonate (4.6 mL, 26.0 mmol) and the stirring was continued for 12 h at ambient temperature. The reaction mixture was evaporated ant the residue was dissolved in CH$_2$Cl$_2$ (500 mL). The organic layer was washed successively with aqueous sat. NaHCO$_3$ solution (3×100 mL), sat. NaCl solution (×100 mL), and water (×50 mL) and dried over anhydrous Na$_2$SO$_4$. The solvent was evaporated furnish 12.0 g (95%) of 31: $^1$H NMR (Me$_2$SO-d$_6$) δ3.88 (s, 6H, 2 OCH$_3$), 4.65 (m, 2H, C$_5$H), 5.01 (m, 1H, C$_4$H), 6.10 (m, 1H, C$_3$H), 3.32 (m, 1H, C$_2$'H), δ6.88 (d, 1H, C$_1$H, J$_{1,2}$=2.75 Hz) and 7.45–7.95 (m, 15H, PhH).

Example 15

2-β-L-Ribofuranosyl-1,2,3-triazole-4,5-dicarboxamide (32)

Compound 31 (6.0 g, 9.5 mmol) was dissolved in MeOH/NH$_3$ (dry MeOH sat. with anhydrous NH$_3$ at 0° C., 60 mL) were placed in a steel reaction vessel. The vessel was heated at 95° C. for 16 h. The reaction vessel was cooled, opened carefully and the NH$_3$ was allowed to evaporate at room temperature. The MeOH was evaporated to dryness and the residue was triturated with hot toluene (3×50 mL) and filtered. The brown residue was crystallized from aqueous EtOh (95) to furnish 2.40 g (89%) of 32: mp 210–212° C.; $^1$H NMR (Me$_2$SO-d$_6$) δ3.45–3.59 (m, 2H, C$_5$H), 3.98 (m, 1H, C$_4$H), 4.25 (m, 1H, C$_3$H), 4.54 (m, 1H, C$_2$H), 4.78 (t, 1H, C$_5$OH, D$_2$O exchangeable), 5.27 and 5.67 (2d, 2H, C$_{2',3'}$OH, D$_2$O exchangeable), 5.89 (d, 1H, J$_{1',2'}$=3.85 Hz, C$_1$H), 8.05 and 9.05 (2br s, 4H, 2 CONH$_2$). Anal. Calc. for C$_9$H$_{13}$N$_5$O$_6$ (287.23): C, 37.63; H, 4.56; N, 24.38. Found: C, 37.52; H, 4.19; N, 24.59.

Example 16

1-(2',3',5'-Tri-O-benzoyl-β-L-riboftiranosyl)pyridine-4-one-3-carboxamide (33)

To a mixture of hexamethyldisilazane (50 mL, 239.77 mmol) and chlorotrimethylsilane (1.0 mL, 21.43 mmol) was added pyridine-4-one-3-carboxamide (1.38 g, 10.0 mmol) (Prepared by the procedure reported: W. C. J. Ross, *J. Chem. Soc., C,* 1816, (1966); W. Herz and D. R. K. Murty, *J. Org. Chem.,* 26, 122, 1961). The mixture was refluxed with stirring for 2 h and then evaporated to dryness under vacuum and further dried under high vacuum for 2 h at 60° C. The dry gummy residue was suspended in freshly distilled 1.2-dichlorethane (50 mL) and to this suspension was added 1-O-acetyl-2,3,5-tri-O-benzoyl-L-ribofuranose (5.06 g, 10.0 mmol) and freshly distilled SnCl$_4$ (1.0 mL, 8.52 mmol). The reaction mixture was refluxed for 1.5 h, cooled and diluted with CH$_2$Cl$_2$ (100 ml) and sat. aqueous NaHCO$_3$ (25 ml). The Mixture was filtered through celite and the bed was washed with Ch$_2$Cl$_2$ (20 mL). The mixture was filtered washed with water until the washings are neutral, dried over anhydrous sodium sulfate. The organic extract was evaporated to dryness to give a gummy residue. The residue was purified by flash chromatography over silica gel using CH$_2$Cl$_2$→EtOAc as the eluent. Pure fractions were pooled and concentrated to provide 0.50 g (9%) of 33 as white foam: $^1$H NMR (CDCl$_3$): δ4.94 (m, 3H, C$_4$H and C$_5$H), 6.12 (m, 1H), 6.20 (m, 1H), 6.32 (d, 1H) and 7.20–8.30 (m, 20H).

Example 17

1-δ-L-ribofuranosylpyridine-4-one-3-carboxamide (34)

Compound 33 (0.5 g, 0.86 mmol) was dissolved in dry methanolic ammonia (50 mL) and stirred for 15 h in a bomb at room temperature. The solution is then concentrated to a small volume and cooled overnight at 4° C. The crystalline product formed was filtered off, washed with cold methanol. The solid was recyrstallized from absolute ethanol to give 0.23 g (87%) of pure product: mp 209–211° C.; $^1$H NMR (Me$_2$SO-d$_6$) δ3.60 (m, 2H, C$_5$H), 3.93 (m, 1H, C$_4$H), 4.09 (m, 1H, C$_3$H), 4.34 (m, 1H, C$_2$H), 5.11 (m, 1H, C$_5$OH, D$_2$O exchangeable), 5.22 and 5.47 (2m, 2H, C$_{2',3'}$OH, D$_2$O exchangeable), 5.84 (d, 1H, J$_{1',2'}$=6.3 Hz, C$_1$H), 7.21 (m, 2H, PhH), 7.64 (m, 2H, PhH and CONH$_2$) and 8.44 (s, 1H, CONH$_2$). Anal. Calc. for C$_{11}$H$_{14}$N$_2$O$_6$ (270.24): C, 48.89; H, 5.22; N, 10.37. Found: C, 48.89; H, 5.42; N, 10.51.

Example 18

2,3,5-Tri-O-benzoyl-β-ribofuranosyl Azide (35)

Dry hydrogen chloride was passed through a suspension of finely powdered and dried 1-O-acetyl-2,3,5-tri-O-benzoyl-L-ribose (20.0 g, 39.52 mmol) in ether (300 mL.) at 0° C. until a clear solution obtained (2–3 h). The mixture was then set aside at 0° C. overnight. The solvent was removed and the residual gum evaporated successively with dry benzene (2×25 mL.) and toluene (25 mL.). The residue was dissolved in methyl cyanide (250 mL). To this was added sodium azide (20.0 g, 307.6 mmol) and the reaction mixture was refluxed under argon atmosphere for 2 h. After the completion of the reaction, as determined by TLC hexane/ethyl acetate (7:3), the solution was filtered and evaporated to give an oily product (14.6 g) in quantitative yield. The product gave a white foam under high vacuum drying. The dried material was used as such for further reaction. $^1$H NMR (CDCl$_3$) δ4.54 (m, 1H), 4.76 (m, 2H), 5.57–5.58 (dd, 1H), 5.68 (d, 1H, J=1.65 Hz), 5.84–5.86 (m, 1H) and 7.34–8.12 (m, 15H, PhH).

Example 19

5-Amino-1-(2',3',5'-tri-O-acetyl-β-L-ribofuranosyl)triazole-4-carboxamide (36)

N,N-Dimethylformamide (60 mL) was added to a cold (0° C.) solution of potassium hydrocide (1.72 g, 30.7 mmol) in water (10 mL) and the solution stirred at this temperature for 10 min. Cyanoacetamide (2.58 g, 30.68 mmol) was added to this solution and the mixture was then stirred at 0° C. until all the solid material had dissolved. To this solution was added 2,3,5-tri-O-benzoyl-b-L-ribofuranosyl azide (10.0 g, 20.5 mmol) in one portion, and the reaction was stirred at −5° C. for 14 h. The amber solution was evaporated in vacuo (water bath 50° C.) to afford an orange semisolid, which was successively co-evaporated with absolute ethanol (2×50 mL) and toluene (3×50 mL) in vacuo to afford a thick orange gum. The gum was dissolved in anhydrous methanol (150 mL), sodium methoxide (1 N, 25 mL) was added and the solution was stirred at room temperature under anhydrous conditions for 6 h. The amber solution was treated with Dowex 50×H$^+$ ion-exchange resin (ca. 35 mL wet resin) to adjust the pH to 6. The solution was filtered, the resin bed was washed with an additional methanol (50 mL) and the combined filtrates were evaprated to dryness in vacuo (water bath 80° C.) to yield an orange gum. The gum was repeatedly triturated with ethyl acetate (6×50 mL), and each portion was in turn decanted until the gum solidified to a tan amorphous solid. The off-white crude product 2.5 g (32%) was chromatographically pure. After several crystallization the product contained impurities it is converted to the acetate form as described below.

The above crude material (0.4 g, 1.54 mmol) was dissolved in dry pyridine (10 mL). The solution was cooled to 0° C. under argon atmosphere and treated with acetic anhydride (0.95 g, 9.26 mmol). The reaction mixture was stirred at room temperature overnight and the quenched with methanol (1.0 mL). The solvent was removed and the residue dissolved in CH$_2$Cl$_2$ (100 mL). The organic layer was washed with sat. NaHCO$_3$ (100 mL) and brine (50 mL), dried and evaporated to dryness. The crude product was purified by flash chromatography over silica gel using EtOAc as the eluent: Yield 0.52 g (88%); $^1$H NMR (CDCl$_3$) δ2.12 (3s, 9H, 3 COCH$_3$), 4.32–4.52 (m, 3H), 5.64 (m, 1H, C$_3$,H), 5.85 (m, 1H, C$_2$,H), 6.00 (br s, 2H, NH$_2$), 6.32 (d, 1H, C$_1$,H) and 8.73 (br s, 2H, CONH$_2$).

Example 20

5-Amino-1-β-L-(+)-ribofuranosyltriazole-4-carboxamide (37)

Compound 36 (0.5 g, 1.29 mmol) was dissolved in methanolic ammonia (50 mL, sat. at 0° C.). The reaction mixture was stirred at room temperature for 16 h and evaporated to dryness. The residue was triturated thrice with EtOAc and the solid was crystallized from minimum amount of dry EtOH to yield colorless solid: mp 159–161° C.; $^1$H NMR (Me$_2$SO-d$_6$) δ3.40–3.52 (m, 2H, C$_5$,H), 3.93 (m, 1H, C$_4$,H), 4.19 (m, 1H, C$_3$,H), 4.46 (m, 1H, C$_2$,H) 4.74, 5.22, 5.62 (m, 3H, 3 OH, D$_2$O exchangeable), 5.84 (d, 1H, J=3.90 Hz, C$_1$,H), 7.95 (br s, 2H) and 9.02 (br s, 2H). Anal. Calc. for C$_8$H$_{13}$N$_5$O$_5$ (259.22): C, 37.07; H, 5.05; N, 27.02. Found: C, 37.36; H, 5.14; N, 27.01.

Example 21

5-O-Acetyl-1-(2',3',5'-tri-O-acetyl-β-L-ribofuranosyl)triazole-4-carboxamide (38)

N,N-Dimethylformamide (40 mL) was added to a cold (0° C.) solution of potassium hydroxide (1.16 g, 20.82 mmol) in water (20 mL), and the soluation stirred at this temperature for 10 min. Ethyl malonamate (2.73 g, 20.82 mmol) was added to this solution, and the mixture was then stirred at 0° C. until all of the solid material had dissolved. To this solution was added 2,3,5-tri-O-benzoyl-β-L-ribofuranosyl azide (6.76 g, 13.88 mmol) in one portion, and the reaction was stirred at −5° C. for 14 h. The amber solution is evaporated in vacuo (water bath 80° C. to afford an orange semisolid, which was successively co-evaporated with absolute ethanol (2×50 mL) and toluene (3×50 mL) in vacuo to afford a thick orange gum. The gum was dissolved in anhydrous methanol (150 mL), sodium methoxide (0.5 N, 10 mL) was added and the solution was stirred at room temperature under anhydrous condition for 6 h. The amber solution was treated with Dowex 50×H$^+$ ion-exchange resin (ca. 35 mL wet resin) to adjust the pH to 6. The solution was filtered, the resin bed was washed with an additional 50 mL of methanol, and the combined filtrates were evaporated to dryness in vacuo (water bath 80° C.) to yield an orange gum. The gum was repeatedly triturated with ethyl acetate (6×50 mL), and each portion was in turn decanted until the gum solidified to a tan amorphous solid. The solid was suspended in anhydrous pyridine (30 mL) and acetic anhydride (7.8 mL, 83.28 mmol), stirred under anhydrous conditions at room temperature for 18 h. The reaction mixture was filtered through a shallow bed of packed Celite. The Celite bed was washed with fresh pyridine (50 mL) and the combined filtrates were evaporated to dryness in vacuo to yield a brown gum. The gum was dissolved in CH$_2$Cl$_2$ (150 mL). The organic layer was washed with sat. NaHCO$_3$ (100 mL) and brine (50 mL), dried and evaporated to dryness. The crude product was purified by flash chromatography over silica gel using CH$_2$Cl$_2$→EtOAc as the eluent. Pure fractions were collected and evaporated to provide 1.5 g (42%) of pure product 38. $^1$H NMR (CDCl$_3$) δ2.14 (3s, 9H, 3 COCH$_3$), 2.60 (s, 3H, COCH$_3$), 4.15–4.58 (m, 3H, C$_4$,H and C$_5$,H),5.62 (m, 1H, C$_3$,H), 5.82 (m, 1H, C$_2$,H), 6.28 (d, 1H, C$_1$,H) and 10.63 (br s, 2H, CONH$_2$).

Example 22

5-Hydroxy-1-β-L-(+)-ribofuranosyltriazole-4-carboxamide (39)

Compound 38 (1.5 g, 3.50 mmol) was dissolved in meth; methanolic ammonia (50 mL, saturated at ° C.). The reaction mixture was stirred at room temperature for 16 h and evaporated to dryness. The residue was triturated thrice with EtOAc and the solid was crystallized from minimum amount of dry EtOH to yield 0.70 g (77%) of 39: mp 162–164° C.; $^1$H NMR (Me$_2$SO-d$_6$) δ3.40–3.50 (m, 2H, C$_5$,H), 3.84 (m, 1H, C$_4$H), 4.17 (m, 1H, C$_3$H), 4.32 (m, 1H, C$_2$H), 4.90 (t, 1H, C$_5$OH), 5.20, 5.58 (2d, 2H, 2 OH, D$_2$O exchangeable), 5.76 (d, 1H, J=3.90 Hz, C$_1$H), 7.58 and 7.80 (2br s, 2H, CONH$_2$) and 8.82 (s, 1H, C$_5$OH). Anal. Calc. for C$_8$H$_{12}$N$_4$O$_6$ (260.21): C, 36.92; H, 4.65; N, 21.53. Found: C, 36.90; H, 4.79; N, 21.43.

Example 23

1-(2',3',5'-Tri-O-benzoyl-β-L-ribofuranosyl)-6-methyluracil (40)

A mixture of 6-methyluracil (2.52 g, 20.0 mmol), hexamethyldisilazine (50 mL) and ammonium sulfate (100 mg) were refluxed at 135° C. for 6 h. The solvent was removed in vacuo and the residue that obtained was co-evaporated twice with dry toluene (2×50 mL) to remove last traces of hexamethyldisilazine. The solid thus obtained was dried under vacuum for 6 h. A solution of the 2,4-bis (trimethylsilyloxy)-6-methylpyrimidine (20.0 mmol) in dry acetonitrile (100 mL) was added 1-O-acetyl-2,3,5-tri-O-benzoyl-L-ribofuranose (10.12 g, 20 mmol) and trimethylsilyltriflate (5.78 g, 26.0 mmol. The reaction mixture was stirred under argon at room temperature for 16 h. The reaction mixture was concentrated in vacuo and the residue was dissolved in dichloromethane (200 mL). The organic layer was washed with sat. sodium bicarbonate (200 mL) and brine (100 mL), dried over sodium sulfate and concentrated to yield a white foam. Further separation of the crude product by silica gel flash column chromatography using the CH$_2$Cl$_2$→EtOAc as the eluent gave two products. Yield of the 2$^{nd}$ fraction 4.50 g (42%). $^1$H NMR (CDCl$_3$) δ2.28 (s, 3H, CH$_3$), 4.65–4.81 (m, 3H, C$_4$H and C$_5$H), 5.60 (m, 1H, C$_3$H), 5.72 (s, 1H), 6.11 (m, 1H), 7.24–8.06 (m, 16H, PhH) and 9.40 (br s, 1H, NH). The first fraction (4.20 g) did not correspond to the desired compound according to $^1$H NMR.

Example 24

1-β-L-Ribofuranosyl-6-methyluracil (41)

A solution of 40 (4.50 g, 7.86 mmol) was dissolved in sat. methanolic ammonia (60 mL). The reaction mixture was heated at 100° C. for 17 h in a steel bomb. The reaction vessel was cooled to room temperature and concentrated to yield an oil. The reside was further purified by silica gel flash column chromatography using dichloromethane and methanol (9:1) as the eluent. Pure fractions were collected and evaporated to give a white solid. This was further recyrstallized from 2-propanol to afford 1.98 g (94%) of pure 41: mp 175–177° C.; $^1$H NMR (Me$_2$SO-d$_6$) δ2.24 (s, 3H, CH$_3$), 3.42–3.57 (m, 2H, C$_5$H), 3.68 (m, 1H, C$_4$H), 4.0 (m, 1H, C$_3$H), 4.53 (m, 1H, C$_2$H), 4.68, 4.94, 5.22 (m, 3H, 3 OH, D$_2$O exchangeable), 5.43 (d, 1H, C$_1$H, J$_{1',2'}$=3.85 Hz), 5.56 (s, 1H, C$_5$H) and 11.25 (s, 1H, NH). Anal. Calc. for C$_{10}$H$_{14}$N$_2$O$_6$ (258.23): C, 46.51; H, 5.46; N, 10.85. Found: C, 46.66; H, 5.26; N, 10.66.

Example 25

1-(2',3',5'-Tri-O-benzoyl-β-L-ribofuranosyl)-5-azacytidine (42)

5-Azacytosine (1.12 g, 10.0 mmol) was suspended in a mixture of hexamethyldisilazine (50 mL) and of ammonium sulfate(100 mg). The reaction mixture was refluxed at 135° C. for 6 h. Later, the solvents were removed in vacuo and the residue thus obtained was co-evaporated twice from dry toluene (2×50 mL) to remove last traces of hexamethyldisilazine. The solid thus obtained was dried under vacuo for 6 h. To a solution of 2,4-N,bis(trimethylsilyl)-5-azacytidine (10.0 mmol) in dry 1,2-dichlorethane (150 mL) was added 1-O-acetyl-2,3,5-tri-O-benzoyl-b-L-ribofuranose (5.06 g, 10 mmol) and tin tetrachloride (1.68 mL, 14.16 mmol) at 10° C. The reaction mixture was stirred under the atmosphere of argon at 10° C. for 2 h. The reaction was checked by TLC using hexane and ethyl acetate (7:3). TLC indicated that no starting material remained. The reaction mixture was diluted with dichloromethane (250 mL). The organic layer is washed with sat. sodium bicarbonate (200 mL) and brine (100 mL), dried over sodium sulfate and concentrated to a residue. The residue was dissolved in toluene and filtered through celite to remove unreacted 5-azacytosine. The filtrate was evaporated to dryness and the residue (5.20 g) was dissolved in ethanol and filtered again through celite. The titled compound was crystallized from the filtrate as needles 4.45 g (81%): mp 186–187° C.; $^1$H NMR (CDCl$_3$) δ4.62–4.66 (m, 3H, C$_4$H and C$_5$H), 6.01 (m, 3H, C$_1$H, C$_2$H and C$_3$H), 7.26–8.06 (m, 17H, NH$_2$ and PhH) and 8.48 (s, 1H, C$_6$H).

Example 26

4-Amino-1-β-L-ribofuranosyltriazin-2(1H)-one (5-Azacytidine, 43)

Compound 42 (4.0 g, 7.19 mmol) was dissolved in absolute methanol (60 mL), heated to the boiling and treated with 0.5 M sodium methoxide (20 mL, 10.0 mmol). The starting material rapidly dissolved and the solution immediately deposited the product. The mixture was kept for 4 h at room temperature and overnight in a refrigerator. The crystals are collected, washed with ice-cold methanol (10 mL) and dried under reduced pressure at room temperature. Yield 1.50 g (86%). Analytical sample was obtained by re-crystallization from water-acetone (1:1): mp 222–222° C.; $^1$H NMR (D$_2$O) δ3.78–3.97 (m, 2H, C$_5$H), 4.13 (m, 1H, C$_4$H), 4.20 (m, 1H, C$_3$H), 4.33 (m, 1H, C$_2$H), 6.31 (d, 1H, C$_1$H, J$_{1',2'}$=2.5 Hz) and 8.24 (s, 1H, C$_6$H). Anal. Calc. for C$_8$H$_{12}$N$_4$O$_5$ (244.20): C, 39.35; H, 4.95; N, 22.94. Found C, 34.09; H, 4.28; N, 22.98.

Example 27

1-(2',3',5'-Tri-O-benzoyl-β-L-ribofuranosyl)-6-azauridine (44)

6-Azauracil (1.36 g, 12.0 mmol), was suspended in a mixture of hexamethyldisilazine (50 mL) and ammonium sulfate (50 mg). The reaction mixture was refluxed at 135° C. for 6 h. Later, the solvents were removed in vacuo and the residue that obtained was co-evaporated twice from dry toluene (2×50 mL) to remove last traces of hexamethyldisilazine. The solid was dried in vacuo for 6 h and used in the next step of synthesis without further characterization. To a solution of the 2,4bis(trimethylsilyl)-6-azauridine (12.0 mmol) in dry 1,2-dichlorethane (60 mL) was added 1-O-acetyl-2,3,5-tri-O-benzoyl-L-ribofuranose (5.06 g, 10 mmol) and tin tetrachloride (1.68 mL, 14.16 mmol) at 10° C. The reaction mixture was stirred under the atmosphere of argon at room temperature for 6 h. The reaction was checked by TLC using hexane and ethyl acetate (7:3). TLC indicated no starting material remained. The reaction mixture was diluted with dichloromethane (250 mL). The organic layer is washed with cold sat. sodium bicarbonate (150 mL) and brine (100 mL), dried over sodium sulfate and concentrated to a white foam. The residue was dissolved in dichloromethane (100 mL) and filtered through celite to remove unreacted 6-azauracil. The filtrate was evaporated to a residue (4.50 g), dissolved in minimum amount of ehanol and filtered again through celite. The title compound was crystallized from the filtrate as needles to give 4.50 g (79%) of pure 44: mp 193–195° C.; $^1$H NMR (Me$_2$SO-d$_6$) δ4.47–4.67 (m, 3H, C$_5$,H), 4.71 (m, 1H, C$_4$,H), 5.85 (m, 1H, C$_3$,H), 5.93 (m, 1H, C$_2$,H), 6.38 (d, 1H, J$_{1',2'}$=2.56 Hz, C$_1$,H), 7.26–8.06 (m, 16H, C$_5$H and 12.32 (s, 1H, NH).

Example 28

1-β-L-Ribofuranosyl-6-azauracil (6-Azauridine 45)

Compound 44 (4.5 g, 7.95 mmol) was dissolved in absolute methanolic ammonia (60 mL) and placed in a steel bomb. The was heated at 100° C. for 16 h. Later, the reaction vessel was cooled to room temperature and the solvent was removed under vacuum. The residue that obtained was triturated with hot toluene (2×50 mL). The residue was dissolved in 95% ethanol and left at room temperature. The white solid crystals that were obtained was collected by filtration and dried in vacuo. Yield 1.75 g (89%): mp 151–153° C.; $^1$H NMR (Me$_2$SO-d$_6$) δ3.30–3.47 (m, 2H, C$_5$,H), 3.73 (m, 1H, C$_4$,H), 3.92 (m, 1H, C$_3$,H), 4.17 (m, 1H, C$_2$,H), 4.62, 4.98, 5.22 (3br s, 1H, 3 OH, D$_2$O exchangeable), 5.82 (d, 1H, C$_1$,H, J$_{1',2'}$=3.85 Hz), 7.48 (s, 1H, C$_5$H) and 11.20 (br s, 1H, NH). Anal. Calc. for C$_8$H$_{11}$N$_3$O$_6$ (245.19): C, 29.19; H, 4.52; N, 17.14. Found: C, 38.81; H, 4.58; N, 17.04.

Example 29

Diethyl imidazole-4,5-dicarboxylate (46)

Imidazole-4,5-dicarboxylic acid (7.55 g, 50.0 mmol) is dissolved in absolute ethyl alcohol (120 mL). The solution was cooled in an ice bath to 0° C. and bubbled dry HCl gas for 1 h. Later, the reaction mixture was refluxed at 80° C. for 7 h during which time all the starting material was consumed. The solvent was removed and the residue that obtained was dissolved in dichloromethane (200 mL) and the organic layer was neutralized with triethylamine. The organic layer was washed with cold water (100 mL) and brine (50 mL), dried over anhydrous sodium sulfate and concentrated in vacuo to give 5.50 g (52%) of white solid: mp 175–177° C.; $^1$H NMR (CDCl$_3$) δ1.40 (t, 3H), 4.41 (m, 2H), 7.84 (1H, C$_2$H) and 11.55 (br s, 1H, NH).

Example 30

Diethyl 1-(2',3',5'-tri-O-benzoyl-β-L-ribofuranosyl)imidazole-4,5-dicarboxylate (47)

A mixture of diethyl imidazole-4,5-dicarboxylate (2.65 g, 12.50 mmol) and ammonium sulfate (50 mg) was heated at reflux at 135° C. for 6 h with hexamethyldisilazine (50 mL). The reaction mixture was evaporated to dryness and the residue was co-evaporated twice with dry toluene (2×50 mL) to remove last traces of hexamethyldisilazine. The solid that obtained was dried in vacuo for 6 h and used for the next step without further characterization. To a solution of the above residue (12.5 mmol) in 1,2-dichlorethane (60 mL) was added 1-O-acetyl-2,3,5-tri-O-benzoyl-L-ribofuranose (5.06 g, 10 mmol) and tin tetrachloride (1.68 mL, 14.16 mmol) at 10° C. The reaction mixture was stirred under the atmosphere of argon at room temperature for 6 h. The reaction was checked by TLC using hexane and ethyl acetate (7:3). TLC indicated no starting material remained. The reaction mixture was diluted with dichloromethane (200 mL). The organic layer was washed with cold sat. sodium bicarbonate (200 mL) and brine (100 mL), dried over sodium sulfate and concentrated to yield a white foam. The residue was dissolved in dichloromethane (100 mL) and filtered through celite to remove tin salts. After evaporation in vacuo the residue (4.70 g) was dissolved in ethanol and filtered again through celite. The titled compound 47 was crystallized form the filtrate as needles. Yield 4.70 g (72%): mp 134–136° C.; $^1$H NMR (CDCl$_4$) δ1.28 (t, 3H, CH$_3$), 1.37 (t, 3H, CH$_3$), 4.28–4.40 (m, 4H, 2CH$_2$), 4.65–4.88 (m, 3H, C$_4$,H and C$_5$,H), 5.85 (m, 2H, C$_2$,H and C$_3$,H), 6.68 (d, 1H, C$_1$,H, J$_{1',2'}$=3.90 Hz) and 7.26–8.08 (m, 16H, C$_2$H and PhH).

Example 31

1-β-L-Ribofuranosylimidazole-4,5-dicarboxamide (48)

Compound 47 (4.0 g, 6.09 mmol) was dissolved in of absolute methanolic ammonia (60 mL) and heated at 100° C. for 16 h in a steel bomb. Later, the reaction mixture was cooled to room temperature. The product crystallized out from methanol. The precipitated product was removed by filtration and the filtrate was concentrated further to yield the second crop of the product. The combined product was recrystallized once again from methanol to furnish 1.68 g (100%) of white solid: mp 224–226° C.; $^1$H NMR (Me$_2$SO-d$_6$) δ3.53–3.75 (m, 2H, C$_5$,H), 3.84 (m, 1H, C$_4$,H), 3.96 (m, 2H, C$_2$,H and C$_3$,H), 4.97, 5.16, 5.36 (3br s, 3H, 3 OH, D$_2$O exchangeable), 6.49 (d, 1H, C$_1$,H, J$_{1',2'}$=2.1 Hz), 7.60 (s, 1H, CONH$_2$), 7.88 (s, 1H, CONH$_2$), 7.99 (s, 1H, CONH$_2$), 8.48 (s, 1H, C$_2$H) and 10.59 (s, 1H, CONH$_2$). Anal. Calc. for C$_{10}$H$_{14}$N$_4$O$_6$ (286.24): C, 41.96; H, 4.93; N, 19.57. Found: C, 41.89; H, 5.05; N, 19.41.

Example 32

Ethyl 1-(2',3',5'-tri-O-benzoyl-β-L-ribofuranosyl)-3-hydroxy-1,2-pyrazole-4-carboxylate A mixture of ethyl 3-Hydroxy-1,2-pyrazole-4-carboxylate (1.95 g, 12.50 mmol) and ammonium sulfate (50 mg) in hexamethyldisilazine (50 mL) was heated at reflux for 6 h. The reaction mixture was evaporated to dryness and the residue that obtained was co-evaporated twice with dry toluene (2×50 mL) to remove last traces of hexamethyldisilazine. The solid that obtained was dried in vacuo for 6 h and used as such for further reaction. To a solution of the above trimethylsilyl derivative (12.5 mmol) in dry 1,2-dichlorethane (60 mL) was added 1-O-acetyl 2,3,5-tri-O-benzoyl-L-ribofuranose (5.06 g, 10 mmol) and tin tetrachloride (1.68 mL, 14.16 mmol) at 10° C. The reaction mixture was stirred under the atmosphere of argon at room temperature for 6 h. The reaction mixture was diluted with dichloromethane (200 mL). The organic layer was washed with sat. sodium bicarbonate (200 mL), water (100 mL) and brine (100 mL), dried over sodium sulfate and concentrated to a foam. The residue was dissolved in dichloromethane (70 mL) and filtered through celite to remove tin salts. The crude product was purified by silica gel flash column chromatography using CH$_2$Cl$_2$→EtOAc as the eluent. Pure fractions were pooled and evaporated to give 3.50 g (57%) of a white foam: $^1$H NMR (CDCl$_3$) δ1.36 (t, 3H, CH$_3$), 4.30 (m, 2H, CH$_2$), 4.52–4.82 (m, 3H, C$_4$,H and C$_5$,H), 6.08–6.32 (m, 3H, C$_1$,H, C$_2$,H and C$_3$,H) and 7.26–8.08 (m, 16H, C$_5$H and PhH).

Example 33

1-β-L-Ribofuranosyl-3-hydroxy-1,2-pyrazole-4-carboxamide (50)

A solution of 49 (3.50 g, 5.71 mmol) in sat. methanolic ammonia (60 mL) was heated at 100° C. for 16 h in a steel bomb. The reaction mixture was cooled to room temperature and concentrated. The residue was triturated with toluene (2×50 mL) to remove benzamide. The residue was dissolved in minimum quantity of absolute ethanol and left at room temperature overnight. The crystals that obtained was removed by filtration and the filtrate was concentrated further to yield second crop of the product. The combined product recyrstallized once again from ethanol to the solid which was collected by filtration and dried in vacuo to yield 1.0 g (68%): mp 178–180° C.; $^1$H NMR (Me$_2$SO-d$_6$) δ3.37–3.52 (m, 2H, C$_5$·H), 3.78 (m, 1H, C$_4$·H), 3.98 (m, 1H, C$_3$·H), 4.19 (m, 1H, C$_2$·H), 4.81, 5.05, 5.34 (3br s, 3H, 3 OH, D$_2$O exchangeable), 5.38 (d, 1H, C$_1$·H, J$_{1',2'}$=4.2 Hz), 6.98 (bs, 1H, CONH$_2$), 7.16 (bs, 1H, CONH$_2$), 8.08 (s, 1H, C$_5$H) and 10.98 (bs, 1H, C$_3$OH). Anal. Calc. for C$_9$H$_{13}$N$_3$O$_6$ (259.22): C, 41.70; H, 5.05; N, 16.21. Found: C, 41.52; H, 5.23; N, 16.40.

Example 34

1-Azido-2,3-isopropylidine-b-L-ribofuranose (51)

To a solution 2,3,5-tri-O-benzoyl-1-azido-b-L-ribofuranose (9.0 g, 18.48 mmol) in absolute methanol (60 mL) was added 0.5 M solution of sodium methoxide (10.0 mL, 5.0 mmol). The reaction mixture was stirred at room temperature overnight. TLC of the reaction (hexane/ethyl acetate; 7:3) indicated complete conversion of the starting material to a more polar compound. The reaction mixture was neutralized with dry Dowex 50 H$^+$ resin and the resin was removed by filtration. The filtrate was evaporated to dryness and dissolved in water (50 mL). The aqueous layer was extracted with dichloromethane (2×100 mL) to remove methyl benzoate and then the aqueous layer was concentrated in vacuo. The residue was further dried over phosphorous pentoxide and used as such for the next step of the synthesis without further characterization.

The above crude product (3.0 g, 17.14 mmol) was suspended in dry acetone (200 mL) and treated with 1,1-dimethoxypropane (50 mL) and vacuum dried Dowex 50 H$^+$ (5.0 g) resin. The reaction mixture was stirred at room temperature for 2 h and filtered and the resin was washed with dry acetone (100 mL). The filtrate was evaporated to dryness. The residue was purified by flash chromatography over silica gel using CH$_2$Cl$_2$→EtOAc as the eluent. The pure fractions were pooled and concentrated to give 3.60 g (97%)of product as oil: $^1$H NMR (CDCl$_3$) d, 1.44 and 1.27 (2s, 6H, isoporpylidene CH$_3$), 2.70 (br s, 1H, C$_5$·OH, exchangeable), 3.66 (m, 2H, C$_5$·H), 4.34 (m, 1H, C$_4$·H), 4.46 (d, 1H, C$_3$·H), 4.72 (d, 1H, C$_2$·H) and 5.50 (s, 1H, C$_1$·H).

Example 35

1-Azido-2,3-O-isopropylidine-5-O-tert-butyldimethylsilyl-b-L-ribofuranose (52)

To a solution of 1-azido-2,3-O-isopropylidine-b-L-ribofuranose (4.20 g, 20 mmol) in dry DMF (25 mL) was added imidazole (2.38 g, 35.0 mmol) and tert-butyldimethylsilyl chloride (4.50 g, 30.0 mmol). The reaction mixture was stirred at room temperature under argon atmosphere overnight. TLC of the reaction mixture was stirred at indicated complete conversion of the starting material to the product. The solvent was removed in vacuo and the residue dissolved in dichloromethane (200 mL). The organic layer is washed with water (100 mL), satd. sodium bicarbonate (100 mL) and brine (100 mL), dried over sodium sulfate and concentrated to an oily product. Further purification by silica gel flash column chromatography using hexane/ethyl acetate (9:1) gave 6.22 g (94%) of the titled compound as oil: $^1$H NMR (CDCl$_3$) d 0.07 (s, 6H), 0.9 (s, 9H), 1.27 and 1.47 (2s, 6H, isopropylidene CH$_3$), 3.66 (m, 2H, C$_5$·H), 4.34 (m, 1H, C4'H), 4.46 (d, 1H, C$_3$·H), 4.72 (d, 1H, C$_2$·H) and 5.50 (s, 1H, C$_1$·H).

Example 36

1-Amino-2,3-O-isopropylidine-5-O-tert-butyldimethylsilyl-β-L-ribofuranose (53)

To a mixture of 1-azido-2,3-O-isopropylidine-β-L-ribofuranose (6.0 g, 18 mmol) and Pd/C (0.25 g) in MeOH (50 mL) was hydrogenated at 50 psi on a parr hydrogenator overnight. The reaction mixture was filtered and the catalyst washed with methanol(20 mL). The combined filtrate was evaporated to dryness and dried over P2O5 at vacuo overnight and used as such for the next reaction without characterization. Yield 5.0 g (90%).

Example 37

Ethyl 5-amino-(2',3'-O-isopropylidine-5'-O-tert-butyldimethylsilyl-β-L-ribofuranosyl)imidazole-4-carbozylate (54)

To a stirred solution of 53 (5.0 g, 16.44 mmol) in dry CH$_2$Cl$_2$ (60 mL) was added a solution of ethyl N-cyano-N-(ethoxycarbonylmethyl)formimidate (4.0 g, 22.18 mmol; Robinson, D. H., et al, J. Chem Soc., Perkin 1, 1715–1717, 1972) during 15 min period. The reaction mixture was stirred at room temperature overnight under argon atmosphere. The reaction was diluted with CH$_2$Cl$_2$ (100 mL) and the organic layer was washed with sat. NaHCO3 (100 mL), water (50 mL) and brine (50 mL). The organic extract was dried and concentrated to give a crude product. The crude product was purified by flash chromatography over silica gel using CH$_2$Cl$_2$→EtOAc as the eluent. The pure fractions were pooled and evaporated to five 5.50 g (76%) as white foam: $^1$H NMR (CDCl$_3$) δ0.28 (m, 6H), 1.1 (m, 9H), 1.55 (m, 9H), 4.00 (m, 2H, C$_5$·H), 4.53 (m, 3H), 5.0 (m, 1H), 5.78 (m, 1H), 6.06 (d, 1H, C$_1$·H) and 7.44 (s, 1H, C$_2$H).

Example 38

5-amino-(2',3'-O-isopropylidine-5'-O-tert-butyldimethylsilyl-β-L-ribofuranosyl)imidazole-4-carboxamide (55)

A solution of 54 (5.0 g, 11.33 mmol) in methanolic ammonia (60 mL) was heated at 100° C. in a steel bomb for 12 h. The steel bomb was cooled, opened carefuilly and concentrated. The crude product was purified by flash chromatography over silica gel using CH$_2$Cl$_2$→EtOAc as the eluent. The pure fractions were pooled and evaporated to give 4.0 g (88%) as white foam.

Example 39

5-Amino-(2',3'-O-isopropylidine-β-L-ribofuranosyl)imidazole-4-carboxamide (56)

To a stirred solution of 55 (4.0 g, 9.97 mmol) in dichloromethane (50 mL) was added Et$_3$N.3HF (50 mmol) at room temperature. The reaction mixture was stirred overnight and evaporated to dryness. The residue was purified by flash chromatography over silica gel using $CH_2Cl_2 \rightarrow EtOAc$ as the eluent. The pure fractions were pooled and evaporated to give 2.10 g (71%) as white foam.

Example 40

5-Amino-1-β-L-ribofuranosylimidazole-4-carboxamide (57)

To a stirred solution of 56 (2.0 g, 6.71 mmol) in dichloromethane (20 mL) was added 90% $CF_3COOH$ (20 mL) at 0° C. The reaction mixture was stirred at 0° C. for 1 h and evaporated to dryness. The residue was coevaporated with dry methanol (20 mL). This process was repeated three times to remove last traces of TFA. The residue was treated with $NH_4OH$ (10 mL) and evaporated to dryness. The residue was evaporated with dry ethanol (3×20 mL). The residue was crystallized from ethanol to give 1.5 g (87%) of pure product.

Example 41

Methyl 1-β-L-(2',3',5'-Tri-O-benzoyl)ribofuranosyl-2-oxo-$\Delta^4$-imidazoline-4-carboxylate (59)

A mixture of methyl 2-oxo-$\Delta^4$-imidazoline-4carboxylate 58 (542 mg, 8.82 mmol), hexamethyldisilazane (HMDS, 28 mL) and $(NH_4)_2SO_4$ (75 mg, 0.56 mmol) were heated at reflux. A clear sulution formed in 40 min and the reaction was maintained at reflux for another 3.5 h. The excess HMDS was evaporated and the product, a brown oil further dried under vacuum for 1 h.

A solution of 1-O-acetyl-2,3,5-O-tri-benzoyl-L-ribofuranose (1.93 g, 3.82 mmol) in anhydrous dichloroethane (28 mL) was added to the above dried silyl base at room temperature followed by dropwise addition of $SnCl_4$ (1.39 g, 0.63 mL, 5.35 mmol). After addition, the reaction mixture was allowed to stay at room temperature overnight (17 h). The reaction mixture was filtered through a silica gel pad flushed with EtOAc. The EtOAc solution was washed with sat. $NaHCO_3$, filtered, washed with brine twice. The organic phase was separated dried over $Na_2SO_4$, concentrated, and purified by flash chromatography over silica gel using (86% $CH_2Cl_2$, 14% EtOAc) to give 797 mg (36%) of the product as an off-white solid: $^1H$ NMR ($Me_2SO-d_6$) δ3.70 (m, 2H), 4.60 (dd, 1H, $J_{1',2'}=12.7$, 6.6 Hz,), 4.70 (m, 2H), 5.93 (dd, 1H, 5.98 (d, 1H), 6.05 (dd, 1H), 7.46 (m, 6H), 7.63 (m, 3H), 7.71 (s, 1H), 7.91 (m, 6H) and 11.15 (s, 1H).

Example 42

1-β-L-Ribofuranosyl-2-oxo-$\Delta^4$-imidazoline-4-carboxamide (60)

Compound 59 (1.26 g, 2.15 mmol) was dissolved in methanolic ammonia (45 mL, pre-saturated with $NH_3$ at 0° C.). The solution was sealed in a steel bomb and heated at 95° C. for 15 h. The reaction mixture was cooled to room temperature, the solvent was evaporated, and the residue washed with $CHCl_3$ three time to remove the benzamide generated from the reaction. The residue was then added with MeOH (15 mL) and heated at reflux. $CHCl_3$ was added to the clear solution at reflux slowly until trace of precipitate generated. The hot mixture was filtered quickly by suction and the filtrate solution was evaporated to dryness to give a light brown oil. The oil was soaked with anhydrous $CH_3CN$ afforded the product as a light brown solid: Yield 322 mg (58%); mp 174–178° C. $^1H$ NMR ($Me_2SO-d_6$) δ3.48 (m, 2H), 3.77 (m, 1H), 3.94 (m, 1H), 4.05 (m, 1H), 4.90 (m, 1H), 5.08 (d, 1H), 5.30 (d, 1H), 5.36 (d, 1H), 7.30 (s, 1H), 7.31 (br s, 2H) and 10.47 (br s, 1H).

Example 43

2,3,5-Tri-O-benzoyl-β-L-ribofuranosyl-1-carbonitrile (61)

To a stirred mixture of 1-O-acetyl-2,3,5-tri-O-benzoyl-β-L-ribofuranose (dried at 60° C., 1 mm, 12 h; 12.6 g, 24.9 mmol) in dry dichloromethane (dried over magnesium sulfate and stored over molecular sieves, 125 mL) at 0–2° C. was added trimethylsilyl cyanide (dried over molecular sieves, 24 h; 4.70 mL, 37.50 mmol) under argon atmosphere. To this reaction mixture was then added stannic chloride (1.0 mL, 8.67 mmol) slowly while maintaining a reaction temperature at 0–2° C. The resulting mixture was stirred and maintained at −5 to 0° C. for an additional 1.5 h. After 2 h, the reaction mixture was added slowly into a vigorous stirring cold (5° C.) 10% sodium hydroxide solution (1.5 L) during 30 min period and the mixture was maintained at 5–8° C. throughout the addition. The layers were separated and the organic layer was washed with water (3×500 mL) until neutral and then dried over anhydrous magnesium sulfate. The organic extract was filtered and the drying agent was washed with dichloromethane (3×50 mL). The filtrate and washings were combined and the solution was concentrated (<30° C., 20 mm) to a low volume and the remaining solution was filtered through a bed of celite. Further purification was achieved by silica gell flash column using dichloromethane as eluent. The dichloromethane solutions were combined and evaporated (<30° C., 20 mm) to give a white foam. The crude product was purified by flash chromatography over silica gel using dichloromethane as the eluent. The pure fractions were combined and evaporated to give a syrup. The syrup was mixed with dry ethanol (100 mL) and the mixture was heated (approx. 60° C.) to obtain a homogeneous solution. Cooling of this solution to room temperature gave white crystalline product. The crystalline solid was filtered and washed with cold ethanol and dried over $P_2O_5$ to give 7.47 g (63%) of 61: mp 55–57° C.; $^1H$ NMR ($CDCl_3$) δ4.61 (m, 1H, $C_4$·H), 4.78 (m, 2H, $C_5$·H), 5.00 (d, 1H, $C_1$·H), 5.88 (t, 1H, $C_3$·H), 6.05 (m, 1H, $C_2$·H), 7.45–8.07 (m, 15H, PhH).

Example 44

2,3,5-Tri-O-benzoyl-β-L (+)-ribofuranosyl allonthioamide (62)

To a suspension of L-cyanosugar 61 (6.10 g, 12.95 mmol) in dry ethanol (105 mL) was passed $H_2S$ for 10 min. To this solution was then added N,N-dimethylaminopyridine (DMAP, 158 mg, 1.3 mmol). The reaction was kept at 15–20° C. and sat. with $H_2S$ during 2½ h period. (Note: The starting material which was a suspension was dissolved during the course of reaction). After 2½ h, the $H_2S$ bubbling was stopped, the reaction mixture was stoppered and allowed to stir at room temperature overnight. The reaction was checked by TLC next day morning (Hexane/EtOAc; 7:3). TLC indicated complete conversion of the starting material to the allothioamide. The reaction mixture was cooled on an ice bath and argon was bubbled through this for 1 h to remove the excess $H_2S$. Later the reaction mixture was concentrated on a rotavapor to yield 6.20 g (95%) of a foamy material: $^1$H NMR (CDCl$_3$) δ4.78 (m, 3H, C$_4$·H and C$_5$·H), 5.12 (d, 1H, C$_1$·H), 5.72 (t, 1H, C$_3$·H), 5.98 (m, 1H, C$_2$·H), 7.45–8.12 (m, 15H, PhH) and (8.50 (br s, 2H, NH$_2$).

Example 45

Ethyl 2-(2',3',5'-Tri-O-benzoyl-β-L(+)-ribofuranosyl)thiazole-4-carboxylate (63)

To a stirred suspension of allothioamide 62 (5.05 g, 10 mmol) in dry 1,2-dimethoxyethane (DME, 100 mL) at 0° C. was added of anhydrous NaHCO$_3$ (8.4 g, 100 mmol). To this suspension under argon was added of ethylbromopyruvate (3.75 mL, 30 mmol) dropwise during 10 min period. The reaction mixture was stirred at 0° C. for 5 h under argon. The reaction was analyzed by TLC (Hex/EtOAc; 7:3). TLC indicated traces of starting material. The reaction was left additional 1 h at 0–5° C., by which time most of the starting material was converted into the product. Then, the reaction mixture was cooled to −15° C. in dry ice/acetone bath. To the reaction mixture was then added dropwise through a dropping funnel a solution of 2,6-lutidine (7.0 mL, 60 mmol) and trifluoroacetic anhydride (4.16 mL, 30 mmol) in dry DME (20 mL) during 15 min period. The reaction mixture temperature was maintained at −15° C. for 2 h under argon. Then, the reaction mixture was filtered and concentrated. The residue that obtained was dissolved in CH$_2$Cl$_2$ (200 mL) and the organic layer was washed with 5% NaHCO$_3$ (100 mL), 1N HCl (100 mL), 5% NaHCO$_3$ (100 mL), water (100 mL) and brine 100 mL), dried and concentrated to a dark red color oil. The crude product was purified by silica gel flash column chromatography using hexane/EtOAc (7:3) as the eluent gave 5.96 g (99%) of pure product: $^1$H NMR (CDCl$_3$) δ1.30 (t, 3H, CH$_2$CH$_3$), 4.30 (t, 2H, CH$_2$CH$_3$), 4.55–4.78 (m, 3H, C$_4$·H) and C$_5$·H), 5.71 (d, 1H), 5.82 (m, 2H), 7.25–8.04 (m, 15H, PhH) and 8.06 (s, 1H, C$_5$·H).

Example 46

β-L (+)-Ribofuranosylthiazole-4-carboxylic acid ethyl ester (64)

Compound 63 (6.0 g, 10 mmol) was dissolved in dry ethanol (60 mL) (Note: the compound was dissolved by warming with hot air gun). To this solution under argon was added NaOEt (200 mg, 3.0 mmol) powder. The reaction mixture was stirred under argon overnight. The reaction was checked by TLC using hexane/EtOAc 7:3 and EtOAc/MeOH 9:1). TLC has indicated complete conversion of the starting material to a more polar product. Then, the reaction was neutralized with dry Dowex 5x-8 H$^+$ resin. The resin was removed by filtration and the filtrate was concentrated under vacuum on a rotavapor. The brown colored residue was then purified by silica gel flash column chromatography using EtOAc→MeOH. The pure fractions were pooled and concentrated to furnish 2.31 g (77%) of pure product. $^1$H NMR (CDCl$_3$) δ1.30 (t, 3H, CH$_2$CH$_3$), 3.56 (m, 2H, C$_5$·H), 3.86 (m, 2H), 4.0 (m, 1H), 4.26 (t, 2H, CH$_2$CH$_3$), 4.82–5.04 (3m, 3H, 3 OH), 5.42 (d, 1H, C$_1$·H) and 8.46 (s, 1H, C$_5$·H).

Example 47

β-L(+)-Ribofuranosylthiazole-4-carboxamide (65)

A solution of 64 (1.0 g, 3.32 mmol) in methanolic ammonia (50 mL) was stirred at room temperature in a steel bomb. After 17 h, the bomb was cooled, opened carefully and the solution was evaporated to a residue. The residue was chromatographed on a silica gel flash column chromatography using ethyl acetate and methanol (9:1) as the eluent. The product is crystallized from absolute ethanol. Yield 580 mg (67%): mp 146–148° C.; $^1$H NMR (Me$_2$SO-d$_6$) δ3.48 (m, 2H, C$_5$·H), 3.85 (m, 2H), 4.03 (m, 1H), 4.80 (t, 1H, C$_5$·OH), 4.88 (d, 1H, C$_3$·OH), 5.32 (d, 1H, C$_2$·OH), 5.02 (d, 1H, C$_1$·H, J$_{1',2'}$=5.1 Hz), 7.52 (bs, 1H, CONH$_2$), 7.64 (bs, 1H, CONH$_2$) and 8.16 (s, 1H, C$_5$H). Anal calc. for C$_9$H$_{12}$N$_2$SO$_5$ (260.2): C, 41.53; H, 4.65; N, 10.76; S, 12.32. Found: C, 41.73; H, 4.60; N, 10.55; S, 12.25.

Example 48

β-L-Ribofuranosyl-1-carboximidic Acid Methyl Ester (66)

To a stirred suspension of 2,3,5-tri-O-benzoyl-β-L-ribofuranosyl cyanide (14.13 g, 30.0 mmol) in dry methanol (60 mL) was added sodium methoxide (0.358 g, 6.64 mmol, 0.5 M solution, Fluka) under argon atmosphere. The solution, which became homogeneous in 5 min, was stirred for 2.5 h at room temperature. The reaction mixture was neutralized with Dowex 50W-X8 H$^+$ resin (dried at 100° C. under 0.05 mm Hg 16 h; 3.0 g, 5.1 molar equiv/g). The resin was filtered and the solvent was removed below 40° C. on a rotavapor. The residue that obtained was washed with methanol. The methanol washings were concentrated to obtain second and third crops of 66. The three crops were combined and recyrstallized from dry methanol to provide 4.35 g (66%): mp 140–142° C.; $^1$H NMR (CDCl$_3$) δ3.46 (s, 3H, OCH$_3$), 3.5–3.80 (m, 5H), 3.98 (d, 1H), 4.98 (br s, 3H) and 8.27 (s, 1H, NH).

Example 49

2-[(Aminocarbonyl)carbonyl]-1-(β-L-ribofuranosyliminomethyl)hydrazine (67)

Methyl imidate 66 (4.83 g, 25.26 mmol) and oxamidohydrazide (2.68 g, 26.00 mmol) were dissolved in dry dimethyl sulfoxide (100 mL). After the reaction solution was stirred for 20 h at room temperature, the solvent was distilled off at 55° C. in vacuo. The residual solid was suspended in methanol, and the soluble portion was collected by filtration (the insoluble solid was found to be unreacted hydrazide) and concentrated to about 25 mL. Addition of this solution drop-wise into acetonitrile (500 mL) a white precipitate was obtained: yield 4.35 g (66%); $^1$HNMR (Me$_2$SO-d$_6$) δ3.47–3.60 (m, 2H), 3.3.60–3.88 (m, 3H), 4.07 (d, 1H), 4.15 (d, 1H), 4.85–5.2 (br s, 2H), 7.70, 8.09 (2 br s, 2H) and 10.05 (br s, 1H, C=NH).

Example 50

3-β-L-Ribofuranosyl-1,2,4-triazole-5-carboxamide (C-Ribavirin; 68)

Compound 67 (4.0 g, 15.2 mmol) was heated under vacuum (0.1 mm) at 135° C. for 15 min. After the flask was cooled, the glassy material was treated with methanol and heated on a steam bath. During this process a solid started to precipitate. After about 2 h, the solid was isolated, and a second crop was obtained on concentration of the filtrate. The total yield of the product was 2.65 g (71%): mp 193–195° C.; $^1$H NMR (Me$_2$SO-d$_6$) δ3.43 (m, 2H, C$_5$·H), 3.75 (m, 1H, C$_4$·H), 3.88 (m, 1H, C$_3$·H), 4.12 (m, 1H, C$_2$·H), 4.57 (d, 1H, C$_1$·H, J$_{1',2'}$=5.7 Hz), 7.62 (bs, 1H, CONH$_2$), 7.86 (bs, 1H, CONH$_2$) and 10.0 (bs, 1H, NH), Anal. Calc. for C$_8$H$_{12}$N$_4$O$_5$ (244.2): C, 39.35; H, 4.95; N, 22.94. Found: C, 39.38; H, 4.73; N, 22.43.

Example 51

5-O-Trityl-2,3-O-isopropylidene-b-L-ribofuranose (69)

To a solution of 2,3-O-isopropylidene-b-L-ribofuranose (10.5 g, 55.26 mmol) in dry pyridine (100 mL) under argon was added catalytic amount of DMAP (12.2 mg, 0.1 mmol). To this stirred solution was then added trityl chloride (15.56 g, 56.0 mmol). The reaction mixture was stirred under argon atmosphere overnight at room temperature. Pyridine was removed under vacuum and the residue was dissolved in $CH_2Cl_2$ (250 mL) and the organic layer was washed with 10% $NaHCO_3$ solution (2×100 mL) and brine (100 mL). The organic layer was dried over $Na_2SO_4$ and concentrated in vacuo. The residue that obtained was purified by silica gel flash column using Hexane→EtOAc as the eluent. Pure fractions were pooled and concentrated to give 15.74 g (69%) of product: $^1$H NMR ($CDCl_3$) δ1.27 and 1.41(2s, 6H, isopropylidene $CH_3$), 3.25–3.56 (m, 2H, $C_5H$), 3.86 (m, 2H), 4.0 (m, 1H), 4.70 (m, 1 H), 5.24 (d, 1H, $J_{1',2'}$=3.50 Hz, $C_1H$) and 7.17–7.35 (m, 15H, PhH).

Example 52

3-Ethoxycarbonyl-2-oxopropylidenetriphenylphosphorane (70)

A solution of {3-(ethoxycarbonyl)-2-oxopropyl}triphenyl phosphonium chloride (21.34 g, 500 mmol) in water (450 mL) was added to a solution of sodium carbonate (3.1 g, 25.0 mmol) in 10 min (Note: A white precipitate was obtained immediately after the addition). This reaction mixture was stirred at room temperature overnight. The precipitate that obtained was filtered off through a sintered funnel. The precipitate was dissolved in dichloromethane (100 mL), dried over sodium sulfate and concentrated to yield a white solid 18.13 g (93%). This material was dried over phosphorus pentoxide overnight. $^1$H NMR ($CDCl_3$) δ1.26 (t, 3H), 3.34 (s, 2H), 3.76–3.84 (d, 1H) 4.19 (m, 2H) and 7.48–7.68 (m, 15H, PhH).

Example 53

Ethyl 4-(2',3'-O-Isopropylidene-5'-O-trityl-α-and β-L-ribofuranosyl)-3-oxobutanoate (71)

A mixture 70 (10.9 g, 25.23 mmol) and 3-ethoxycarbonyl-2-oxopropylidenetriphenyl-phosphorane (11.8 g, 30 mmol) in anhydrous acetonitrile (30 mL) was refluxed for 90 h. The solvent was evaporated under reduced pressure and the residue was subjected to a silica gel flash column chromatography. Elution with hexane-ethyl acetate (9:1) gave the product (β:α ca.2:1) as a foam (10.15 g, 74%).

Example 54

Ethyl 2-Diazo-4-(2',3'-O-isopropylidene-5'-O-trityl-α- and -β-L-ribofuranosyl)-3-oxobutanoate (72)

Triethylamine (1.83 g, 18.1 mmol) and toluene-p-sulphonyl azide (10 mL) were sequentially added to a solution of 71 (9.85 g, 18.08 mmol) in anhydrous acetonitrile (50 mL). The mixture was kept at room temperature for 30 min. The solvent was then evaporated under reduced pressure and the residue was subjected to a silica gel flash column chromatography. Elution with hexane-ethyl acetate (9:1) gave 8.90 g (86%) of 72 (β:α ca. 1:1) as a foam.

Example 55

Ethyl 4-hydroxy-3-(2',3'-O-isopropylidene-5'-O-trityl-β-L-ribofuiranosyl)pyrazole-5-carboxylate (73)

A solution of 72 (8.53 g, 14.92 mmol) in dry DME (60 mL) was added dropwise to a stired ice-cold suspension of sodium hydride (NaH) (60% dispersion; 1.80 g, 75.0 mmol) in dry DME (60 mL) under argon during 30 min. The reaction temperature was raised gradually to 20° C., and the mixture was stirred additional 3 h at room temperature. The reaction mixture was analyzed by TLC using hexane/EtOAc (3:1) or dichloromethane/EtOAc (9:1). TLC indicated completion of the reaction. A solution of acetic acid (4.50 mL, 75.0 mmol) in DME (10 mL) was then added dropwise to the stirred ice-cold reaction mixture. The solvent was evaporated under reduced pressure to give a residue to which water (50 mL) and diethyl ether (100 mL) were added. The ethereal layer was separated, dried over anhydrous sodium sulfate and concentrated. The residue was subjected to silica gel flash column chromatography with hexane-ethyl acetate (3:1) as the eluent. Pure fractions were collected and evaporated to give 73 as a mixture of β:α (6.40 g, 73%): $^1$H NMR ($CDCl_3$) δ1.31 (t, 3H), 1.42–1.65 (m, 6H), 3.19–3.27 (m, 2H), 4.44–4.75 (m, 3H), 4.75 (m, 1H), 5.19 (d, 1H), 6.99 (br s, OH, exchangeable), 7.26–7.51 (m, 15H, PhH).

Example 56

4-Hydroxy-3-(2',3'-O-isopropylidene-5'-O-trityl-β-L-ribofuranosyl)pyrazole-5-carboxamide (74)

A solution of the ester 73 (6.30 g, 10.7 mmol) in dry methanolic ammonia (70 mL) was heated at 90–95° C. in a steel bomb for 12 h. The solvent was evaporated under reduced pressure and the residue was subjected to silica gel flash column chromotography using hexane/ethyl acetate (3:2) as the eluent. The required fractions were pooled and evaporated to give 4.54 g (78%) of the product as a glass containing a mixture of β:α. $^1$H NMR ($CDCl_3$) δ1.40–1.62 (2s, 6H), 3.11–3.24 (m, 2H), 4.37 (m, 1H), 4.65 (m, 1H), 5.11 (dd, 1H), 5.27 (d, 1H), 6.99 (br s, OH, exchangeable) and 7.23–7.50 (m, 17H).

Example 57

3-β-L-Ribofruanosyl-4-hydroxypyrazole-5-carboxamide (L-Pyrazomycin; 75)

A solution of 74 (4.40 gm, 8.13 mmol) in 90% $CF_3CO_2H$ (20 mL) was stirred at room temperature for 45 min. Then the solvent was removed at 5° C. under reduced pressure to give white solid (1.90 g, 90.48%). The residue that obtained was chromatographed on silica gel flash column with EtOAc-iPrOH-$H_2O$ (4:1:2) as the eluent. Fractions containing the pure compound b and a isomers were pooled separately and evaporated at <20° C. Recrystallization from water afforded 800 mg of pure β isomer: mp 111–113° C.; $^1$H NMR of β isomer ($D_2O$) δ3.73–3.78 (m, 2H), 4.0 (m, 1H), 4.19 (m, 1H), 4.35 (m, 1H) and 4.90–4.93 (d, 1H, $J_{1',2'}$=7.42 Hz). Anal. Calc. for $C_9H_{13}N_3O_6$ (259.22): C, 41.70; H, 5.05; N, 16.21. Found: C, 41.88; H, 5.04; N, 16.58. Isolated yield of α:β mixture 1.90 g, (90%).

100 mg of isomer was isolated as foam; $^1$H NMR of α isomer ($D_2O$) δ3.65–3.85 (m, 2H), 4.06–4.11 (m, 1H), 4.32–4.41 (m, 2H), and 5.20 (d, 1H, $J_{1',2'}$=3.30 Hz). Anal. Calc. for $C_9H_{13}N_3O_6$: C, 41.70; H, 5.05; N, 16.21. Found: C, 41.91; H, 5.08; N, 16.02.

1.0 gm of inseparable mixture of L-pyrazomycin was also isolated.

The purity of the α:β isomers is also established by C18 reverse phase HPLC using the gradient of acentonitrile 0–10% in water. The retention time of α isomer is Rt 5.716 and the β isomer 7.135. The purity of β and α mixture of L-pyrazomycin is found to be greater than 99.0% by HPLC.

Example 58

Preparation of 2,5-Anhydro-L-alloamidine hydrochloride (76)

Methyl 2,5-anhydro-L-allonimidate (3.82 g, 20.0 mmol) and ammonium chloride (1.07 g, 20.0 mmol were dissolved in methanolic ammonia (60 mL, saturated at dry ice-acetone temperature for 1 h). Later this mixture was allowed stir at room temperature in a thick walled steel bomb for 16 h at room temperature. The steel bomb was cooled, opened carefully and the solution was evaporated to dryness. The resulting solid was dried to yield 4.10 g of the titled compound in quantitative yield.

Example 59

2-(β-L-Ribofuranosyl)pyrimidine-6(1H)-oxo-4-carboxylic acid (77)

To a solution of 2,5-anhydro-L-alloamidine hydrochloride (4.0 g, 18.66 mmol) in water (60 mL) was added sodium hydroxide (1N, 20 mL, 20.0 mmol) and ethyl sodium oxaloacetate (4.20 g, 20.0 mmol). The reaction mixture was allowed to stir room temperature at 16 h at room temperature and was subsequently neutralized to pH 2 with $H^+$ resin (Dowex 50W-X8). The reaction mixture was filtered and concentrated to a minimum volume. Silica gel was added and evaporated to dryness. The resultant powder was placed on the top of a flash column and eluted with ethyl acetate/acetone/methanol/water (3/1/1/1) mixture until the faster moving compound was eluted. The column was then eluted with methanol and the fractions containing the compound were pooled and the methanol was removed to yield artan color hygroscopic compound. Isolated yield 4.50 g (89%). This compound was used as such for the next step without characterization.

Example 60

Ethyl 2-(β-L-Ribofaranosyl)pyrimidine-6(1H)-oxo-4-carboxylate (78)

A thoroughly dried suspension of the acid 77 (4.50 g, 16.5 mmol) in of dry ethanol (100 mL) was cooled in an ice bath and dry hydrogen chloride gas was bubbled for 5 min. To this reaction mixture was added triethyl orthoformate (20 mL) and the mixture was allowed to stir for 24 h at room temperature. The solvent was removed under vacuum and the resultant dark colored solid was purified further by silica gel flash column chromatography using dichloromethane/methanol (9/1) mixture. Pure fractions were pooled and concentrated to yield 4.55 g (92%) of a solid compound. Since this compound was found to be impure, it is further converted to the corresponding tetra acetate in 47% yield. The tetra acetate was purified by column chromatography.

Example 61

2-(β-L-Ribofuranosyl)pyrimidine-6(1H)-oxo-4-carboxamide (79)

A solution of the above tetra acetate ester (1.80 g, 4.22 mmol) in sat. methanolic ammonia (60 mL) was heated at 100° C. in a steel bomb for 17 h. The reaction mixture was cooled and concentrated to yield a white solid. The solid was further triturated with ethyl acetate and filtered. The solid was recyrstallized from absolute ethanol to provide 0.83 g (82%) of pure product as white solid: mp 200–202° C.; $^1$H NMR (Me$_2$SO-d$_6$) δ3.35–3.57 (m, 2H, C$_5$.H), 3.84 (m, 1H, C$_4$.H), 3.98 (m, 1H, C$_3$.H), 4.22 (m, 1H, C$_2$.H), 4.75 (t, 1H, C$_5$.OH, D$_2$O exchangeble), 4.80 (d, 1H, C$_1$.H, J$_{1',2'}$=5.77 Hz), 4.89 (d, 1H, C$_3$.OH, D$_2$O exchangeable), 5.15 (d, 1H, C$_2$.OH, D$_2$O exchangeable), 7.85 (d, 1H), 7.98 (bs, 1H, CONH$_2$), 8.19 (bs, 1H, CONH$_2$) and 9.0 (d, 1H, NH). Anal. Calc. for C$_{10}$H$_{13}$N$_3$O$_4$ (239.23): C, 44.28; H, 4.83; N, 15.49. Found: C, 44.58; H, 5.17; N, 15.28.

Example 63

Methyl β-L-arabinopyranoside (81)

To a suspension of L-arabinose (100 g, 667 mmol) in anhydrous MeOH (450 mL ) was added a HCl/MeOH solution (7.3 g dry HCl in 50 mL MeOH) at room temperature under argon atmosphere. The mixture was refluxed for 2 h and cooled down to room temperature. The solution was concentrated to about ¾ of its volume to give a suspension. The solid precipitated was filtered and washed with cold MeOH (20 mL) to give the first crop as a crystalline powder (35.23 g). The filtrate was concentrated (35° C.) to ¼ of its volume. The solid precipitated was filtered, washed and dried as above to give the second crop (9.66 g) as a colorless crystalline powder. The concentration and filtration were repeated to afford additional 28.31 g of the product (total 73.2 g, 67%). $^1$H NMR (D$_2$O) δ3.30 (s, OCH$_3$, 3H), 3.56 (dd, 1H, H$_5$), 3.73 (m, 1H, H$_4$), 3.77 (dd, 1H, H$_5$), 3.82 (bs, 1H, H$_2$), 4.73 (m, 1H, H$_1$).

Example 63

Methyl 3,4-isopropylidene-β-L-arabino-pyranoside (82)

To the mixture of methyl β-L-arabinopyranoside 81 (23.33 g, 142.26 mmol) and dimethoxypropane (55 mL, 448 mmol) in dry DMF (185 mL) was added Amberlyst 15 (H+ form, 1.42 g) and the suspension was stirred at room temperature for 18 h. The solution was evaporated to give a syrup, which was dissolved in EtOAc (200 mL) and washed with brine (50 mL), sat. NaHCO$_3$ solution and brine (20 mL). The aqueous washings were combined and extracted with EtOAc (5×20 mL), which was washed with NaCl/H$_2$O and combined with the organic solution. The EtOAc solution was dried over anhydrous Na$_2$SO$_4$ and evaporated to dryness to give a syrup (29.2 g, quant.). $^1$H NMR (CDCl$_3$) δ1.36 and 1.53 (2s, 6H, isopropylidene-CH$_3$), 2.43 (d, 1H, 2'-OH), 3.44 (s, 3H, OCH$_3$), 3.78 (m, 1H, H$_2$), 3.93 (s, 2H, H$_5$), 4.15–4.25 (m, 2H, H$_3$ & H$_4$), 4.71 (d, 1H, H$_1$).

Example 64

Methyl 3,4-isopropylidene-2-o-[(methylthio)thiocarbonyl]-β-L-arabino-pyranoside (83)

The above syrup 82 (29.2 g, 142.26 mmol) was dissolved in anhydrous THF (190 mL) and cooled to 0° C. To the solution was added NaH (55–65%, 6.9 g, 172.5 mmol) slowly under argon atmosphere. The suspension was refluxed for 2 h and cooled to 0° C. To the mixture was added carbon disulfide (21 mL, 349.14 mmol) and the resultant dark mixture was stirred at room temperature for 2 h. To the mixture was added methyl iodide (12.4 mL, 160.64 mmol) at 0° C. and the mixture was stirred for 16 h. The mixture was poured into ice-water (300 mL) and extracted with EtOAc (3×50 mL). The EtOAc solution was dried and evaporated until crystals precipitated. The suspension was left in a refrigerator for 16 h. The crystals were filtered and washed with hexane to give the first crop (21.61 g) as a yellowish powder. The filtrate was concentrated, kept at 0° C. overnight and filtered to give the second crop (16.51 g). This was repeated two more times to give additional 1.44 g of the product (39.62 g, two steps from 81 94.7%). Mp 127–130° C. $^1$H NMR (CDCl$_3$) δ1.39 and 1.55 (2s, 6H, isopropylidene-CH$_3$), 2.60 (s, 3H, SCH$_3$), 3.40 (s, 3H, OCH$_3$), 4.01 (s, 2H, H$_5$), 4.30 (m, 1H, H$_4$), 4.50 (dd, 1H, H$_3$), 4.98 (d, 1H, H$_1$), 5.78 (dd, 1H, H$_2$), Example 65

Methyl 2-deoxy-β-L-erythro-pentopyranoside (84)

Compound 83 (40 g, 136 mmol) and AIBN (24.61 g, 150 mmol) were dissolved in dry dioxane (400 mL) by heating in an oil bath (100° C.). The mixture was bubbled with argon atmosphere at 100° C. for 15 min followed by addition of diphenylsilane (51.4 mL, 272 mmol). The temperature of the oil bath was raised to 130° C. and the mixture was refluxed for 16 h. Additional diphenylsilane (2 mL, 10.8 mmol) and AIBN (1.27 g, 7.7 mmol) were added and refluxing was continued for additional 5 h. Additional AIBN (0.2 g, 1.2 mmol) was added and refluxing was continued for additional 1 h. The mixture was cooled and evaporated to give compound 84 as a syrup, which was mixed with 80% HOAc (544 mL) and stirred at room temperature for 16 h. The mixture was evaporated to give a syrup which was partitioned between water and ether. The aqueous layer was washed with ether and the combined organic layer was extracted with water. The aqueous solution was evaporated to give compound 85 as a syrup (16.36 g, 81.4% for two steps from 83). $^1$H NMR (CDCl$_3$ δ), 1.89 (dd, 2H, H$_2$). 2.30. (d, 1H, OH), 2.47 (d, 1H, OH), 3.35 (s, 3H, OCH$_3$), 3.88–3.69 (m, 3H, H$_4$ & H$_5$) 4.03 (m, 1H, H$_3$), 4.79 (t, 1H, H$_1$).

Example 66

2'-deoxy-β-L-erythro-pentose (86)

Compound 85 (16.36 g, 110.5 mmol) was dissolved in 0.8 M HCl aqueous solution (546 mL) and the resultant mixture was stirred at room temperature for 72 h. The mixture was neutralized with 1N NaOH aqueous solution to PH 6–7 and was evaporated to give a syrup. The crude was purified on a silica gel column (4×15 cm) eluted with CH$_2$Cl$_2$/MeOH (1:0 to 95:5) The proper fractions were evaporated to give compound 86 as a syrup (10.53 g, 71.1%).

Example 67

Methyl 2'-deoxy-β-L-erythro-pentose (87)

Compound 86 (15.68 g, 117.0 mmol) was dissolved in dry MeOH (342 mL) and to the resultant solution was added 1% HCl/MeOH (35 mL). The solution was kept at ROOM TEMPERATURE for 1 h and neutralized with Py (55 mL) at 5° C. to PH ~6. The mixture was evaporated with silica gel and purified on a silica gel column (1×5 cm) eluted with CH$_2$Cl$_2$/MeOH(98:2 to 96:4) to give compound 87 as a syrup (13.94 g, 80.5%). $^1$H NMR (CDCl$_3$) δ2.22–2.44 (m, 2H, H$_2$), 3.50 and 3.59 (2s, 3H, OCH$_3$), 3.75–3.88 (m, 2H, H$_5$), 4,26 (m, 1H, H$_4$), 4.66 (m, 1H, H$_3$), 5.25 (t, 1H, H$_1$).

Example 68

Methyl 2'-deoxy-3,5-di-
O-p-toluoyl-L-erythro-pentose (88)

Compound 87 (9.00 g, 60.8 mmol) was dissolved in pyridine (180 mL) and cooled in an ice-water bath. To this cold solution was added toluoyl chloride (18 mL, 00 mmol) in 30 min and the resultant solution was stirred at room temperature for 16 h. The mixture was evaporated to dryness. The mixture was extracted with EtOAc, washed with brine, dried and evaporated. The crude product was purified on a silica gel column (3×15 cm) using hexane/EtOAc (1:0 to 5:1) as the eluent. Evaporation of the proper fractions gave compound 88 as a syrup (22.63 g, 97%). $^1$H NMR (CDCl$_3$) δ2.40 (2s, 6H, 2×CH$_3$), 3.35 (s, 3H, OCH$_3$ of β-anomer), 3.41 (s, 3H, OCH$_3$ of α-anomer), 4.6–4.5 (m, H$_4$ and H$_5$ of both anomers), 5.19 (d, 1H, H$_1$ of α-anomer), 5.21 (dd, 1H, H$_1$ of β-anomer), 5.41 (m, 1H, H$_3$ of α-anomer), 5.59 (m, 1H, H$_3$ of β-anomer), 7.18–8.02 (m, 8H, Aromatic), Example 68

2'-Deoxy-3',5'-di-
O-p-toluoyl-α-L-erythro-pentofuranosyl chloride (13)

Compound 88 (22 g, 57.3 mmol) was dissolved in dry ether (200 mL) and the solution was cooled to 0° C. in an ice bath. To the solution was bubbled dry HCl for ~5 min until the mixture crystallized. The reaction mixture was then kept in a refrigerator overnight. The solid that precipitated was filtered and washed with cold ether. The solid was immediately dried under vacuum over NaOH to give compound 13 as a colorless crystalline powder (19.28 g). The filtrate was concentrated and treated with HCl and kept in a refrigerator overnight. Filtration, washing and drying gave additional 1.2 g of product (total 20.48 g, 92%), mp 118–121° C. $^1$H NMR (CDCl$_3$) δ2.39 (2s, 6H, aromatic-CH$_3$), 2.82 (m, 2H, H$_2$), 4.65 (m, 2H, H$_5$), 4.86 (q, 1H, H$_4$), 5.57 (m, 1H, H$_3$), 6.48 (d, 1H, H$_1$), 7.25 (2d, 4H, aromatic-H), 7.95 (2d, 4H, aromatic-H).

Example 69

Methyl 1-(2'-deoxy-3', 5 '-di-
O-p-toluoyl-β-L-erythro-pentofuranosyl)-
1,2,4-triazole-5-carboxylate (89), Methyl 1-(2'-deoxy-3',5'-di-
O-p-toluoyl-β-L-erythro-pentofuranosyl)-
1,2,4-triazole-2-carboxylate (90) and Methyl 1-(2'-deoxy-3',5'-di-
O-p-toluoyl-β-L-erythro-pentofuranosyl)-
1,2,4-triazole-3-carboxylate (91)

To a solution of methyl 1,2,4-triazole-3-carboxylate (1.27g, 10 mmol) in dry acetonitrile (50 mL) was added sodium hydride (60% in oil, 0.5 g, 12.5 mmol). The mixture was stirred at room temperature for 30 min. Dry and powdered chloro sugar 13 was added and the suspension was stirred at room temperature for 16 h. The mixture was evaporated to give a residue which was partitioned between water/EtOAc and extracted in EtOA. The aqueous solution was extracted with EtOAc. The combined EtOAc solution was washed with brine and evaporated to dryness. The mixture was purified on a silica gel column (3×20 cm) using EtOAc/hexane (1.2:1) as the eluent to give 89 (1.72 g), 90 (0.98 g) and 91 (0.45 g).

$^1$H NMR (CDCl$_3$) 89: δ2.52 (2s, 6H, CH$_3$), 2.82 (m, 1H, H$_{2'}$), 3.45 (m, 1H, H$_{2'}$), 4.60 (dd, 1H, H$_{5'}$), 4.72 (dd, 1H, H$_{5'}$), 4.76 (m, 1H, H$_{4'}$), 6.03 (m, 1H, H$_{3'}$), 7.29–7.38 (m, 5H, aromatic-H and H$_{1'}$), 7.97–8.12 (m, 5H, aromatic-H and C$_5$H). 90: δ2.50 & 2.53 (2s, 6H, CH$_3$), 2.95 (m, 1H, H$_{2'}$), 3.20 (m, 1H, H$_{2'}$), 4.09 (s, 3H, OCH$_3$), 4.72 (m, 3H, H$_{4'}$ & H$_{5'}$), 5.83 (m, 1H, H$_{3'}$), 6.47 (t, 1H, H$_{1'}$), 7.36 (dd, 4H, aromatic-H), 8.02 (dd, 4H, aromatic-H), 8.51 (s, 1H, C$_5$H). 91: δ2.53 (m, 7H, H$_{2'}$ & 2×CH$_3$), 3.16 (m, 1H, H$_{2'}$), 4.13 (s, 3H, OCH$_3$,), 4.69–4.85 (m, 3H, H$_{4'}$ & H$_{5'}$), 5.73 (m, 1H, H$_{3'}$), 6.88 (q, 1H, H$_{1'}$), 7.35 (dd, 4H, aromatic-H), 7.94 & 8.05 (dd, 4H, aromatic-H), 8.76(s, 1H, C$_5$H).

Example 70

1-(2'-Deoxy-β-L-erythro-pentofuranosyl)-1,2,4-triazole-5,-carboxamide (92)

A mixture of 89 (1.77 g, 3.70 mmol) and saturated methanolic ammonia solution (40 mL) was heated in a steel bomb at 55° C. for 16 h. After cooling, the solution was evaporated with silica gel and purified on a silica gel column eluted with CH$_2$Cl$_2$/MeOH (10:1) to give compound 92 as a colorless powder (297 mg, 35%). $^1$H NMR (DMSO-d$_6$): δ2.27 (m, 1H, H$_{2'}$), 2.60 (m, 1H, H$_{2'}$), 3.32 (m, 1H, H$_{5'}$), 3.48 (m, 1H, H$_{5'}$), 3.80 (m, 1H, H$_{4'}$), 4.41 (m, 1H, H$_{3'}$), 7.12 (t, 1H, H$_{1'}$), 8.06 (s, 1H, NH), 8.14 (s, 1H, C$_5$H), 8.27 (s, 1H, NH).

Example 71

1-(2'-Deoxy-β-L-erythro-pentofuranosyl)-1,2,4-triazole-3-carboxamide (93)

A mixture of 91 (0.45 g, 0.94 mmol) and saturated methanolic ammonia solution (20 mL) was heated in a steel bomb at 55° C. for 16 h. After cooling, the solution was evaporated to dryness. The residue was purified on a silica gel column using CH$_2$Cl$_2$/MeOH (10:1) as the eluent to give 93 (54 mg, 25%). $^1$H NMR (DMSO-d$_6$): δ2.24 (m, 1H, H$_{2'}$), 2.38 (m, 1H, H$_{2'}$), 3.61 (m, 2H, H$_{5'}$), 3.85 (m, 1H, H$_{4'}$), 4.30 (m, 1H, H$_{3'}$), 6.70 (t, 1H, H$_{1'}$), 7.94 (s, 1H, NH), 8.33 (s, 1H, NH) 8.98 (s, 1H, C$_5$H).

Example 72

1-(2'-Deoxy-3',5'-di-O-p-toluoyl-β-L-erythro-pentofuranosyl)-2,4-dicyanopyrrole (94)

To a solution of 2,4-dicyanopyrrole (302 mg, 2.58 mmol) in dry acetonitrile (25 mL) was added sodium hydride (60% in oil, 125 mg, 2.6 mmol). The mixture was stirred at room temperature for 30 min. The chloro 13 (1 g, 2.58 mmol) was added and the suspension was stirred at room temperature for 16 h. The mixture was evaporated to give a solid residue which was partitioned between water and EtOAc. The aqueous solution was extracted with EtOAc. The combined EtOAc extract was washed with water and brine, dried and evaporated to dryness. The product was purified on silica gel column (3×20 cm) using hexane/EtOAc (5:2) as eluent to give 94 as an oil (605 mg, 50%). $^1$H NMR (CDCl$_3$): δ2.29 (s, 3H, aromatic-CH$_3$), 2.55 (s, 3H, aromatic-CH$_3$), 2.67 (m, 1H, H$_{2'}$), 2.98 (m, 1H, H$_{2'}$), 4.74–4.89 (m, 3H, H$_{4'}$ & H$_{5'}$), 5.77(m, 1H, H$_{3'}$), 6.36 (t, 1H, H$_{1'}$), 7.18 (s, 1H, C$_5$H), 7.38 (m, 4H, aromatic-H), 7.68 (s, 1H, C$_3$H), 7.97 (d, 2H, aromatic-H), 8.05 (d, 2H, aromatic-H).

Example 73

1-(2'-Deoxy-β-L-erythro-pentofuranosyl)-2,4-dicyanopyrrole (95)

A mixture of 94 (605 mg, 1.29 mmol) and saturated methanolic ammonia solution (20 mL) was heated in a steel bomb at 65° C. for 16 h. After cooling, the solution was evaporated to dryness. The crude product was purified on a silica gel column eluted with CH$_2$Cl$_2$/MeOH (10:1) to give 95 (158 mg, 52%). $^1$H NMR (CD$_3$OD): δ2.55 (m, 2H, H$_{2'}$), 3.82 (m, 2H, H$_{5'}$), 4.08 (m, 1H, H$_{4'}$), 4.53 (m, 1H, H$_{3'}$), 6.38 (t, 1H, H$_{1'}$), 7.37 (s, 1H, C$_5$H), 8.19 (s, 1H, C$_3$H).

Example 74

1-(2'-Deoxy-β-L-erythro-pentofuranosyl)pyrrole-2,4-dicarboxamide (96)

To a solution of 95 (90 mg, 0.385 mmol) in aqueous NH$_4$OH solution (29.6%, 9 mL) was added H$_2$O$_2$. The solution was stirred at room temperature for 2 h and evaporated to dryness. The residue was purified on a silica gel column eluted with CH$_2$Cl$_2$/MeOH (10:1) to give Compound 96 (75 mg, 72%). $^1$H NMR (CD$_3$OD): δ2.31 & 2.61 (m, 2H, H$_{2'}$), 3.89 (m, 2H, H$_{5'}$), 4.04 (m, 1H, H$_{4'}$), 4.45 (m, 1H, H$_{3'}$), 6.93 (t, 1H, H$_{1'}$), 7.24 (s, 1H, C$_5$H), 8.09 (s, 1H, C$_3$H).

Example 75

Methyl 1-(2'-deoxy-3,',5'-di-O-p-toluoyl-β-L-erythro-pentofuranosyl)pyrazole-3,5-dicarboxylate (97)

To a solution of methyl pyrazole-3,5-dicarboxylate (458 mg, 2.5 mmol) in dry acetonitrile (25 mL) was added sodium hydride (60% in oil, 144 mg, 3.0 mmol). The mixture was stirred at room temperature for 30 min. The chloro sugar 13 (970 mg, ~95%, 2.5 mmol) was added and the suspension was stirred at room temperature for 4 h. The mixture was evaporated to dryness and the residue was purified on silica gel column (3×7 cm) using hexane/EtOAc (5:2) as the eluent to give 97 as an oil (470 mg, 35%). $^1$H NMR (CDCl$_3$): δ2.40 (d, 6H, aromatic-CH$_3$), 2.70 (m, 1H, H$_{2'}$), 3.60 (m, 1H, H$_{2'}$), 3.93 (d, 6H, OCH$_3$), 4.48–4.65 (m, 3H, H$_{4'}$ & H$_{5'}$), 5.89(m, 1H, H$_{3'}$), 7.18–7.29 (m, 5H, aromatic-H & H$_{1'}$), 7.38 (s, 1H, C$_4$H),7.90 (m, 4H, aromatic-H).

Example 76

1-(2'-Deoxy-β-L-erythro-pentofuranosyl)pyrazole-3,5-dicarboxamide (98)

A mixture of 97 (270 mg, 0.51 mmol) and saturated methanolic ammonia solution (20 mL) was heated in a steel bomb at 100° C. for 16 h. After cooling, the solution was evaporated and purified on a silica gel column using CH$_2$Cl$_2$/MeOH (10:1) to give 98 as a colorless powder (189 mg, 73%). $^1$H NMR (DMSO-d$_6$): δ2.25 (m, 1H, H$_{2'}$), 2.89 (m, 1H, H$_{2'}$), 3.42 (m, 1H, H$_{5'}$), 3.59 (m, 1H, H$_{5'}$), 3.86 (q, 1H, H$_{4'}$), 4.55 (m, 1H, H$_{3'}$), 4.77 (t, 1H, OH), 5.27 (d, 1H, OH), 7.17 (t, 1H, H$_{1'}$), 7.29 (s, 1H, C$_4$H), 7.51 (s, 1H, NH), 7.66 (s, 1H, NH), 7.80 (s, 1H, NH), 8.19 (s, 1H, NH).

Example 77

Methyl 1-(2'-deoxy-3',5'-di-O-p-toluoyl-β-L-erythro-pentofuranosyl)pyrazole-4-carboxylate (99)

To a solution of methyl pyrazole-4-carboxylate (315 mg, 2.5 mmol) in dry acetonitrile (30 mL) was added sodium hydride (60% in oil, 144 mg, 3.0 mmol). The mixture was stirred at 50° C. for 15 min. The chloro sugar 13 (1 g, ~95%, 2.5 mmol) was added and the suspension was stirred at room temperature for 2 h. The mixture was evaporated to give a residue which was partitioned between water and EtOAc. The aqueous solution was extracted with EtOAc. The combined EtOAc extract was washed with water and brine, dried over NaSO$_4$ and evaporated to dryness. The residue was purified on silica gel column (3×12 cm) using hexane/EtOAc (4:1) to give 99 as a crystalline powder (549 mg, 46%). $^1$H NMR (CDCl$_3$): δ2.40 (d, 6H, aromatic-CH$_3$), 2.72 (m, 1H, H$_{2'}$), 3.16 (m, 1H, H$_{2'}$), 3.79 (d, 3H, OCH$_3$), 4.51–4.62 (m, 3H, H$_{4'}$ & H$_{5'}$), 5.77 (m, 1H, H$_{3'}$), 6.20 (t, 1H, H$_{1'}$), 7.24 (m, 4H, aromatic-H), 7.92 (m, 5H, aromatic-H & C$_5$h), 8.10 (s, 1H, C$_3$H).

Example 78

1-(2'-Deoxy-β-L-erythro-pentofuranosyl)pyrazole-4-carboxamide (100)

A mixture of 99 (500 mg, 1.046 mmol) and saturated methanolic ammonia solution (30 mL) was heated in a steel bomb at 100° C. for 16 h. After cooling, the solution was evaporated and the residue was purified on a silica gel column using CH$_2$Cl$_2$/MeOH (10:1) to give 100 as yellow foam (50 mg, 20%). $^1$H NMR (DMSO-d$_6$): δ2.30 (m, 1H, H$_{2'}$), 2.56 (m, 1H, H$_{2'}$), 3.41–3.56 (m, 2H, H$_{5'}$), 3.84 (m, 1H, H$_{4'}$), 4.36 (m, 1H, H$_{3'}$), 4.88 (bs, 1H, OH), 5.32 (bs, 1H, OH), 6.11 (t, 1H, H$_{1'}$), ), 7.08 (s, 1H, NH), 7.63 (s, 1H, NH), ), 7.90 (d, 1H, C$_5$H), 8.36 (d, 1H, C$_3$h). 7.80 (s, 1H, NH), 8.19 (s, 1H, NH).

Example 79

Methyl-α-L-lyxopyranoside (102)

To a methanolic HCl solution [600 mL, 0.5% w/v, prepared in situ by reaction of acetyl chloride (6.0 mL)] was added L-lyxose (101, 118 g, 786 mmol and refluxed for 5 h [the reaction was complete in 4 h (by TLC 30% MeOH/CH$_2$Cl$_2$) and continued for additional 1 h (total 5 h)] under exclusion of moisture (protected by CaCl$_2$ guard tube). The reaction mixture was neutralized with pre-treated[1] amberlite basic resin IRA 410 (100.0 g) for 10 min under stirring. The resin was filtered and washed with methanol (3×50 mL). The combined washings were evaporated to obtain a color less syrup. The syrup was co-evaporated with ethyl acetate (2×50 mL) and finally recrystallized (by scratching the side of RB flask or sonication) from ethyl acetate (500 mL) to obtain white crystalline product 102 (87 g, 67% total from both 1 and 2 crop). $^1$H NMR (300 MHz, (CD$_3$)$_2$CO): δ3.15 (bs, 3H, OH), 3.41 (s, 3H, OCH$_3$), 3.48 (m, 1H), 3.66–3.72 (m, 2H), 3.73–3.87 (m, 2H), 4.64 (d, 1H, H-$_{5'}$, J=2.7 Hz).

Example 80

Methyl-2,3-O-isopropylidene-α-L-lyxopyranoside (103)

To a suspension of 102 (69 g, 420.0 mmol) in a mixture of 2,2-dimethoxy propane (200.0 mL) and anhydrous acetone (200.0 mL) was added a solution (4M) of HCl in dioxane (4.0 mL) and the reaction mixture was stirred at 25° C. for 16 h. TLC (50% ethyl acetate/CH$_2$Cl$_2$) of the reaction indicated the complete conversion of the starting material. The reaction was quenched with solid sodium bicarbonate (500 mg) and filtered. The filtrate was evaporated and the oily residue (pinkish) that obtained was purified by silica gel flash chromatography using CH$_2$Cl$_2$/ethyl acetate (100/0 to 80/20, in 5% increments) as the eluent to obtain the product 103 (80 g, 93.2%).). $^1$H NMR (300 MHz, (CDCl$_3$): δ1.31 (s, 3H), 1.47 (s, 3H), 2.95 (bs, 1H), 3,41 (s, 3H), 3.66–3.77 (m, 3H), 4.07 (dd, 1H, J=6.04 & 2.75 Hz), 4.16 (t, 1H, J=6.04 & 4.67 Hz), 4.60 (d, 1H, J=2.74 Hz).

Example 81

Methyl-4-azido-4-deoxy-2,3-O-isopropylidene-β-D-ribopyranoside (104)

To a mixture of pyridine (6.4 mL, 79.65 mmol) and dimethylamino pyridine (100 mg, 0.72 mmol) in anhydrous CH$_2$Cl$_2$ (400 mL) was slowly added trifluoromethanesulfonic anhydride (11.82 mL, 71.68 mmol) at −20° C. The mixture was stirred at −20° C. for 5 min and was then added a solution of 103 (5.0 g, 24.50 mmol) in CH$_2$Cl$_2$ (50.0 mL) The reaction mixture was stirred at −20° C. for 15 min. It was then poured into a mixture of ice-water (500 mL) and the organic layer separated. The aqueous phase was extracted with CH$_2$Cl$_2$ (2×100 mL). The combined organic layer was washed with brine (500 mL), dried (NaSO$_4$) and evaporated to obtain the product as pale yellow gummy solid (14 g).

To a solution of above methyl-4O-trifluoromethenesulfonyl-2,3-O-isopropylidine-β-L-lyxopyranoside in a mixture of DMF (350 mL) and tetramethyl urea (50 mL) was added sodium azide (30.0 g, 461.53 mmol, 18.83 eq) at 0–5° C. (ice-water bath) and stirred at 23° C. for 3 h. The volatiles were evaporated and the residue was diluted with CH$_2$Cl$_2$ (500 mL) and water (200 mL). The organic layer was separated and washed with water (2×250 mL) and brine (300 mL), dried (NaSO$_4$) and evaporated to obtain an oily residue which was purified by flash silica gel chromatography using hexane/ethyl acetate (100/0; 97.5/2.5; and 95/5) as the eluent to obtain the product 104 (2.8 g, 49.88% for the two steps). $^1$H NMR (300 MHz, (CDCl$_3$): δ1.36 (s, 3H, CH$_3$), 1.54 (s, 3H, CH$_3$), 3.42 (s, 3H, OCH$_3$), 3.7–3.9 (m, 3H), 4.01 (dd, 1H, J=6.05 & 3.85 Hz), 4.48 (d, 1H, J=3.85 Hz), 4.51 (m, 1H).

Example 82

N-Acetyl-4-amino-4-deoxy-2,3-O-isopropylidene-β-D-methyl-ribopyranoside (105)

To a solution of 104 (6.5 g, 28.38 mmol) in MeOH (50.0 mL) was added NaHCO$_3$ (2.38 g, 28.38 mmol) followed by Pd/C (5% w/w, 650 mg). The reaction mixture was shaken well under H$_2$ (40 psi) atmosphere at room temperature for 1 h. The TLC (30% ethyl acetate/hexane) indicated completion of the reaction. The reaction mixture was filtered over celite bed and the filtrate was evaporated to dryness. The residue was co-evaporated with toluene (2×20 mL) and pyridine (2×20 mL). The resulting residue was then carried forward to the next reaction without further purification.

To a mixture of the above residue (5.76 g, crude from the above reaction) and DMAP (0.059 g, 0.425 mmol) in pyridine (6.8 mL, 84.5 mmol) was added acetic anhydride (4.01 mL, 42.57 mmol) at 0° C. The reaction mixture was stirred at room temperature for 2 h. The TLC (100% ethyl acetate) indicated completion of the reaction. MeOH (1.0 mL) was added and the volatiles were evaporated. The residue was dissolved in CH$_2$Cl$_2$ (300 mL) and this solution was then washed with cold and dil. HCl (0.5M, 3×200 mL), sat. NaHCO$_3$ (200 mL) and brine (200 mL), dried (Na$_2$SO$_4$) and evaporated. The residue that obtained was purified by flash chromatography over silica gel using ethyl acetate/hexane (0/100 to 10/90 to 20/80 to 50/50 to 100/0) as the eluent to obtain the product 105 (in a combined yield of 3.76 g, 54.11%). $^1$H NMR (300 MHz, (CDCl$_3$): δ1.35 (s, 3H, CH$_3$), 1.51 (s, 3H, CH$_3$), 2.0 (s, 3H, COCH$_3$), 3.37 (t, 1H), 3.45 (s, 3H, OCH$_3$), 3.85 (dd, 1H), 4.05 (dd, 1H), 4.38 (dd, 1H), 4.40 (d, 1H, J=4.5 Hz), 4.58 (m, 1H), 5.78 (bd, 1H).

Example 83

1,2,3,5-Tetra-O-acetyl-4-deoxy-4-(acetamido)-D-ribofuranose (106)

A solution of 105 (5.0 g, 20.40 mmol) in a mixture of distilled water and AcOH (1:1, 50 mL) was heated at 70–75° C. for 1.5 h. The TLC (100% ethyl acetate) indicated completion of the reaction. Absolute EtOH (2×30 mL) was added and co-evaporated the volatiles to obtain a dry solid residue. To this solid was added a mixture of glacial acetic acid and acetic anhydride (50 mL, 1:1) and cooled to 0° C., and treated with conc. $H_2SO_4$ (1.5 mL). The reaction mixture was stirred at 0° C. for 30 min and then kept at 4° C. for 2 days. The reaction mixture was treated with anhy. NaOAc (15.0 g) and stirred at roo temperature for 30 min. The reaction mixture was then poured into ice-water mixture (300 mL) and extracted with $CH_2Cl_2$ ((2×250 mL). The combined organic layer was wished with water (2×250 mL) and brine (400 mL), dried ($Na_2SO_4$) and evaporated. The crude residue that obtained was purified by flash chromatography over silica gel using MeOH/$CH_2Cl_2$ (0/100 to 3/97) as the eluent to give pure product 106 (3.71 g, 50.82%). $^1$H NMR (300 MHz, (CDCl$_3$): δ1.99–2.11 (m, 15H, 5×CH$_3$), 4.17–4.5 (m, 3H), 5.27–5.52 (m, 2H), 6.35 (s, 0.75H), 6.53 (d, 0.25H, J=4.8 Hz).

Example 84

Methyl-1-(2',3',5'-tri-O-acetyl-4'-deoxy-4'-acetamido-β-D-ribofuranosyl)-1,2,4-triazole-3-carboxylate (107)

A suspension of methyl-1,2,4-triazole-3-carboxylate (1.77 g, 13.97 mmol) and ammonium sulphate (177 mg) in hexamethyldisilazane (40 mL) was refluxed for 2.5 h under $N_2$ atmosphere. The reaction mixture was evaporated to dryness and the residue was suspended in 1,2-dichloroethane (50 mL). It was then treated with a solution of 106 (4.4 g, 12.25 mmol) in 1,2-dichloroethane (50 mL). To the reaction mixture was then added fuming SnCl$_4$ (1.63 mL, 13.97 mmol) at 0–5° C. (ice-water bath) and stirred at room temperature for 1 h. The reaction mixture was carefully quenched with saturated solution of NaHCO$_3$ (50 mL) and then diluted with $CH_2Cl_2$ (200 mL). The mixture was filtered over a celite bed (5 g) and washed with $CH_2Cl_2$ (100 mL). The organic layer of the filtrate was separated and the aqueous layer was extracted with $CH_2Cl_2$ (2×100 mL). The combined organic layer was washed with water (2×300 mL) and brine (500 mL), dried ($Na_2SO_4$) and evaporated. The crude residue that obtained was recrystallized from ethyl acetate (40 mL) to obtain pure titled product 107 (2.7 g, 51.71%). $^1$H NMR (300 MHz, (CDCl$_3$): δ2.03–2.15 (m, 12H, 4×COCH$_3$), 3.95 (s, 3H, OCH$_3$), 4.2 (m, 1H, H$_{5'}$), 4.43 (m, 2H, H$_{4'}$ & H$_{5'}$), 5.65 (dd, 1H, H$_{3'}$, J=4.67 & 1.1 Hz), 6.17 (t, 1H, H$_{2'}$, J=4.67 & 6.04 Hz), 6.28 (d, 1H, H$_{1'}$, J=6.04 Hz), 8.47 (s, 0.86H, major rotamer, C$_5$H), 8.60 (s, 0.14H, minor rotamer, C$_5$H). Anal. Calcd. for $C_{17}H_{22}N_4O_9$: C, 47.89; H, 5.20; N. 13.14. Found: C, 47.93; H, 5.40; N, 13.27.

Example 85

1-(4'-Deoxy-4'-acetamido-β-D-ribofuranosyl)-1,2,4-triazole-3-carboxamide (108)

A solution of 107 (2.7 g, 6.33 mmol) in saturated methanolic ammonia (100 mL) was stirred at room temperature in steel bomb for 16 h. The reaction mixture was evaporated to dryness and the residue that obtained was purified by flash chromatography over alumina using the solvent mixture ethyl acetate/n-propyl alcohol/water (64/4/32 to 57/14/29%, lower layer) as the eluent to afford the titled product 108 (1.7 g). The product was wet −5% with ethyl alcohol and also contaminated little acetamide. $^1$H NMR (300 MHz, CD$_3$OD): δ1.87 (s, 0.86H, COCH$_3$, minor rotamer (min)), 2.14 (s, 2.14H, COCH$_3$, major rotamer (maj)), 3.87 (d, 2H, H$_{5'}$, J=6.59 Hz), 4.1–4.01 (m, 1H, H$_{4'}$), 4.26 (d, 0.75H, J=4.12 Hz, H$_{3'}$, maj), 4.31 (t, 0.25H, J=3.8 Hz, H$_{3'}$, min), 4.54 (t, 0.25H, J=4.1 Hz, H$_{2'}$, min), 4.85 (dd, 0.75H, J=4.4 & 6.05 Hz, H$_{2'}$, maj), 6.03 (d, 0.75H, J=6.04 Hz, H$_{1'}$, maj), 6.81 (d, 0.25H, J=4.13 Hz, H$_{1'}$, min), 8.69 (s, 0.75H, C$_5$H, maj), 8.95 (s, 0.25H, C$_5$H, min), Anal. Calcd. for $C_{10}H_{15}N_5O_5$: C, 42.10; H, 5.30; N, 24.55. Found: C, 42.21; H, 5.19; N, 24.23.

Example 86

1-[(3',5'-O-(1,1,3,3-Tetraisopropyl-1,3-disiloxanediyl)-4'-deoxy-4'-acetamido-β-D-ribofuranosyl]-1,2,4-triazole-3-carboxamide (109)

A solution of 108 (0.7 g, 2.45 mmol) in pyridine (15 mL) was treated with 1,3-dichloro-1,1,3,3-tetraisopropyl-disiloxane (1.06 mL, 3.31 mmol) and stirred at room temperature for 16 h. The reaction mixture was carefully quenched with saturated solution of NaHCO$_3$ (5 mL) and diluted with $CH_2Cl_2$ (100 mL). The organic layer was separated and the aqueous layer was extracted with $CH_2Cl_2$ (2×25 mL). The combined organic layer was washed with water (2×100 mL) and brine (100 mL), dried ($Na_2SO_4$) and evaporated. The crude residue was purified by flash chromatography over silica gel using CHCl$_3$/MeOH (100/0-98/2-95/5-90/10) as the eluent to afford 109 (0.7 g, 54%). $^1$H NMR (300 MHz, CDCl$_3$): δ0.93–1.18 (m, 24H), 1.38 (m, 2H), 2.02 (s, 0.84H, COCH$_3$, minor rotamer (min)), 2.15 (s, 2.16H, COCH$_3$, major rotamer (maj)), 3.83 (m, 1H, H$_{5'}$), 3.98–4.13 (m, 1H, H$_{5'}$), 4.33 (d, 0.34H, J=3.85 Hz, H$_{2'}$, min), 4.42 (d, 0.66H, J=4.67 Hz, H$_{2'}$, maj), 4.52 (dd, 0.34H, H$_{4'}$, min), 4.65 (dd, 0.66H, H$_{4'}$, maj), 5.29 (t, 1H, J=4.97 Hz, H$_{3'}$), 5.80 (bs, 0.66H, maj), 5.94 (bs, 0.34H, min), 5.99 (s, 0.34H, H$_{1'}$, min), 6.40 (s, 0.66H, H$_{1'}$, maj), 6.91 (bs, 0.66H, maj), 7.01 (bs, 0.34H, min), 8.37 (s, 0.66H, C$_5$H, maj), 8.53 (s, 0.34H, C$_5$H, min).

Example 87

1-[2'-O-(p-Tolylthionoformyl)-3',5'-O-(1,1,3,3-tetraisopropyl-1,3-disiloxanediyl)-4'-deoxy-4'-acetamido-β-D-ribofuranosyl]-1,2,4-triazole-3-carboxamide (110)

To a solution of 109 (0.6 g, 1.138 mmol) in a mixture of $CH_2Cl_2$ (9 mL) and pyridine (1 mL) was added O-(p-tolyl) thionochloroformate (0.219 mL, 1.42 mmol) and the reaction mixture was stirred at room temperature for 16 h. The reaction mixture was quenched with saturated solution of NaHCO$_3$ (5 mL) and diluted with $CH_2Cl_2$ (100 mL). The organic layer was separated and the aqueous layer was extracted with $CH_2Cl_2$ (2×25 mL). The combined organic layer was washed with water (2×100 mL) and brine (100 mL), dried ($Na_2SO_4$) and evaporated. The crude residue was purified by flash chromatography over silica gel using CHCl$_3$/ethyl acetate (100/0–95/5–90/10) as the eluent to afford pure product 110 (0.35 g, 45%). $^1$H NMR (300 MHz, CDCl$_3$): δ1.04–1.15 (m, 24H), 1.32 (m, 2H), 2.01 (s, 1H, COCH$_3$, minor rotamer (min)), 2.19 (s, 2H, COCH$_3$, major rotamer (maj)), 2.35 (s, 3H, CH$_3$), 3.92 (m, 1H, H$_{5'}$), 4.05 (m, 1H, H$_{5'}$), 4.68–4.81 (m, 1H, H$_{4'}$), 5.5 (t, 1H, J=6.05 & 5.22 Hz, H$_{3'}$), 5.75 (bs, 0.66H, maj), 5.88 (bs, 0.34H, min), 6.10 (d, 1H, J=4.67 Hz, H$_{2'}$), 6.17 (s, 0.34H, H$_{1'}$, min), 6.54 (s, 0.66H, H$_{1'}$, maj), 6.87 (bs, 0.66H, maj), 6.96 (d, 2H, J=8.24 Hz, aromatic-H), 6.98 (bs, 0.34H, min), (7.20 (d, 2H, J=8.24 Hz), 8.40 (s, 0.66H, C$_5$H, maj), 8.68 (s, 0.34H, C$_5$H, min).

Example 88

1-[(3',5'-O-(1,1,3,3-Tetraisopropyl-1,3-disiloxanediyl)-2',4'-dideoxy-4'-acetamido-β-D-ribofuranosyl]-1,2,4-triazole-3-carboxamide (111)

A solution of 110 (0.35 g, 0.516 mmol) in toluene (20 mL) was purged with argon for 20 min and then treated with 2,2'-azobisisobutyronitrile (0.084 g, 0.516 mmol) and tributyltin hydride (0.274 mL, 1.03 mmol). The reaction mixture was refluxed for 3 h under a stream of argon. The reaction mixture was evaporated to dryness and the crude residue was purified by flash chromatography over silica gel using CHCl$_3$/ethyl acetate (100/0-90/10-70/30-40/60-20/80-0/100) as the eluent to afford the product 111 (0.23 g, 87%). $^1$H NMR (300 MHz, CDCl$_3$): δ0.95–1.15 (m, 24H), 1.24 (m, 2H), 2.0 (s, 0.9H, COCH$_3$, minor rotamer (min)), 2.13 (s, 2.1H, COCH$_3$, major rotamer (maj)), 2.36–2.58 (m, 1H, H$_{2'}$), 2.84 (m, 1H, H$_{2'}$), 3.74–3.92 (m, 2H, H$_{5'}$), 4.11 (m, 0.66H, H$_{4'}$, maj), 4.49–4.67 (m, 0.34H, H$_{4'}$, min), 5.3 (m, 1H, H$_{3'}$), 5.88 (bs, 0.66H, maj), 6.01 (bs, 0.34H, min), 6.14 (d, 0.34H, J=6.02 Hz, H$_{1'}$, min), 6.54 (d, 0.66H, J=7.97 Hz, H$_{1'}$, maj), 6.89 (bs, 0.66H, maj), 7.03 (bs, 0.34H, min), 8.35 (s, 0.66H, C$_5$H, maj), 8.55 (s, 0.34H, C$_5$H, min).

Example 89

1-(2',4'-Dideoxy-4'-acetamido-β-D-ribofuranosyl)-1,2,4-triazole-3-carboxamide (112)

A solution of 111 (0.23 g, 0.45 mmol) in CH$_2$Cl$_2$ (5 mL) was treated with triethylamine trishydrofluride (0.29 mL, 1.79 mmol) at room temperature. The reaction mixture was stirred for 48 h at room temperature. The volatiles were removed and the residue was purified by flash chromatography over silica gel using CHCl$_3$/MeOH (100/0-95/5-90/10) as the eluent to afford pure product 112 (0.08 g, 66%). $^1$H NMR (300 MHz, CD$_3$OD): 67 1.95 (s, 0.36H, COCH$_3$, minor rotamer (min)), 2.16 (s, 2.64H, CH$_3$, major rotamer (maj)), 2.51 (m, 1H, H$_{2'}$), 2.87 (m, 1H, H$_{2'}$), 3.82 (m, 2H, H$_{5'}$), 3.99 (t, 1H, J=6.87 Hz, H$_{4'}$), 4.44 (d, 1H, J=4.12 Hz, H$_{3'}$), 6.54 (t, 1H, J=7.69 Hz, H$_{1'}$), 8.63 (s, 0.88H, C$_5$H, maj), 8.88 (s, 0.12H, C$_5$H, min). Anal. Calcd. for C$_{10}$H$_{15}$N$_5$O$_4$: C, 44.60; H, 5.62; N, 26.01. Found: C, 44.71; H, 5.69; N, 25.98.

Example 90

Methyl-2,3-O-isopropylidene-α-D-lyxopyranoside (115)

To a methanolic HCl solution [500 mL, 0.5% w/v, prepared in situ by reaction of acetyl chloride (5 mL, 70.37 mmol) with MeOH(Fisher HPLC grade)] was added D-lyxose (113, 100 g, 666.66 mmol) and refluxed for 5 h under N$_2$ atmosphere. The reaction mixture was neutralized with pre-treated[1] amberlite basic resin IRA-410 (100.0 g) for 10 min under stirring. The resin was filtered and washed with methanol (3×125 mL). The combined washings were evaporated to obtain a color less syrup of methyl-β-D-lyxopyranoside (114, 110 g, a quantitative yield) which was carried forward for the next reaction without further purification Note Preparation of pre-treated Amberlite Resin IRA-410: The resin (100 g) was treated with aq. NaOH (0.5M, 200 mL) for 15 min. Under stirring and filtered and washed with deionized water (4×300 mL) until the pH of washings showed neutral to pH paper. Finally the resin was washed with anhydrous MeOH (3×30 mL) and used immediately.

To a suspension of 114 (110 g, 666.66 mmol) in a mixture of 2,2-dimethoxy propane (400.0 mL) and anhydrous acetone (400.0 mL) was added a solution (4M) of HCl in dioxane (8.0 mL) and the reaction mixture was stirred at 25° C. for 16 h. The TLC (50% ethyl acetate/CH$_2$Cl$_2$) indicated completion of the reaction. The reaction was quenched with solid sodium bicarbonate (500 mg) and filtered. The filtrate was evaporated and the oily residue (pinkish) was purified by silica gel flash chromatography using CH$_2$Cl$_2$/ethyl acetate (100/0 to 80/20, with 5% increments) as the eluent to obtain 115 (63.97%, 87 g, overall yield for both the steps).

Example 91

Methyl-4-azido-4-deoxy-2,3-O-isopropylidene-β-L-ribopyranoside(116)

To a mixture of pyridine (6.432 mL, 79.9 mmol) and dimethylamino pyridine (105 mg, 0.75 mmol) in anhydrous CH$_2$Cl$_2$ (600 mL) was slowly added trifluoromethanesulfonic anhydride (10.72 mL, 65 mmol) at −20° C. The mixture was stirred at −20° C. for 5 min and then added a solution of 115 (10.2 g, 50 mmol) in CH$_2$Cl$_2$ (100.0 mL), and the reaction mixture stirred at −20° C. for 15 min. The TLC (15% ethyl acetate/hexane) indicated completion of the reaction. The reaction mixture was poured into a mixture of ice-water (500 mL) and the organic layer was separated. The aqueous phase was extracted with CH$_2$Cl$_2$ (2×100 mL). The combined organic layer was washed with water (2×250 mL) and brine (500 mL), dried (NaSO$_4$) and evaporated to obtain the intermediate triflate product as a pale yellow gummy solid (16 g).

To a solution of above methyl-4-O-trifluoromethanesulfonyl-2,3-O-isopropylidene-β-D-lyxopyranoside (16 g) in DMF (300 mL) was cooled to 0° C. Lithium azide (12.5 g, 255.6 mmol) was added and stirred at 23° C. for 3 h. The reaction mixture was diluted with toluene (200 mL) and the volatiles were evaporated. The residue was dissolved in a mixture of CH$_2$Cl$_2$ (500 mL) and water (200 mL). The organic layer was separated and washed with water (2×250 mL), brine (300 mL), dried (NaSO$_4$) and evaporated to obtain an oily residue which upon purification by flash silica gel chromatography using hexane/ethyl acetate (100/0; 97.5/2.5; and 95/5) as the eluent afforded pure azido product 116 (5.74 g, 50.2%). $^1$H NMR (300 MHz, (CDCl$_3$): δ1.38 (s, 3H, CH$_3$), 1.55 (s, 3H, CH$_3$), 3.44 (s, 3H, OCH$_3$), 3.7–3.9 (m, 3H), 4.03 (dd, 1H, J=6.32 & 3.85 Hz), 4.49 (d, 1H, J=3.84 Hz), 4.52 (m, 1H).

Example 92

N-Acetyl-4-amino-4-deoxy-2,3-O-isopropylidene-β-L-methyl-ribopyranoside (117)

To a solution of 116 (12.1 g, 52.83 mmol) in MeOH (40.0 mL) was added Pd/C (5% w/w, 1.2 g) and the reaction mixture was shaken well under H$_2$ (50 psi) atmosphere at room temperature for 1 h. The TLC (30% ethyl acetate/hexane) indicated completion of the reaction. The reaction mixture was filtered over celite bed and the filtrate evaporated to dryness, and co-evaporated with toluene (2×50 mL)

and pyridine (2×25 mL). This residue was then carried forward for the next reaction without further purification.

To the above crude mixture was added DMAP (0.7 g, 5.0 mmol), pyridine (25.0 mL, 310.55 mmol) in $CH_2Cl_2$ (250.0 mL) followed by acetic anhydride (25.0 mL, 265.0 mmol) at −5° C. (ice-acetone bath). After the addition, the cooling bath was removed and the reaction mixture was stirred for 16 h. The TLC (100% ethyl acetate) indicated completion of the reaction. MeOH (10.0 mL) was added and the volatiles were evaporated. The residue was dissolved in $CH_2Cl_2$ (300 mL) and this solution was then washed with water (2×200 mL) and brine (200 mL), dried ($Na_2SO_4$) and evaporated. The residue was purified by flash chromatography using ethyl acetate/hexane (from 5/95 to 20/80 to 60/40 to 80/20) as the eluent to obtain the product 117 (in a combined yield of 11.49 g, 88.83%). $^1$H NMR (300 MHz, ($CDCl_3$): δ1.34 (s, 3H, $CH_3$), 1.51 (s, 3H, $CH_3$), 1.99 (s, 3H, $COCH_3$), 3.37 (t, 1H), 3.83 (dd, 1H, J=5.77 & 5.49 Hz), 4.01 (t, 1H, J=5.77 & 4.67 Hz), 4.35 (t, 1H, J=5.5 & 4.67 Hz), 4.40 (d, 1H, J=4.4 Hz), 4.54 (m, 1H), 5.76 (bd, 1H, J=7.97 Hz),.

Example 93

1,2,3,5-Tetra-O-acetyl-4-deoxy-4-(acetamido)-L-ribofuranose (118)

A solution of 117 (8.9 g) in a mixture of distilled water and AcOH (1:1, 100 mL) was heated at 70–75° C. for 1.5 h. TLC (100% ethyl acetate) indicated completion of the reaction. Absolute EtOH (2×50 mL) was added and co-evaporated to obtain a dry solid residue. To this solid was added a mixture of glacial acetic acid and acetic anhydride (100.0 mL, 1:1) and cooled to 0° C. (ice-water bath), and treated with conc. $H_2SO_4$ (1.0 mL). The reaction mixture was stirred at 0° C. for 30 min and then kept at 4° C. for 2 days. The reaction mixture was treated with anhydrous NaOAc (10.0 g) and stirred at room temperature for 30 min. The reaction mixture was then poured into ice-water mixture (400 mL) and extracted with $CH_2Cl_2$ ((2×250 mL). The combined organic layer was washed with water (2×500 mL) and brine (400 mL), dried ($Na_2SO_4$) and evaporated. The crude product that obtained was purified by flash chromatography using ethyl acetate/hexane (25/75 to 50/50) as the eluent to obtain 118 (6.6 g, 50.67%). $^1$H NMR (300 MHz, ($CDCl_3$): δ2.0–2.12 (m, 15H, 5×$COCH_3$), 4.18–4.51 (m, 3H), 5.33–5.36 (m, 1H), 5.45–5.55 (m, 1H), 6.36 (s, 0.75H), 6.55 (d, 0.25H, J=5.22 Hz).

Example 94

Methyl-1-(2',3',5'-triacetyl-4'-deoxy-4'-acetamido-β-L-ribofuranosyl)-1,2,4-triazole-3-carboxylate (119)

A suspension of methyl-1,2,4-triazole-3-carboxylate (1.022 g, 8.05 mmol) and ammonium sulphate (100 mg) in hexamethyldisilazane (20 mL) was refluxed for 2.5 h under $N_2$ atmosphere. The volatiles were evaporated and the residue was suspended in 1,2-dichloroethane (50 mL). It was then treated with a solution of 118 (2.513 g, 7 mmol) in 1,2-dichloroethane (50 mL). To the reaction mixture was then added fuming $SnCl_4$ (0.94 mL, 8.05 mmol) at 0–5° C. (ice-water bath). The reaction mixture was stirred at room temperature for 1 h. The reaction was carefully quenched with saturated solution of $NaHCO_3$ (50 mL) and diluted with $CH_2Cl_2$ (200 mL). The mixture was filtered over a celite bed (5 g) and washed with $CH_2Cl_2$ (100 mL). The organic layer of the filtrate was separated and the aqueous layer was extracted with $CH_2Cl_2$ (2×100 mL). The combined organic layer was washed with water (2×300 mL) and brine (500 mL), dried ($Na_2SO_4$) and evaporated. The crude residue was crystallized from ethyl acetate (40 mL) to obtain pure titled product 119 (1.8 g, 60.36%). $^1$H NMR (300 MHz, ($CDCl_3$): δ2.03–2.14 (m, 12H, 4×$COCH_3$), 3.93 (s, 3H, $OCH_3$), 4.2 (m, 1H, $H_5$'), 4.41 (m, 2H, $H_4$'& $H_5$'), 5.64 (d, 1H, $H_3$', J=4.67 Hz), 6.16 (t, 1H, $H_2$', J=4.95 & 5.77 Hz), 6.27 (d, 1H, $H_1$', J=6.05 Hz), 8.46 (s, 0.86H, major rotamer, $C_5H$), 8.60 (s, 0.14H, minor rotamer, $C_5H$). Anal. Calcd. for $C_{17}H_{22}N_4O_9$: C, 47.89; H, 5.20; N. 13.14. Found: C, 47.77; H, 5.49; N, 13.04.

Example 95

1-(4'-Deoxy-4'-acetamido-β-L-ribofuranosyl)-1,2,4-triazole-3-carboxamide (120)

A solution of 119 (3.26 g, 7.65 mmol) in saturated methanolic ammonia (100 mL) was stirred at room temperature for 16 h. The reaction was evaporated to dryness and the residue was purified by flash chromatography over alumina using the solvent mixture ethyl acetate/n-propyl alcohol/water (lower layer, 64/4/32 to 57/14/29%) to afford the titled product 120 (1.7 g, 77.98%). $^1$H NMR (300 MHz, (DMSO-$d_6$+$D_2O$): δ1.64 (s, 0.75H, $COCH_3$, minor rotamer (min)), 2.0 (s, 2.25H, $COCH_3$ major rotamer (maj)), 3.84–3.54 (m, 3H, H-$_4$'& H-$_5$'), 4.1 (m, 1H, H-$_3$'), 4.32 (t, 0.25H, J=4.4 Hz, H-$_2$', min), 4.56 (t, 0.75H, J=4.2 Hz, H-$_2$', maj), 5.82 (d, 0.75H, J=6.32 Hz, H-$_1$', maj), 6.01 (d, 0.25H, J=4.4 Hz, H-$_1$', min), 8.74 (s, 0.75H, $C_5H$, maj), 8.96 (s, 0.25H, $C_5H$, min).). Anal. Calcd. for $C_{10}H_{15}N_5O_5$: C, 42.10; H, 5.30; N. 24.55. Found: C, 42.44; H, 5.49; N, 24.69.

Example 96

1-[(3',5'-O-(1,1,3,3-Tetraisopropyl-1,3-disiloxanediyl)-4'-deoxy-4'-acetamido-β-L-ribofuranosyl]-1,2,4-triazole-3-carboxamide (121)

A suspension of 120 (0.75 g, 2.63 mmol) in pyridine (15 mL) was treated with 1,3-dichloro-1,1,3,3-tetraisopropyl-disiloxane (1.09 mL, 3.42 mmol) and stirred at room temperature for 16 h. The reaction mixture was carefully quenched with saturated solution of $NaHCO_3$ (5 mL) and diluted with $CH_2Cl_2$ (100 mL). The organic layer was separated and the aqueous layer was extracted with $CH_2Cl_2$ (2×25 mL). The combined organic layer was washed with water (2×100 mL) and brine (100 mL), dried ($Na_2SO_4$) and evaporated. The crude residue that obtaine was purified by flash chromatography over silica gel using $CHCl_3$/MeOH (100/0-98/2-95/5-90/10) as the eluent to afford the product 121 (0.75 g, 54%). $^1$H NMR (300 MHz, $CDCl_3$): δ0.93–1.17 (m, 24H), 1.37 (m, 2H), 2.01 (s, 1H, $COCH_3$, minor rotamer (min)), 2.14 (s, 2H, $COCH_3$, major rotamer (maj)), 2.98 (s, 0.34H, OH, exchangeable, min), 3.34 (s, 0.66H, OH, exchangeable, maj), 3.78–3.84 (m, 1H, $H_5$'), 3.97–4.14 (m, 2H, $H_4$' & $H_5$'), 4.33 (d, 0.34H, J=4.12 Hz, $H_2$', min), 4.41 (d, 0.66H. J=4.95 Hz, $H_2$', maj), 4.52 (m, $H_4$', min), 4.65 (m, $H_3$', min), 5.28 (t, J=4.95 Hz, $H_3$', maj), 5.80 (s, 0.66H, exchangeable, maj), 5.95 (s, 0.34H, exchangeable, min), 5.97 (s, 0.34H, $H_1$', min), 6.39 (s, 0.66H, $H_1$', maj), 6.89 (s, 0.66H, exchangeable, maj), 7.00 (s, 0.34H, exchangeable, min), 8.37 (s, 0.66H, $C_5H$, maj), 8.52 (s, 0.34H, $C_5H$, min).

Example 97

1[2' O (p Toluoylthionoformyl)3',5' O (1,1,3,3 tetraisopropyl 1,3 disiloxanediyl)-4'-deoxy-4'-acetamido-β-L-ribofuranosyl]-1,2,4-triazole-3-carboxamide (122).

To a solution of 121 (0.65 g, 1.23 mmol) in a mixture of $CH_2Cl_2$ (9 mL) and pyridine (1 mL) was added O-(p-tolyl) thionochloroformate (0.285 mL, 1.85 mmol) and the reaction mixture was stirred at room temperature for 16 h. The reaction mixture was quenched with saturated solution of $NaHCO_3$ (5 mL) and diluted with $CH_2Cl_2$ (100 mL). The organic layer was separated and the aqueous layer was extracted with $CH_2Cl_2$ (2×25 mL). The combined organic layer was washed with water (2×100 mL) and brine (100 mL), dried ($Na_2SO_4$) and evaporated. The crude residue that obtained was purified by flash chromatography over silica gel using $CHCl_3$/ethyl acetate (100/0-95/5-90/10) as the eluent to afford the product 122 (0.33 g, 39.52%). $^1H$ NMR (300 MHz, $CDCl_3$): δ0.92–1.15 (m, 24H), 2.01 (s, 1H, $COCH_3$, minor rotamer (min)), 2.19 (s, 2H, $COCH_3$, major rotamer (maj)), 2.35 (s, 3H, $CH_3$), 3.92 (m, 1H, $H_{5'}$), 4.07 (m, 2H, $H_{4'}$ & $H_{5'}$), 4.68–4.8 (m, $H_{3'}$, min), 5.50 (m, $H_{3'}$, maj), 5.7 (s, 0.66H, exchangeable, maj), 5.82 (s, 0.34H, exchangeable, min), 6.10 (d, 1H, J=4.94 Hz, $H_{2'}$), 6.17 (s, 0.34H, $H_{1'}$, min), 6.54 (s, 0.66H, $H_{1'}$, maj), 6.70 (s, 0.34H, exchangeable, min), 6.86 (s, 0.66H, exchangeable, maj), 6.96 (d, 2H, J=8.52 Hz, aromatic-H), 7.21 (d, 2H, J=8.24 Hz aromatic-H), 8.40 (s, 0.66H, $C_5H$, maj), 8.69 (s, 0.34H, $C_5H$, min).

Example 98

1-[(3',5'-O-(1,1,3,3-Tetraisopropyl-1,3-disiloxanediyl)-2',4'-dideoxy-4'-acetamido-β-L-ribofuranosyl]-1,2,4-triazole-3-carboxamide (123)

A solution of 122 (0.325 g, 0.48 mmol) in toluene (20 mL) was purged with argon for 20 min. To the solution were added 2,2'-azobisisobutyronitrile (0.078 g, 0.48 mmol) and tributyltin hydride (0.25 mL, 0.96 mmol). The reaction mixture was refluxed for 6 h under a stream of argon. The reaction was evaporated to dryness and the crude residue was purified by flash chromatography over silica gel using $CHCl_3$/ethyl acetate (100/0-90/10-70/30-40/60-20/80-0/100) as the eluent to afford 123 (0.22 g, 89.68%). $^1H$ NMR (300 MHz, $CDCl_3$): δ0.92–1.15 (m, 24H), 1.28 (m, 2H), 2.0 (s, 0.66H, $COCH_3$, minor rotamer (min)), 2.13 (s, 2.34H, $COCH_3$, major rotamer (maj)), 2.36–2.58 (m, 1H, $H_{2'}$), 2.85 (dd, 1H, J=13.73 & 7.41 $H_{2'}$), 3.74–4.09 (m, 3H, $H_{4'}$ & $H_{5'}$), 4.49–4.67 (m, $H_{3'}$, min), 5.30 (m, $H_{3'}$, maj), 5.83 (s, 0.8H, exchangeable, maj), 5.94 (s, 0.2H, exchangeable, min), 6.14 (d, 0.2H, J=6.05 Hz, $H_{1'}$, min), 6.54 (d, 0.8H, J=8.24 Hz, $H_{1'}$, maj), 6.89 (s, 0.8H, exchangeable, maj), 7.04 (s, 0.2H, exchangeable, min), 8.35 (s, 0.8H, $C_5H$, maj), 8.55 (s, 0.2H, $C_5H$, min).

Example 99

1-(2',4'-Dideoxy-4'-acetamido-β-L-ribofuranosyl)-1,2,4-triazole-3-carboxamide (124)

A solution of 123 (0.2 g, 0.39 mmol) in $CH_2Cl_2$ (5 mL) was treated with triethylamine tris-hydrofluoride (0.25 mL, 1.56 mmol) at room temperature. The reaction mixture was stirred for 48 h and the volatiles were evaporated to dryness. The residue was purified by flash chromatography over silica gel using $CHCl_3$/MeOH (100/0-95/5-90/10-85/15) as the eluent to afford 124 (0.08 g, 66%). $^1H$ NMR (300 MHz, $CD_3OD$): δ1.95 (s, 0.36H, $COCH_3$, minor rotamer (min)), 2.16 (s, 2.64H, $COCH_3$, major rotamer (maj), 2.51 (m, 1H, $H_{2'}$), 2.87 (m, 1H, $H_{2'}$), 3.82 (m, 2H, $H_{5'}$), 3.99 (t, 1H, J=6.87 Hz, $H_{4'}$), 4.44 (d, 1H, J=4.12 Hz, $H_{3'}$), 6.54 (t, 1H, J=7.69 Hz, $H_{1'}$), 8.63 (s, 0.88H, $C_5H$, maj), 8.88 (s, 0.12H, $C_5H$, min). Anal. Calcd. for $C_{10}H_{15}N_5O_4$: C, 44.60; H, 5.62; N, 26.01. Found: C, 44.69; H, 5.71; N, 26.10.

Example 100

1-(2',3',5'-Tri-O-acetyl-4'-deoxy-4'-acetamido-β-L-ribofuranosyl) thymine (125)

A suspension of thymine (1.26 g, 10 mmol) and ammonium sulphate (126 mg) in hexamethyldisilazane (25 mL) was refluxed for 5 h under $N_2$ atmosphere. The reaction mixture was evaporated to dryness and the residue suspended in 1,2-dichloroethane (50 mL). A solution of 118 (2.513 g, 7 mmol) in 1,2-dichloroethane (50 mL) was added followed by fuming $SnCl_4$ (1.17 mL, 10 mmol, 1.42 eq) at 0–5° C. (ice-water bath). The reaction mixture was stirred at room temperature for 1 h. The reaction mixture was carefully quenched with saturated solution of $NaHCO_3$ (50 mL) and diluted with $CH_2Cl_2$ (200 mL). The mixture was filtered over a celite bed (5 g) and washed with $CH_2Cl_2$ (100 mL). The organic layer of the filtrate was separated and the aqueous layer was extracted with $CH_2Cl_2$ (2×100 mL). The combined organic layer was washed with water (2×300 mL) and brine (500 mL), dried ($Na_2SO_4$) and evaporated. The residue obtained was purified by flash chromatography over silica gel using $CHCl_3$/acetone (95/5-90/10-85/15-80/20) as the eluent to obtain pure titled product 125 (2.9 g, quantitative). $^1H$ NMR (300 MHz, $CDCl_3$): δ1.89–2.2 (m, 15H, 4×$COCH_3$ & $C_5CH_3$), 4.08 (m, 0.5H, $H_{5'}$), 4.37–4.56 (m, 2.5H, $H_{4'}$ & $H_{5'}$), 5.32 (m, 0.5H, $H_{3'}$), 5.47 (m, 1.5H, $H_{2'}$ & $H_{3'}$), 6.15 (m, 0.5H, $H_{1'}$), 6.37 (d, 0.5H, J=6.6 Hz, $H_{1'}$), 7.16 (s, 0.5H, $C_6H$), 7.44 (s, 0.5H, $C_6H$), 9.02 (s, 0.5H, NH, exchangeable), 9.20 (s, 0.5H, NH exchangeable).

Example 101

1-(4'-Deoxy-4'-acetamido-β-L-ribofuranosyl) thymine (126)

A solution of 125 (3.1 g, 7.29 mmol) in saturated methanolic ammonia (100 mL) was stirred at room temperature in a steel bomb for 16 h. The steel bomb was cooled to 0° C., opened and evaporated to dryness. The residue was purified by flash silica gel chromatography over silica gel using $CHCl_3$/MeOH (95/5-90/10-85/15) as the eluent to afford the titled product 126 (1.72, 78.86%). $^1H$ NMR (300 MHz, ($DMSO-d_6+D_2O$): δ1.70 (s, 1.35H, $COCH_3$, minor rotamer (min)), 1.73 (s, 1.35H, $C_5CH_3$), 1.77 (s, 1.65H, $C_5CH_3$), 1.98 (s, 1.65H, $COCH_3$, major rotamer (maj), 3.95–3.57 (m, 4H, $H_{3'}$, $H_{4'}$ & $H_{5'}$), 4.13 (t, 0.55H, , J=4.67 Hz, $H_{2'}$, maj), 4.20 (dd, 0.45H, J=4.4 Hz, $H_{2'}$, min), 5.72 (d, 0.45H, J=6.6 Hz, $H_{1'}$, min), 5.88 (d, 0.55H, j=5.77 Hz, $H_{1'}$, maj), 7.68 (s, 0.45H, $C_6H$, min), 8.00 (s, 0.55H, $C_6H$, maj). Anal. Calcd. for $C_{12}H_{17}N_3O_6$: C, 48.16; H, 5.73; N, 14.04. Found: C, 48.23; H, 5.81; N, 14.29.

Example 102

1-[(3',5'-O-(1,1,3,3-Tetraisopropyl-1,3-disiloxanediyl)-4'-deoxy-4'-acetamido-β-L-ribofuranosyl]thymine (127) & 1-[(2',3'-O-(1,1,3,3-Tetraisopropyl-1,3-disiloxanediyl)-4'-dideoxy-4'-acetamido-β-L-ribofuranosyl]thymine (128)

A suspension of 126 (1.72 g, 5.75 mmol) in pyridine (25 mL) was treated with 1,3-dichloro-1,1,3,3-tetraisopropyldisiloxane (2.75 mL, 8.59 mmol) and stirred at room temperature for 16 h. The reaction mixture was carefully quenched with saturated solution of NaHCO$_3$ (5 mL) and diluted with CH$_2$Cl$_2$ (100 mL). The organic layer was separated and the aqueous layer was extracted with CH$_2$Cl$_2$ (2×25 mL). The combined organic layer was washed with water (2×100 mL) and brine (100 mL), dried (Na$_2$SO$_4$) and evaporated. The crude residue was purified by flash chromatography over silica gel using hexane/ethyl acetate (90/10-80/20-60/40-20/80-0/100) as the eluent to afford a mixture of inseparable regio isomeric products 127 & 128 (2.15 g, 69%). $^1$H NMR (300 MHz, CDCl$_3$): δ1.0 (m), 1.9–2.13 (m), 3.79–4.13 (m), 4.3–4.47 (m), 4.74 (d), 5.07–5.21 (m), 5.47 (s), 5.84 (s), 5.93 (d, J=3.3 Hz), 7.20 (s), 7.40(s), 7.53 (s), 7.78 (s), 8.88 (s), 9.13 (s), 9.67 (s).

Example 103

1-[2'-O-(p-Tolylthionoformyl)-3',5'-
O-(1,1,3,3-tetrailopropyl-1,3-disiloxanediyl)-4'-deoxy-
4'-acetamido-β-L-ribofuranosyl]thymine (129) & 1-
[5'-O-(p-Tolylthionoformyl)-2',3'-
O-(1,1,3,3-tetraisopropyl-1,3-disiloxanediyl)-4'-deoxy-
4'-acetamido-β-L-ribofuranosyl]thymine (103)

To a mixture of 127 and 128 (2 g, 3.69 mmol) in pyridine (20 mL) was added O-(p-toluoyl)thionochloroformate (0.712 mL, 4.43 mmol) and the reaction mixture was stirred at room temperature for 16 h. The reaction mixture was quenched with saturated solution of NaHCO$_3$ (5 mL) and diluted with CH$_2$Cl$_2$ (100 mL). The organic layer was separated and the aqueous layer was extracted with CH$_2$Cl$_2$ (2×25 mL). The combined organic layer was washed with water (2×100 mL) and brine (100 mL), dried (Na$_2$SO$_4$) and evaporated. The crude residue was purified by flash chromatography over silica gel hexane/ethyl acetate (90/10-80/20-70/30-40/60) as the eluent to afford a faster product (0.9 g) and a slower product (0.8 g). The combined yield of both the products was 1.7 g (66.54%). The $^1$H NMR analysis of both the products indicated that the slower product was 129 while the faster product was 130. 129: $^1$H NMR (300 MHz, CDCl$_3$): δ0.98–1.06 (m, 24H), 1.89 (s, 3H, CH$_3$), 2.00 (s, 2H, COCH$_3$, major rotamer, (maj)), 2.25 (s, 1H, COCH$_3$, minor rotamer,(min)), 2.34 (s, 3H, CH$_3$), 3.85–4.03 (m, 2H, H$_{5'}$), 4.38–4.80 (m, 2H, H$_{3'}$ & H$_{4'}$), 5.3 (m, 0.24H, H$_{2'}$, min), 5.7 (m, 0.76H, H$_{2'}$, maj), 6.01 (s, 1H, H$_{1'}$), 6.95 (d, 2H, J=8.52 Hz, aromatic-H), 7.20 (d, 2H, J=8.52 Hz, aromatic-H), 7.35 (s, 0.24H, C$_6$H), 7.57 (s, 0.76H, C$_6$H), 8.23 (bs, 0.24H, NH, exchangeable), 8.64 (s, 0.76H, NH, exchangeable). 130: $^1$H NMR (300 MHz, CDCl$_3$): δ1.00–1.06 (m, 26H), 1.87 (s, 3H, CH$_3$), 2.02 (s, 2.4H, COCH$_3$, major rotamer,(maj)), 2.22 (s, 0.6H, COCH$_3$, minor rotamer,(min)), 4.22–4.5 (m, 3H, H$_{4'}$ & H$_{5'}$), 4.88 (m, 1H, H$_{3'}$), 5.22 (m, 1H, H$_{2'}$), 6.01 (d, 1H, J=3.02 Hz, H$_{1'}$), 6.94 (d, 2H, J=8.24 Hz, aromatic-H), 7.21 (d, 2H, J=8.52 Hz, aromatic-H), 7.78 (s, 1H, C$_6$H), 8.38 (bs, 0.16H, NH, exchangeable, min), 8.44 (s, 0.84H, NH, exchangeable, maj).

Example 104

1-[(3',5'-
O-(1,1,3,3-Tetraisopropyl-1,3-disiloxanediyl)-
2',4'-dideoxy-4'-acetamido-β-L-ribofuranosyl]
thymine (131)

A solution of 129 (0.74 g, 1.070 mmol) in toluene (25 mL) was purged with argon for 20 min. To this solution was added 2,2'-azobisisobutyronitrile (0.174 g, 1.074 mmol) followed by tributyltinhydride (0.56 mL, 2.113 mmol, 2 eq). The reaction mixture was refluxed for 6 h under a stream of argon. The volatiles were evaporated and the crude residue was purified by flash chromatography over silica gel using hexane/ethyl acetate (100/0-90/10-80/20-70/30-60/40) as the eluent to afford 131 (0.45 g, 80.03%). $^1$H NMR (300 MHz, CDCl$_3$): δ0.98–1.06 (m, 24H), 1.26 (m, 2H), 1.90 (s, 3H, CH$_3$), 1.97 (s, 2.25H, COCH$_3$, major rotamer,(maj)), 2.17 (s, 0.75H, COCH$_3$, minor rotamer,(min)), 2.2–2.4 (m, 1.5H, H$_{2'}$), 2.65 (m, 0.5H, H$_{2'}$), 3.67 (m, 1H, H$_{5'}$), 4.0 (m, 1H, H$_{5'}$) 4.32 (m), 4.64 (m, 1H, H$_{4'}$), 5.12 (m, 1H, H$_{3'}$), 5.71 (m, 0.15H, H$_{1'}$, min), 6.05 (m, 0.85H, J=6.05 Hz, H$_{1'}$, maj), 7.33 (s, 0.15H, C$_6$H, min), 7.53 (s, 0.85H, C$_6$H, maj), 8.23 (bs, 0.15H, NH, exchangeable, min), 8.76 (s, 0.85H, NH, exchangeable, maj).

Example 105

1-(2',4'-Dideoxy-4'-acetamido-β-L-ribofuranosyl)
thymine (132)

A solution of 131 (0.38 g, 0.72 mmol) in CH$_2$Cl$_2$ (10 mL) was treated with triethylamine tris-hydrofluoride (0.585 mL, 3.6 mmol) at room temperature. The reaction mixture was stirred for 48 h and evaporated to dryness. The residue was purified by flash chromatography over silica gel using CHCl$_3$/MeOH (100/0-97/3-94/6-90/10) as the eluent to the titled compound 132 (0.19 g, 92.75%). $^1$H NMR (300 MHz, CD$_3$OD): δ1.83 (s, 1.35H, C$_5$CH$_3$), 1.86 (s, 1.65H, C$_5$CH$_3$), 1.95 (s, 1.35H, COCH$_3$, minor rotamer (min)), 2.18 (s, 1.65H, COCH$_3$, major rotamer (maj)), 2.37 (m, 2H, H$_{2'}$), 4.05–3.73 (m, 3H, H$_{4'}$ & H$_{5'}$), 4.32 (d, 0.55H, J=3.85 Hz, H$_{3'}$, maj), 4.36 (bs, 0.45H, H$_{3'}$, min), 6.26 (t, 0.45H, J=8.2 Hz, H$_{1'}$, min), 6.49 (t, 0.55H, J=7.4 Hz, H$_{1'}$, maj), 7.70 (s, 0.55H, C$_6$H, maj) 8.18 (s, 0.45H, C$_6$H, min) Anal. Calcd. for C$_{12}$H$_{17}$N$_3$O$_5$.½H$_2$O: C, 49.31; H, 6.21; N, 14.38. Found: C, 49.49; H, 6.43; N, 14.51.

Example 106

1-[(2',3'-
O-(1,1,3,3-Tetraisopropyl-1,3-disiloxanediyl)-
5',4'-dideoxy-4'-acetamido-β-L-ribofuranosyl]
thymine (133)

A solution of 130 (1.35 g, 1.954 mmol) in toluene (40 mL) was purged with argon for 20 min. To this solution was added 2,2'-azobisisobutyronitrile (0.32 g, 1.954 mmol) and tributyltinhydride (1.035 mL, 3.905 mmol). The reaction mixture was refluxed for 1.5 h under a stream of argon. The reaction mixture was evaporated to dryness. The crude residue was purfied by flash chromatography over silica gel using hexane/ethyl acetate (100/0-90/10-80/20-70/30-60/40) as the eluent to 133 (0.7 g, 68.24%). $^1$H NMR (300 MHz, CDCl$_3$); δ0.98–1.05 (m, 24H), 1.24 (m, 2H), 1.46 (d, 1.2H, H$_{5'}$, minor rotamer(min), 1.52 (d, 2.8H, J=6.9 Hz, H$_{5'}$, major rotamer(maj), 1.89 (s, 1.2H, COCH$_3$, min), 1.93 (s, 3H, CH$_3$), 2.09 (s, 2.8H, COCH$_3$, maj), 3.86 (m, 0.6H, H$_{4'}$, maj), 3.98 (m, 0.4H, H$_{4'}$, min), 4.12–4.36 (m, 1H, H$_{3'}$), 5.18 (m, 1H, H$_{2'}$), 5.30 (d, 0.6H, J=6.05 Hz, H$_{1'}$, maj), 5.98 (d, 0.4H, J=3.57 Hz, H$_{1'}$, min) 6.99 (s, 0.4H, C$_6$H, min), 7.08 (s, 0.6H, C$_6$H, maj), 8.53 (bs, 0.6H, NH, exchangeable, maj) 8.66 (bs, 0.4H, NH, exchangeable, min).

Example 107

1-(5',4'-Dideoxy-4'-acetamido-β-L-ribofuranosyl) thymine (134)

A solution of 133 (0.6 g, 1.14 mmol) in $CH_2Cl_2$ (20 mL) was treated with triethylamine tris-hydrofluoride (0.558 mL, 3.42 mmol) at room temperature. The reaction mixture was stirred at room temperature for 20 h and the volatiles were evaporated to dryness. The residue was purified by flash chromatography over silica gel using $CHCl_3$/MeOH (100/0-97/3-94/6-90/10) as the eluent to afford 134 (0.2 g, 61.83%). $^1$H NMR (300 MHz, ($CD_3OD$): δ1.40 (d, 0.36H, J=6.87 Hz, $H_5$·, minor rotamer (min)), 1.48 (d, 0.64H, J=6.87 Hz, $H_5$·, major rotamer (maj)), 1.87 (s, 1.08H, $C_5CH_3$), 1.91 (s, 1.92H, $C_5CH_3$) 1.91 (s, 1.08H, $COCH_3$, min), 2.09 (s, 1.92H, $COCH_3$, maj), 3.84–4.09 (m, 2H, $H_3$· & $H_4$·) 4.33 (m, 0.36H, $H_2$·, min), 4.67 (m, 0.64H, $H_2$·, maj), 5.71 (d, 0.64H, J=6.87 Hz, $H_1$·, maj), 6.08 (d, 0.36H, J=5.77 Hz, $H_1$·, min), 7.21 (s, 0.36H, $C_6H$, min), 7.27 (s, 0.64H, $C_6H$, maj). Anal. Calcd. for $C_{12}H_{17}N_3O_5$: C, 50.88; H, 6.05; N, 14.83. Found: C, 50.91; H, 6.23; N, 14.91.

Example 108

1-(2',3',5'-O-Triacetyl-4'-deoxy-4'-acetamido-β-L-ribofuranosyl)-6-azauracil (135)

A suspension of 6-azauracil (0.909 g, 8.05 mmol) and ammonium sulphate (100 mg) in hexamethyldisilazane (20 mL) was refluxed for 2 h under $N_2$ atmosphere. The reaction mixture was evaporated to dryness and the residue was suspended in 1,2-dichloroethane (50 mL). To this stirred solution was added a solution of 118 (2.513 g, 7 mmol) in 1,2-dichloroethane (50 mL) followed by fuming $SnCl_4$ (0.94 mL, 8.05 mmol, 1.15 eq) at 0–5° C. (ice-water bath). The reaction mixture was stirred at room temperature for 16 h. The reaction mixture was carefully quenched with saturated solution of $NaHCO_3$ (50 mL) and diluted with $CH_2Cl_2$ (200 mL). The mixture was filtered over a celite bed (5 g) and washed with $CH_2Cl_2$ (100 mL). The organic layer of the filtrate was seperated and the aqueous layer was extracted with $CH_2Cl_2$ (2×100 mL). The combined organic layer was washed with water (2×300 mL) and brine (500 mL), dried ($Na_2SO_4$) and evaporated. The crude residue was purified by flash chromatography over silica gel using hexane/ethylacetate (85/15-70/30-50/50-30/70-0/100) as the eluent to obtain the titled product 135 (0.5 g, 17%). $^1$H NMR (300 MHz, $CDCl_3$); 2.01–2.15 (m, 12H), 4.12–4.48 (m, 3H, $H_4$· & $H_5$·), 5.47 (m, 1H, $H_3$·), 5.57(m, 0.2H, $H_2$·, minor rotamer (min)), 5.64 (m, 0.8H, $H_2$·, major rotamer (maj)), 6.41 (d, 0.2H, J=5.4 Hz, $H_1$·, min), 6.52 (d, 0.8H, J 7.2 Hz, $H_1$·, maj), 7.38 (d, 0.6H, J=2.1 Hz, $C_5H$, maj), 7.54 (s, 0.4H, $C_5H$, min), 9.22 (bs, 0.6H, NH, exchangeable, maj), 9.46 (bs, 0.4H, NH, exchangeable, min).

Example 109

1-(2',3',5'-O-Triacetyl-4'-deoxy-4'-acetamido-β-L-ribofuranosyl)-6-carbomethoxyuracil (136)

A suspension of 6-carbomethoxyuracil (1.7 g, 10 mmol) and ammonium sulphate (170 mg) in hexamethyldisilazane (25 mL) was refluxed for 2 h under $N_2$ atmosphere. The volatiles were evaporated and the residue was suspended in 1,2-dichloroethane (50 mL). To this was added a solution of 118 (2.513 g, 7 mmol) in 1,2-dichloroethane (50 mL) followed by fuming $SnCl_4$ (1.17 mL, 10 mmol, 1.42 eq) at 0–5° C. (ice water bath). The reaction mixture was stirred at room temperature for 16 h. The reaction mixture was carefully quenched with saturated solution of $NaHCO_3$ (50 mL) and diluted with $CH_2Cl_2$ (200 mL). The mixture was filtered over a celite bed (5 g). The organic layer of the filtrate was separated and the aqueous layer was extracted with $CH_2Cl_2$ (2×100 mL). The combined organic layer was washed with water (2×300 mL) and brine (500 mL), dried ($Na_2SO_4$) and evaporated. The crude residue was purified by flash chromatography over silica gel using hexane/ethylacetate (95/5-80/20-70/30-50/50) as the eluent to obtain the titled product 136 (2.2 g, 67%). $^1$H NMR (300 MHz, $CDCl_3$): 1.99–2.10 (m, 12H), 3.92 (s, 2H, $OCH_3$, major rotamer (maj)), 3.98 (s, 1H, $OCH_3$, minor rotamer (min)), 4.00–4.07 (m, 1H, $H_5$·), 4.53 (m, 2H, $H_4$· & $H_5$·), 5.48 (d, 0.8H, J=4.67 Hz, $H_3$·, maj), 5.53 (d, 0.2H, J=4.94 Hz, $H_3$·, min), 6.13 (m, 0.2H, $H_2$·, min), 6.20 (dd, 0.8H, J=4.67 & 7.96 Hz, $H_2$·, maj), 6.30 (s, 0.8H, $H_1$·, maj), 6.37 (s, 0.2H, $H_1$·, min), 6.58 (d, 0.2H, J=6.87 Hz, $C_5H$, min), 6.68 (d, 0.8H, J=7.99 Hz, $C_5H$, maj), 8.70 (bs, 0.8H, NH, exchangeable maj), 8.89 (bs, 0.2H, NH, exchangeable, min).

Example 110

1-(2',3',5'-O-Triacetyl-4'-deoxy-4'-acetamido-β-L-ribofuranosyl)-5-fluorouracil (137)

A suspension of 5-fluorouracil (1.3 g, 10 mmol) and ammonium sulphate (130 mg) in hexamethyldisilazane (25 mL) was refluxed for 4 h under $N_2$ atmosphere. The reaction mixture was evaporated to dryness and the residue was suspended in 1,2-dichloroethane (50 mL). The solution was then treated with a solution of 118 (2.513 g, 7 mmol) in 1,2-dichloroethane (50 mL) followed by fuming $SnCl_4$ (1.17 mL, 10 mmol, 1.42 eq) at 0–5° C. (ice-water bath). The reaction mixture was stirred at room temperature for 16 h. The reaction mixture was carefully quenched with saturated solution of $NaHCO_3$ (50 mL) and diluted with $CH_2Cl_2$ (200 mL). The mixture was filtered over a celite bed (5 g). The organic layer of the filtrate was separated and the aqueous layer was extracted with $CH_2Cl_2$ (2×100 mL). The combined organic layer was washed with water (2×100 mL) and brine (500 mL), dried ($Na_2SO_4$) and evaporated. The crude residue was purified by flash chromatography over silica gel using $CHCl_3$/acetone (80/20) as the eluent to provide pure product 137 (1 g, 33.30%). $^1$H NMR (300 MHz, $CDCl_3$ ): 2.02–2.21 (m, 12H), 4.10 (m, 0.5H, $H_5$·), 4.43–4.56 (m, 2.5H, $H_4$· & $H_5$·), 5.30 (m, 0.5H, $H_3$·), 5.43–5.54 (m, 1.5H, $H_2$· & $H_3$·), 6.09 (t, 0.5H, J=6.32 & 4.94 Hz, $H_1$·), 6.28 (d, 0.5H, J=4.94 Hz, $H_1$·), 7.48 (d, 0.5H, J=5.77 Hz, $C_6H$), 7.95 (d, 0.5H, J=5.77 Hz, $C_6H$), 9.19 (bs, 0.5H, NH, exchangeable), 9.34 (bs; 0.5H, NH, exchangeable).

Example 111

1-(2',3',5'-O-Triacetyl-4'-deoxy-4'-acetamido-β-L-ribofuranosyl)-5-fluorocytosine (138)

A suspension of 5-fluorocytosine (1.29 g, 10 mmol, 1.42 eq) and ammonium sulphate (322 mg) in hexamethyldisilazane (40 mL) was refluxed for 4 h under $N_2$ atmosphere. The volatiles were evaporated and the residue was suspended in 1,2-dichlorothane (50 mL). To this stirred solution was added a solution of 118 (2.513 g, 7 mmol) in 1,2-dichloroethane (50 mL) followed by fuming $SnCl_4$ (1.17 mL, 10 mmol, 1.42 eq) at 0–5° C. (ice-water bath). The reaction mixture was stirred at room temperature for 16 h. The reaction mixture was carefully quenched with saturated solution of NaHCO$_3$ (50 mL) and diluted with CH$_2$Cl$_2$ (200 mL). The mixture was filtered over a celite bed (5 g). The organic layer of the filtrate was separated and the aqueous layer was extracted with CH$_2$Cl$_2$ (2×100 mL). The combined organic layer was washed with water (2×300 mL) and brine (500 mL), dried (Na$_2$SO$_4$) and evaporated. The crude residue was purified by flash chromatography over silica gel using CHCl$_3$/acetone (80/20) to obtain pure product 138 (1 g, 33.55%). $^1$H NMR (300 MHz, CDCl$_3$): 1.98–2.18 (m, 12H), 4.08 (m, 0.5H, H$_{5''}$), 4.37–4.61 (m, 2.5H, H$_{4'}$ & H$_{5'}$), 5.28 (m, 1H, H$_{3'}$), 5.44 (t, 0.8H, J=4.67 Hz, H$_{2'}$, major rotamer (maj)), 5.55 (d, 0.2H, J=4.39 Hz, H$_{2'}$, major rotamer (min)), 5.76 (bs, 1H, NH$_2$, exchangeable), 6.27 (bt, 0.23H, H$_{1'}$, min), 6.37 (d, 0.77H, J=3.57 Hz, H$_{1'}$, maj), 7.49 (d, 0.23H, J=5.77 Hz, C$_6$H, min), 7.79 (bs, 1H, NH$_2$ exchangeable), 7.94 (d, 0.77H, J=6.32 Hz, C$_2$H, maj).

Example 112

1-(4'-Deoxy-4'-acetamido-β-L-ribofuranosyl)-6-azauracil (139)

A solution of 135 (0.45 g, 1.09 mmol) in saturated methanolic ammonia (10 mL) was stirred in a steel bomb at room temperature for 16 h. The steel bomb was cooled, opened and evaporated to dryness. The residue was purified by flash chromoatography over silica gel using CHCl$_3$/MeOH (95/5-90/10-85/15) as the eluent to afford the titld product 139 (0.18 g, 57.62%). $^1$H NMR (300 MHz, DMSO-d$_6$): δ1.84 (s, 1.35H, COCH$_3$, minor rotamer (min)), 1.95 (s, 1.65H, COCH$_3$, major rotamer (maj)), 3.46–3.85 (m, 3H, H$_{4'}$ & H$_{5'}$), 4.01 (m, 1H, H-$_{3'}$), 4.22 (m, 1H, H$_{2'}$), 4.89 (m, 0.45H, OH, min, exchangeable), 5.01 (m, 0.55H, OH, maj, exchangeable),), 5.15 (s, 0.45H, OH, min, exchangeable), 5.28 (s, 0.55H, OH, maj, exchangeable), 5.39 (d, 0.45H, J=6.86 Hz, OH, min, exchangeable), 5.50 (d, 0.55H, J=5.7 Hz, OH, maj, exchangeable), 6.0 (d, 0.45H, J=7.15 Hz, H$_{1'}$, min), 6.05 (d, 0.55H, J=5.5 Hz, H$_{1'}$, maj), 7.50 (s, 0.45H, C$_5$H, min), 7.61 (s, 0.55H, C$_5$H, maj), 12.2 (bs, 1H, NH, exchangeable). Anal. Calcd. for C$_{10}$H$_{14}$N$_4$O$_6$: C, 41.96; H, 4.93; N, 19.57. Found: C, 42.03; H, 5.11; N, 19.64.

Example 113

1-(4'-Deoxy-4'-acetamido-β-L-ribofuranosyl)uracil-6-carboxamide (140)

A solution of 136 (2 g, 4.26 mmol) in saturated methanolic ammonia (20 mL) was stirred at room temperature in a steel bomb for 16 h. The steel bomb was cooled, opened and evaporated to dryness. The residue that obtained was purified by flash chromatography over silica gel using CHCl$_3$/MeOH (95/5–90/10–85/15) as the eluent to afford the titled product 140 (1 g, 71.49%). $^1$H NMR (300 MHz, DMSO-d$_6$+D$_2$O): δ1.70 (s, 1H, COCH$_3$, minor rotamer (min)), 1.89 (s, 2H, COCH$_3$, major rotamer (maj)), 3.97–3.44 (m, 4H, H$_{3'}$, H$_{4'}$ & H$_{5'}$), 4.73(m, 1H, H$_{2'}$), 6.26–6.08 (m, 2H, C$_5$H & H$_{1'}$), Anal. Calcd. for C$_{12}$H$_{16}$N$_4$O$_7$: C, 43.90; H, 4.91; N, 17.07 Found: C, 43.99; H, 5.06; N, 17.21.

Example 114

1-(4'-Deoxy-4'-acetamido-β-L-ribofuranosyl)-5-fluorouracil (141)

A solution of 137 (1 g, 2.33 mmol) in saturated methanolic ammonia (20 mL) was stirred in a steel bomb at room temperature for 16 h. The steel bomb was cooled to 0° C., opened and evaporated to dryness. The residue was purified by flash chromatography over silica gel using CHCl$_3$/MeOH (95/5-90/10-85/15) as the eluent to afford the titled product 141 (0.6 g, 84.95%), $^1$H NMR (300 MHz, (DMSO-d$_6$+D$_2$O): δ1.72 (s, 1.35H, COCH$_3$, minor rotamer (min)), 1.83 (s, 1.65H, COCH$_3$, major rotamer (maj)), 3.35–4.18 (m, 5H, H$_{2'}$, H$_{3'}$, H$_{4'}$ & H$_{5'}$), 5.74 (d, 0.45H, J=5.77 Hz, H$_{1'}$, min), 5.84 (d, 0.55H, J=4.1 Hz, H$_{1'}$, maj), 8.25 (s, 0.45H, C$_6$H, min), 8.53 (s, 0.55H, C$_6$H, maj), 11.77 (bs, 1H, NH, exchangeable). Anal. Calcd. for C$_{11}$H$_{14}$FN$_3$O$_6$: C, 43.57; H, 4.65; N, 13.86. Found: C, 43.40; H, 4.71; N, 13.80.

Example 115

1-(4'-Deoxy-4'-acetamido-β-L-ribofuranosyl)-5-fluorocytosine (142)

A solution of 138 (1 g, 2.33 mmol) in saturated methanolic ammonia (20 mL) was stirred in a steel bomb at room temperature for 16 h. The steel bomb was cooled to, opened and evaporated to dryness. The residue was purified by flash chromatography over silica gel using CHCl$_3$/MeOH (95/5-90/10-85/15) as the eluent to afford the titled product 142 (0.64 g, 90.70%). $^1$H NMR (300 MHz, CD$_3$OD): δ1.92 (s, 2H, COCH$_3$, major rotamer (maj)), 2.17(s, 1H, COCH$_3$, minor rotamer (min)), 3.75–3.93 (m, 2H, H$_{5'}$), 4.16–4.28 (m, 1.5H, H$_{3'}$ & H$_{4'}$), 4.49 (t, 0.5H, J=4.4 & 4.94 Hz, H$_{3'}$), 4.65 (s, 1H, H$_{2'}$), 5.77 (d, 0.33H, J=5.22 Hz, H$_{1'}$, min), 6.11 (dd, 0.66H, J=1.92 & 4.12 Hz, H$_{1'}$, maj), 8.19 (d, 0.33H, J=6.86 Hz, C$_6$H, min), 8.66 (d, 0.66H, J=7.15 Hz, C$_6$H, maj). Anal. Calcd. for C$_{11}$H$_{15}$FN$_4$O$_5$: C, 43.71; H, 5.00; N, 18.54. Found: C, 43.77; H, 5.17; N, 18.79.

It is to be understood that the above-described embodiments are illustrative only and that modifications thereof may occur to those skilled in the art. Accordingly, this invention is not to be regarded as limited to the embodiments disclosed herein, but is to be limited only as defined by the appended claims.

We claim:

1. A compound having a structure according to Formula I:

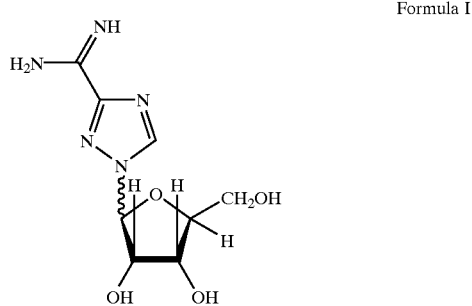

Formula I and pharmaceutically acceptable salts thereof.

2. The compound of claim 1 consisting of one of the salts.

3. The compound according to claim 2 having a structure according to Formula II:

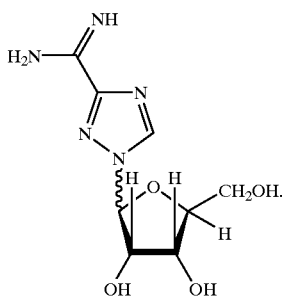
Formula II
4. The compound of claim 1 wherein the triazole heterocyclic base is in beta configuration relative to the ribose sugar.
5. A pharmaceutcal composition comprising a compound according to any one of claims 1, 2, 3, or 4 or a pharmaceutcally acceptable ester or prodrug thereof, admixed with at least one pharmaceutically acceptable carrier.
* * * * *